US007711085B2

(12) United States Patent
Suzuki et al.

(10) Patent No.: US 7,711,085 B2
(45) Date of Patent: May 4, 2010

(54) RADIOGRAPHY APPARATUS WITH SCOUT VIEW FUNCTION

(75) Inventors: Masakazu Suzuki, Kyoto (JP); Hideki Yoshikawa, Kyoto (JP); Takahiro Yoshimura, Kyoto (JP); Makoto Honjo, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 44 days.

(21) Appl. No.: 11/918,184

(22) PCT Filed: Apr. 11, 2006

(86) PCT No.: PCT/JP2006/307679

§ 371 (c)(1),
(2), (4) Date: Dec. 17, 2007

(87) PCT Pub. No.: WO2006/109808

PCT Pub. Date: Oct. 19, 2006

(65) Prior Publication Data

US 2009/0041191 A1     Feb. 12, 2009

(30) Foreign Application Priority Data

| Apr. 11, 2005 | (JP) | ............................. 2005-113994 |
| Oct. 26, 2005 | (JP) | ............................. 2005-311066 |
| Apr. 11, 2006 | (JP) | ............................. 2006-109230 |

(51) Int. Cl.
*A61B 6/14* (2006.01)
(52) U.S. Cl. ................................................. 378/39
(58) Field of Classification Search ............... 378/4, 378/38, 39, 95, 114, 115, 116
See application file for complete search history.

(56) References Cited

U.S. PATENT DOCUMENTS

| 4,852,134 A * | 7/1989 | Kinanen et al. ............... 378/38 |
| 2009/0041191 A1* | 2/2009 | Suzuki et al. .............. 378/98.5 |

FOREIGN PATENT DOCUMENTS

| DE | 199 41 668 | 9/2000 |
| DE | 103 13 110 | 10/2004 |
| JP | S63-288138 | 11/1988 |
| JP | 07-275240 | 10/1995 |
| JP | 9-98971 | 4/1997 |
| JP | 09-122118 | 5/1997 |
| JP | 11-104127 | 4/1999 |
| JP | 11-104128 | 4/1999 |
| JP | 2000-139902 | 5/2000 |
| WO | WO 2004/084728 | 10/2004 |

\* cited by examiner

*Primary Examiner*—Chih-Cheng G Kao
(74) *Attorney, Agent, or Firm*—William L. Androlia; H. Henry Koda

(57) ABSTRACT

An X-ray detecting section (13) comprises a first imaging means (S1) to generate an X-ray image in response to the X-ray slit beam (B) and a second imaging means (S2) to generate an X-ray image in response to the X-ray broad beam (BB). The radiography apparatus (M) displays a first X-ray image generated by the X-ray slit beam (B) and said first imaging means (S1), specifies a desired interested area (R) on the first X-ray image, and generates a predetermined sectional image as a second X-ray image by using the X-ray broad beam (BB) and the second imaging means (S2) with respect to the specified interested area (R).

11 Claims, 51 Drawing Sheets

| scout view image \ tomography | | panoramic tomography image | linear tomography image | CT image |
|---|---|---|---|---|
| image obtained by long and narrow X-ray image sensor | linear scan transmission image | ○ linear scan image may be obtained from one direction or two directions | ○ linear scan image is obtained from two directions | ○ linear scan image is obtained from two directions |
| | panoramic image | — | ○ | ○ |
| image obtained by rectangular 2D image sensor corresponding to X-ray broad beam | simple radiograpphy image | ○ simple radiography image may be obtained from one direction or two directions | ○ simple radiography image is obtained from two directions | ○ simple radiography image is obtained from two directions |
| | panoramic image | — | ○ | ○ |

*Fig. 7*

RADIOGRAPHY APPARATUS WITH SCOUT VIEW FUNCTION

TECHNICAL FIELD

This invention relates to an improvement of a radiography apparatus for setting an interested area in an object to be examined in order to capture a sectional image of the interested area.

BACKGROUND ART

In recent years, as an X-ray detector to obtain an X-ray image by measuring an X-ray, two kinds of imaging means such as a two-dimensional-type imaging means having a light receiving section in a rectangular shape close to a square, and a line-type imaging means provided with more elongate light receiving section, are available.

Digital radiography apparatuses utilizing the former two-dimensional-type imaging means are mostly used as a replacement of conventional X films, and such radiography apparatuses use various kinds of known radiographic principles of transmission images and sectional images.

Meanwhile, the digital radiography apparatuses using the latter line-type imaging means have a mechanism to obtain an X-ray transmission image by scanning an object to be examined using an X-ray slit beam along a predetermined radiographic orbit and tracking an X-ray passing through the object by a line-type imaging means so as to capture multiple strip-type X-ray images, followed by connecting and arranging these X-ray images in chronological order.

Patent Document 1 and Patent Document 2 mentioned below disclose radiography apparatuses which carries out panoramic radiography by means of line-type imaging means.

That is, Patent Document 1 discloses a radiography apparatus which allows versatile selection between panoramic radiography using a film cassette and panoramic radiography using a digital sensor cassette, where a line-type imaging means is used for a digital sensor cassette.

Patent Document 2 discloses a radiography apparatus in which an electric X-ray image detector is arranged as a line-type imaging means in an X-ray light receiving section provided in the center of the front surface of a cassette housing, and electrically controlled by control signals corresponding to rotation of a rotary arm so that an image signal required to generate a panoramic image can be outputted in a form of digital signals by converting the X ray into electrical signals.

Patent Document 3 discloses a medical radiography apparatus in which a vertically mobile patient frame for holding and fixing a head portion of a patient is provided to allow relative positional displacement between the patient frame and a rotary arm rotating its periphery so as to radiograph the desired position.

Patent Document 1: JP-A-H11-104127

Patent Document 2: JP-A-H11-104128

Patent Document 3: JP-A-H07-275240

DISCLOSURE OF INVENTION

Problems to be Solved by the Invention

Although the two-dimensional-type imaging means is available with extreme easiness as a replacement of a conventional X-ray film because of its shape, there is a problem of acquisition costs which is significantly increased in accordance with the size of its light receiving section, therefore it is practically difficult to use a two-dimensional-type imaging means of a large size. Moreover, in capturing a sectional plane by capturing a transmission image of an object to be examined and generating a sectional image from the captured transmission image, if the two-dimensional-type imaging means of the large size is used to irradiate an object to be examined with an X-ray cone beam corresponding to its size, a problem of exposure arises to a testee who is an object to be examined.

On the contrary, particularly in capturing a sectional image by generating a sectional image from a multiple number of transmission images, if it is configured to use a relatively narrow X-ray cone beam in a limited small portion in the vicinity of an interested area of the object without setting unnecessary other portions as an objective region in order to obtain an X-ray image by a two-dimensional-type imaging means of a size corresponding thereto, it is advantageous in terms of costs and exposure problems.

The purpose of this invention is to provide a newly configured radiography apparatus for accurately specifying a position of an interested area of an object to be examined, followed by capturing a sectional plane by using relatively narrow cone beam, particularly to cope with the exposure problems.

In order to solve the problems, a medical radiography apparatus as a first aspect includes a supporting means to support an X-ray generating section and an X-ray detecting section, both of the sections facing to each other, and a moving means to move the supporting means relative to an object to be examined held by an object holding means, whereby an X-ray image of the object is obtained by operating the moving means, while irradiating an X-ray beam from the X-ray generating section. The supporting means is turnable by the moving means, the X-ray generating section selectively generates an X-ray slit beam and an X-ray broad beam by switching control, and the X-ray detecting section comprises a first imaging means to generate an X-ray image in response to the X-ray slit beam and a second imaging means to generate an X-ray image in response to the X-ray broad beam. The medical radiography apparatus comprises a display section to display a first X-ray image generated by the X-ray slit beam and the first imaging means, an operating section to specify a desired interested area on the first X-ray image displayed in the display section, and a control means to control the moving means in order to generate a predetermined sectional image as a second X-ray image by using the X-ray broad beam and the second imaging means with respect to the interested area specified by the operating section.

And a medical radiography apparatus as a second aspect includes a supporting means to support an X-ray generating section and an X-ray detecting section, both of the sections facing to each other, and a moving means to move the supporting means relative to an object to be examined held by an object holding means, whereby an X-ray image of the object is obtained by operating the moving means, while irradiating an X-ray beam from the X-ray generating section. The supporting means is turnable by the moving means, the X-ray detecting section has a first imaging means extending in a direction parallel to a rotary shaft of the supporting means to generate an X-ray image in response to the X-ray slit beam and a second imaging means to generate an X-ray image in response to the X-ray broad beam, both of the imaging means being arranged on a single imaging plane, and the X-ray generating section has an irradiation field changing means to selectively generate the X-ray slit beam to be irradiated to the first imaging means and the X-ray broad beam to be irradiated to the second imaging means by switching the shape of the X-ray beams and to change an irradiation field of the X-ray broad beam in a direction parallel to an axial direction of the rotary shaft. The medical radiography apparatus comprises a display section to display a first X-ray image generated by the X-ray slit beam and the first imaging means, an operating section to specify a desired interested area on the first X-ray image displayed in the display section, and a control means to control the irradiation field changing means and the moving means in order to generate a second X-ray image as a CT image by the X-ray broad beam and the second imaging means with respect to the interested area specified by the operating section.

In a medical radiography apparatus as a third aspect, according to the first aspect, the X-ray detecting section comprises the first imaging means extending in a direction parallel to the rotary shaft of the supporting means and the second imaging means, both of the imaging means being arranged individually, and an imaging means moving means to move the second imaging means in a direction parallel to the rotary shaft of the supporting means. The X-ray generating section comprises an irradiation field changing means to change an irradiation field of the X-ray broad beam in a direction parallel to the rotary shaft. The medical radiography apparatus comprises a control means to control the imaging means moving means, the irradiation field changing means and the moving means in order to generate the second X-ray image as a CT image with respect to the interested area specified by the operating section.

In a medical radiography apparatus as a fourth aspect, according to the first aspect, the X-ray detecting section has the first imaging means extending in a direction parallel to the rotary shaft of the supporting means and the second imaging means, both imaging means being combined with each other, with a common shared portions. The X-ray generating section comprises an irradiation field changing means to selectively generate the X-ray slit beam to be irradiated to the first imaging means and the X-ray broad beam to be irradiated to the second imaging means by switching the shape of the X-ray beams, and the medical radiography apparatus comprises a control means to control the irradiation field changing means and the moving means in order to generate the second X-ray image as a CT image by the X-ray broad beam and the second imaging means with respect to the interested area specified by the operating section.

In a medical radiography apparatus as a fifth aspect, according to any one of the first to fourth aspects, at least one of a panoramic image, a cephalometric image, and a linear scan transmission image is generated as the first X-ray image.

In a medical radiography apparatus as a sixth aspect, according to any one of the first to fourth aspects, at least either a CT image or a linear sectional image is generated as the second X-ray image.

A medical radiography apparatus as a seventh aspect, according to any one of the first to sixth aspects, is characterized in that the X-ray generating section and the X-ray detecting section are moved by the moving means along an orbit for panoramic radiography in obtaining a panoramic image.

A medical radiography apparatus as an eighth aspect, according to any one of the first to seventh aspects, is characterized in that the moving means is controlled two-dimensionally in two directions defined on a plane intersecting the rotary shaft.

A medical radiography apparatus as a ninth aspect, according to any one of the first to seventh aspects, is characterized in that the moving means is controlled three-dimensionally in two directions defined on a plane intersecting the rotary shaft and in one direction parallel to the rotary shaft.

In a medical radiography apparatus as a tenth aspect, according to any one of the first to ninth aspects, the specified interested area is entirely projected while constantly projecting a part of the interested area by the second imaging means being offset forward or backward in a rotating direction of the X-ray detecting section, thereby realizing a computed tomography in the interested area.

In the first to tenth aspects, a sectional image of the specified interested area is captured as the second X-ray image by displaying the first X-ray image being a scout view image and specifying a desired interested area on the scout view image. The X-ray broad beam here may be expanded only in a size to cover a narrower interested area instead of the first X-ray image, so that exposure by the X-ray broad beam can be limited.

Particularly in the third aspect, an irradiation field of the X-ray broad beam is moved in a direction parallel to the rotary shaft with respect to the second imaging means, and the second imaging means is correspondingly moved in a direction parallel to the rotary shaft, so that the interested area can be set in a vertically moveable state. Moreover, the second imaging means may only need to have minimum expansion corresponding to the X-ray broad beam, which is advantageous in terms of costs.

Particularly in the fourth aspect, the first imaging means and the second imaging means are connected to share a part of an imaging plane each other and the size of the entire imaging plane is further reduced, which is advantageous in terms of costs.

Particularly in the eighth aspect, the moving means is made to implement two-dimensional control, which allows known techniques such as X-Y tables to be used and realizes easy control thereof.

Particularly in the ninth aspect, the moving means is made to implement three-dimensional control, so that the moving means can be used to position the interested area and flexibility of positioning the interested area is expanded.

Particularly in the tenth aspect, the interested area is entirely projected to the offset second imaging means while constantly projecting a part of the specified interested area, which exhibits an effect that the interested area can be expanded more than the case of capturing an image without offsetting as long as the same second imaging means is used.

BRIEF DESCRIPTION OF DRAWINGS

FIG. 7 is a chart showing possible combinations between a scout view image and sectional image capturing.

DESCRIPTION OF REFERENCE NUMERALS

Figure 1:
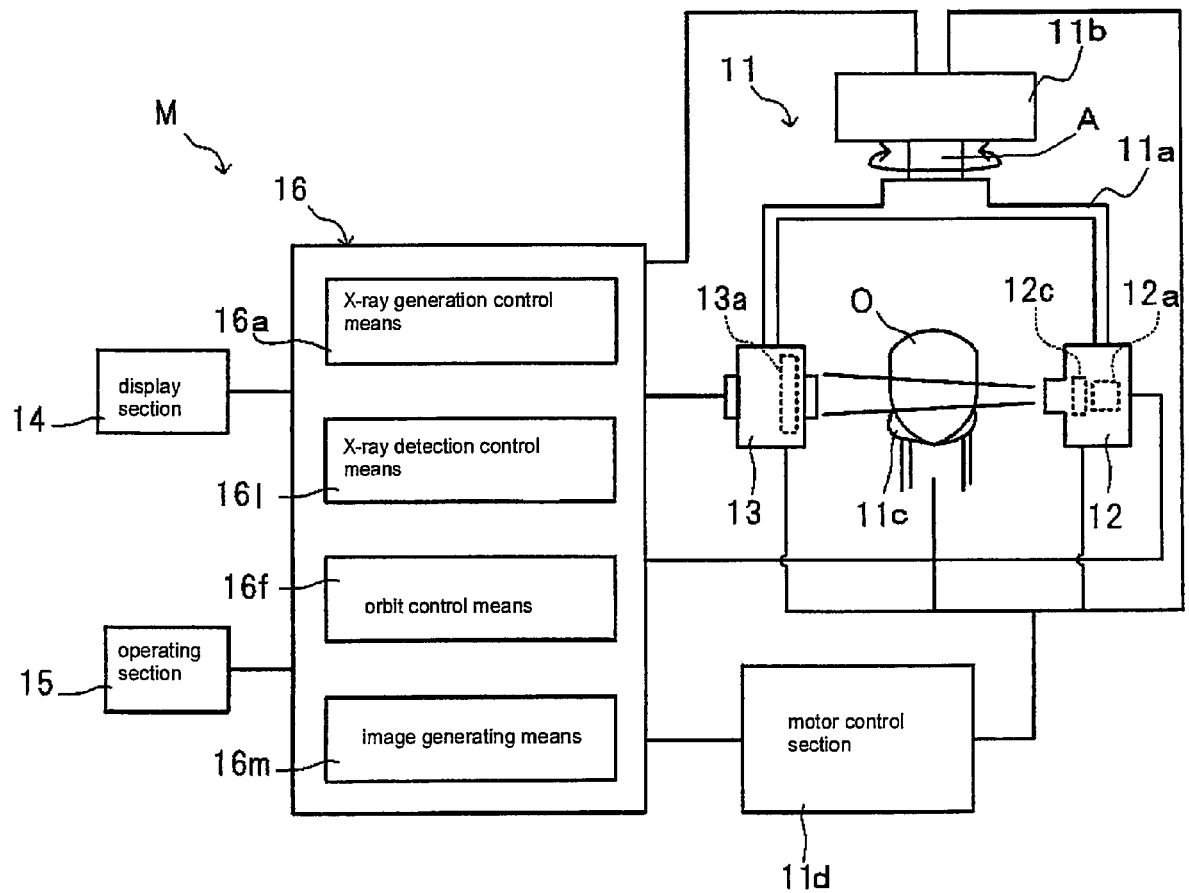
FIG. 1 is a block diagram to explain a schematic configuration of a radiography apparatus for use in embodiments.

11 . . . moving means
12 . . . X-ray generating section
13 . . . X-ray detecting section
14 . . . display section
15 . . . operating section
16 . . . control means
A . . . rotary shaft
B . . . X-ray slit beam
BB . . . X-ray broad beam
M . . . radiography apparatus
o . . . object to be examined
R . . . interested area
S1 . . . first imaging means
S2 . . . second imaging means

BEST MODE FOR CARRYING OUT THE INVENTION

Explained below in accordance with drawings are examples of a radiography apparatus provided with a scout view function in this invention. Although a medical radiography apparatus will be explained below, this invention is not limited to the medical radiography apparatus but also can be applied to radiography apparatuses for other fields such as industrial use.

Embodiment 1

FIG. 1 is a block diagram to explain a schematic configuration of a radiography apparatus M as an Example. FIG. 2 is Also a Schematic Diagram to Explain a mechanism of an X-ray generating section 12 for use in the radiography apparatus M, and FIG. 3a and FIG. 3b are outline view to explain examples of a basic configuration of an X-ray detecting section 13.

The radiography apparatus M is composed of a moving means 11 including the X-ray generating section 12 and the X-ray detecting section 13 which hold an object to be examined o by facing each other, and a control means 16 for controlling the X-ray generating section 12, the X-ray detecting section 13 and the moving means 11.

The X-ray generating section 12 is composed of an X-ray generator 12a for generating X-rays by a tube current and a tube voltage controlled by the control means 16, and a primary slit plate 12c for controlling an X-ray irradiation area, and the like.

Figure 2A:
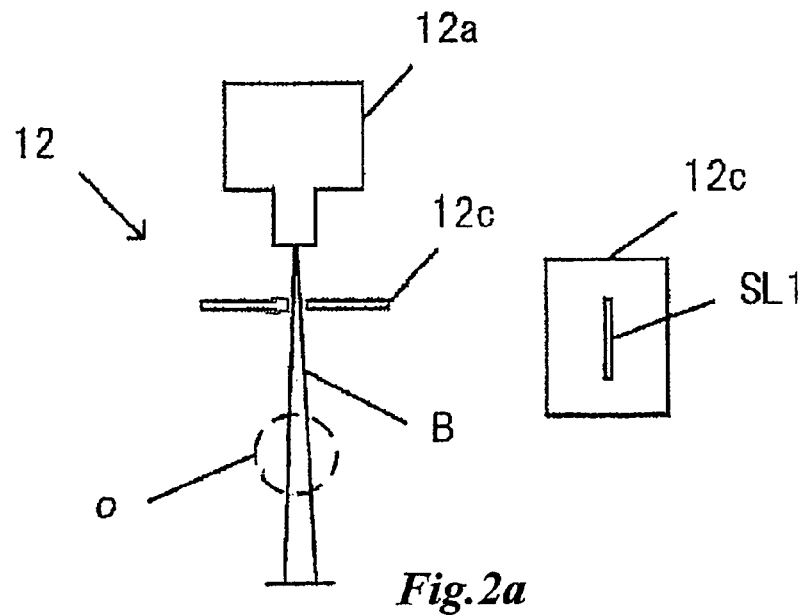
FIGS. 2a to 2c are three kinds of schematic diagrams to explain mechanisms of an X-ray generating section.
Figure 2B:
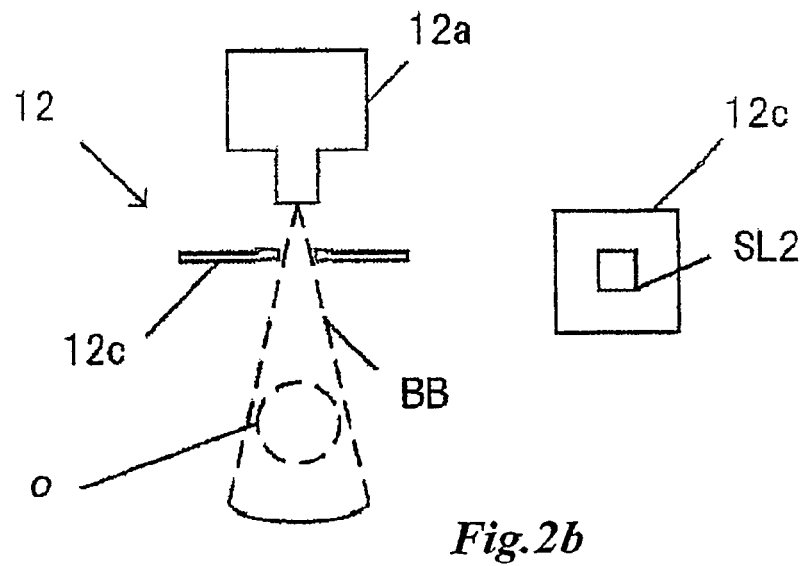
Figure 2C:
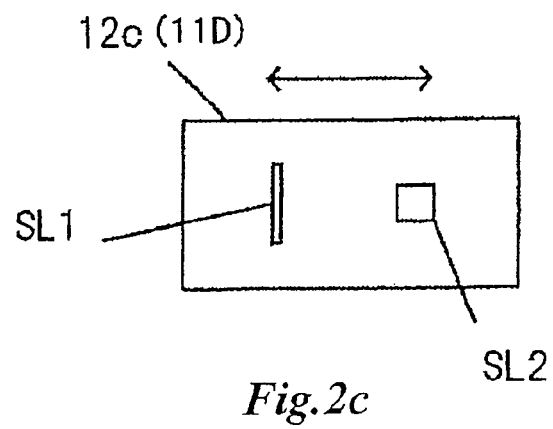
Figure 3A:
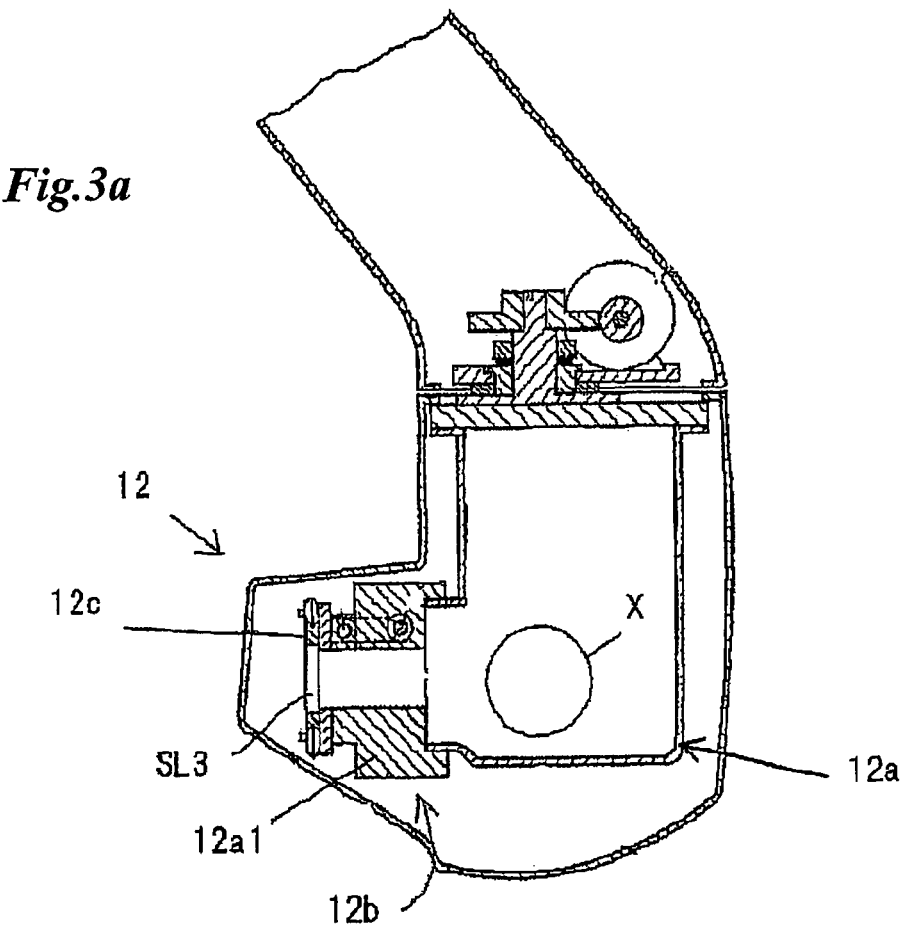
FIGS. 3a and 3b are a longitudinal sectional view and a perspective view to explain a configuration of the X-ray generating section respectively.
Figure 3B:
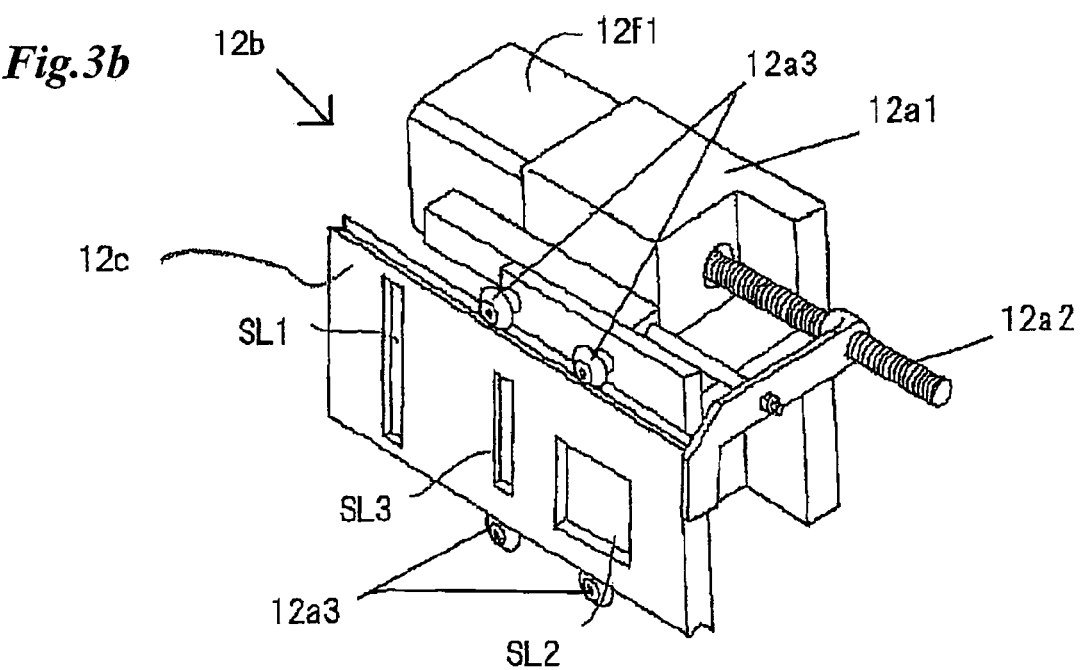

FIGS. 2a to 2c are three kinds of schematic diagrams to explain a mechanism of the X-ray generating section 12. The primary slit plate 12c shown in FIG. 2a is realized by forming a longitudinal narrow grooved slit SL1 (approx. aspect ratio of 20:1 to 100:1) in an X-ray shielding plate, so that an X-ray beam generated in the X-ray generator 12a is controlled by the narrow grooved slit SL1 and turned into a longitudinal X-ray slit beam B with a narrow width which is irradiated to an object to be examined o. Meanwhile, the primary slit plate 12c shown in FIG. 2b is realized by forming a rectangular slit SL2 (approx. aspect ration of 1:1 to 1:2) close to a square in an X-ray shielding plate, so that an X ray generated in the X-ray generator 12a is controlled by the rectangular slit. SL2 and turned into an X-ray broad beam BB being an X-ray cone beam with predetermined expansion which is irradiated to the object o.

The shape of an irradiation field of the X-ray slit beam B may be rectangular, elliptical, rectangular with four round corners, and other arbitrary shapes which can be realized by changing the shape of the narrow grooved slit SL1.

The shape of an irradiation field of the X-ray broad beam BB may be circular, elliptical, square, octagonal, and other arbitrary shapes. That is, the X-ray broad beam BB can be formed into various shapes such as a conical shape, quadrangular pyramid shape, and octagonal pyramid shape. This can be realized by changing the shape of the rectangular slit SL2.

Accordingly, the X-ray generating section 12 employing the primary slit plates 12c as shown in FIGS. 2a and 2b selects either one of the two primary slit plates 12c shown in FIGS. 2a and 2b by the control means 16, so that it makes it possible to selectively switch and generate the X-ray slit beam B and the X-ray broad beam BB corresponding to the selected primary slit plates 12c.

The primary slit plate 12c shown in FIG. 2c is realized by forming both of the above narrow grooved slit SL1 and the rectangular slit SL2 in one X-ray shielding plate. In the X-ray generating section 12 employing this primary slit plate 12c, an actuator or the like not shown is driven by the control means 16 so as to slide the primary slit plate 12c arranged in front of the X-ray generator 12a leftward and rightward, and thereby the X-ray slit beam B and the X-ray broad beam BB can be selectively switched and generated.

FIGS. 3a and 3b are a longitudinal sectional view and a perspective view respectively to explain a more detailed configuration of the X-ray generating section 12. The X-ray generating section 12 is composed of the X-ray generator 12a and an irradiation field control means 12b having the primary slit plate 12c and the like which includes the narrow grooved slit SL1 and the rectangular slit SL2, where either the X-ray slit beam B or the X-ray broad beam BB is selectively irradiated.

To be more specific, the X-ray generator 12a including an X-ray tube X having a fixed anode is incorporated in a housing of the X-ray generating section 12, where the primary slit plate 12c made of an X-ray shielding plate having a plurality of slits as shown in FIG. 2c and the irradiation field changing means 12b (or slit module) including an adjustment mechanism for changing the shape of the primary slit are arranged in a front surface facing the X-ray detecting section 13. The primary slit plate 12c is formed with the longitudinal narrow grooved slit SL1 for panoramic radiography, the rectangular slit SL2 for computed tomography, and a narrow grooved slit SL3 for cephalometric radiography, where the irradiation field changing means 12b slides the primary slit plate 12c using a driving motor 12f1 in order to establish the primary slit.

A fixed block 12a1 is fixed to a front surface of the X-ray generator 12a, and the driving motor 12f1 is fixed to the fixed block 12a1.

A driving shaft of the driving motor 12f1 drives the primary slit plate 12c which is movably guided by rollers 12a3 in a direction across X-ray beams so as to be displaced in the front surface of the X-ray generator 12a, where X-ray beams can be controlled by selecting the slit SL1, slit SL2 and slit SL3.

An irradiation angle of the X-ray slit beam B or the X-ray broad beam BB is basically, but not limited to, horizontal. Namely, a configuration where X-ray beams are irradiated at an irradiation angle oblique to a horizontal plane can also be considered. It is because metallic portions of dentures and the like cause a large artifact in radiography, and it is desired to capture images by avoiding the metallic portions. It is particularly problematic in taking CT images. In this case, it is therefore desired to irradiate the object o with the X-ray broad beam BB in an oblique state so as to avoid metallic portions.

Explained next will be a configuration of the X-ray detecting section 13.

Figure 4A:
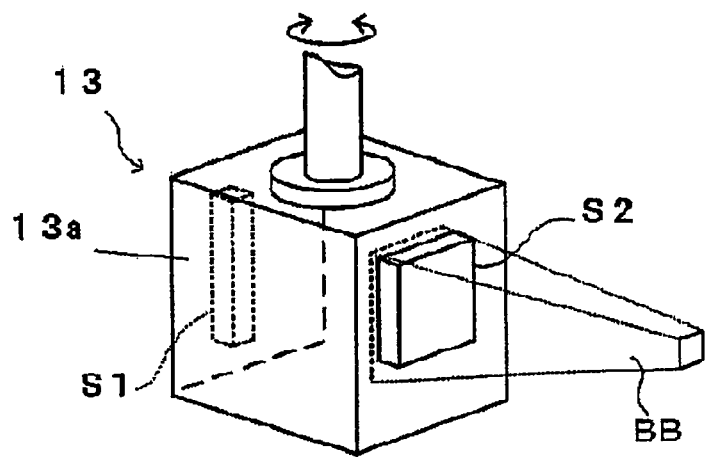
FIGS. 4a to 4c are conceptual diagrams to explain mutually different configurations of an X-ray detecting section.
Figure 4B:
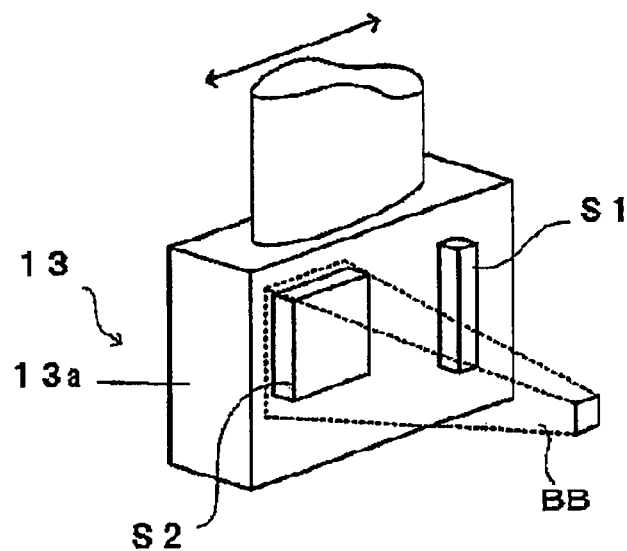

FIGS. 4a and 4b are conceptual diagrams to explain the configuration. The X-ray detecting section 13 is composed of an X-ray detector 13a. The X-ray detecting section 13 is integrated with the X-ray detector 13b and includes a first imaging means S1, and a second imaging means S2 corresponding to the X-ray slit beam B and the X-ray broad beam BB irradiated by the X-ray generating section 12 respectively. For example, the first imaging means S1 is preferably a line-type CCD imaging means having a longitudinal light receiving section corresponding to the X-ray slit beam B, and the second imaging means S2 is preferably a two-dimensional CMOS imaging means having a rectangular light receiving section corresponding to the X-ray broad beam BB. However, it is not limited and the both imaging means can be the CCD imaging means or the CMOS imaging means. That is, according to this invention, the imaging means do not have a limited configuration, and the first and second imaging means S1 and S2 are configured by any of CCD sensors, MOS sensors, CMOS sensors, TFT sensors, FT sensors, and X-ray solid-state image sensing device. Moreover, the shape of the second imaging means is not limited to be rectangular and may be other arbitral shapes. In summary, the second imaging means shall be a two-dimensional-type imaging means expanded corresponding to the X-ray broad beam BB, and allowed to have various shapes such as a circle, ellipse and octagon or the like.

Particularly in the X-ray detecting section 13 shown in FIG. 4a, the first imaging means S1 and the second imaging means S2 are provided on two surfaces forming front and rear surfaces to each other in a rectangular main body, where an actuator or the like not shown is driven by the control means 16 to horizontally rotate the entire body at 180 degrees, so that either the first imaging means S1 or the second imaging means S2 is selected to face the X-ray generating section 12.

On the contrary, in the X-ray detecting section 13 shown in FIG. 4b, the first imaging means S1 and the second imaging means S2 are both provided on one side surface of a rectangular main body, where the actuator or the like not shown is driven by the control means 16 to horizontally slide the entire body, so that either the first imaging means S1 or the second imaging means S2 is selected to face the X-ray generating section 12.

Figure 4C:
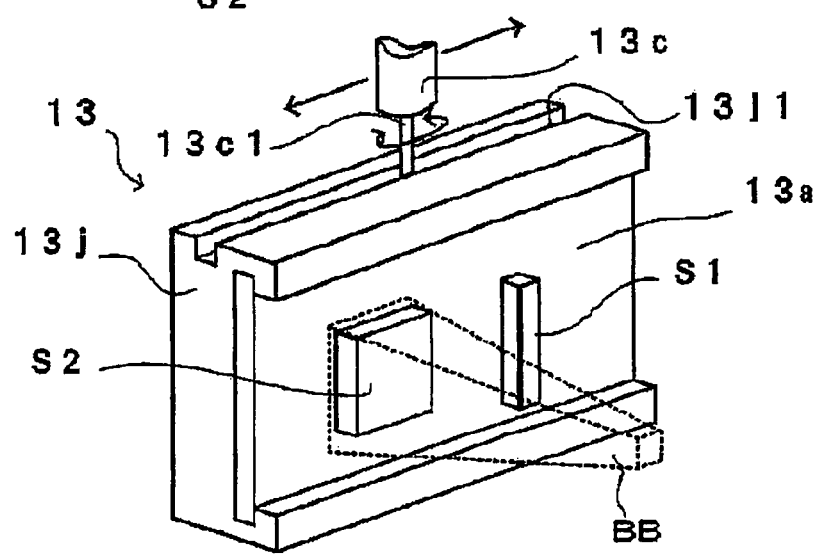

FIG. 4c shows an example of the X-ray detecting section 13 which is configured by a cassette holder 13j similar to a cassette holder of conventional panoramic radiography for mounting a film cassette, and the X-ray detector 13a attachable/detachable to/from the cassette holder 13j. The first imaging means S1 and the second imaging means S2 are both provided in a side surface of the X-ray detector 13a, where the cassette holder 13j can be displaced by a feed motor 13c whose rotary shaft 13c1 is connected to a groove 13J1 carved in a longitudinal direction in an upper portion of the cassette holder and which is fixed to a supporting means 11a to be described later, in a horizontal direction across an X-ray irradiation direction with respect to the supporting means 11a. The displacement in this horizontal direction can be used to offset the second imaging means S2 as described later.

Next, the moving means 11 is composed of the supporting means 11a including the X-ray generating section 12 and the X-ray detecting section 13, a fixed section 11b for vertically suspending and retaining a rotary shaft A of the supporting means 11a in a rotatable state and further allowing the rotary shaft A to move along a horizontal plane, and an object holding means 11c for positioning and holding the object o. Individual stepping motor controlled by the control means 16 is the driving source for turning movement of the supporting means 11a and a horizontal movement of the rotary shaft A. Furthermore, similar stepping motors may be used to move the object holding means 11c up and down.

The control means 16 is connected to a motor control section 11d having a stepping motor to drive the moving means 11, a display section 14 for displaying information such as X-ray images on television monitors and the like, and an operating section 15 for receiving an operation by keyboard and mouse and the like, and the control means functionally includes an X-ray generation control means 16a for selectively switching and generating the X-ray slit beam B and the X-ray broad beam BB by controlling the tube current and tube voltage of the X-ray generating section 12 and further operating the primary slit plate 12c, an X-ray detection control means 16l for taking control to obtain data of X-ray images transmitted through the object o in a state of facing either the first imaging means S1 or the second imaging means S2 to the X-ray generating section 12, an orbit control means 16f for moving the X-ray generating section 12 and the X-ray detecting section 13 along a radiographic orbit determined in accordance a radiography type by controlling the motor control section 11d and operating the moving means 11, and an image generating means 16m for taking control to generate transmission images and sectional images from obtained X-ray image data.

The display section 14 and the operating section 15 display a transmission image captured prior to objective tomography as a transmission image of the object o in a wide range, i.e. a scout view image, and constitute a radiography type selecting means for selecting a sectional plane to be captured or an interested area being a diagnosis part in the object o and further selecting a radiography type including sectional image capturing. Scout view images here are for use in preliminary radiography and preliminary diagnosis.

Next, a basic operation of the radiography apparatus M including capturing scout view images, selecting a radiography type, and capturing sectional images will be explained one by one.

Scout view image capturing is characterized in that a transmission image is obtained by scanning the object o by the X-ray slit beam B while moving the X-ray generating section 12 and the X-ray detecting section 13 synchronously along a predetermined radiographic orbit. As such a scout view image, a linear scan transmission image and a panoramic image and the like can be used, and it is set in advance by the radiography type selecting means to select a radiography type to be used.

In this image capturing, the radiographic orbit control means 16f reads out orbit data stored in a radiographic orbit memory not shown and controls the moving means 11 through the motor control section 11d in order to move the X-ray generating section 12 and the X-ray detecting section 13 synchronously along a radiographic orbit. The X-ray generation control means 16a also causes the X-ray generating section 12 to irradiate the X-ray slit beam B in order to scan the object o by following to a profile which is specifically intensity data registered in an irradiation intensity memory not shown. The X-ray detection control means 16l causes the first imaging means S1 to measure an X-ray transmitted through the object o and send the data to the image generating means 16m. When it is completed to capture images, the image generating means 16m processes a series of transmitted data by arranging the data in accordance with the time series and the like, so that a scout view image can be generated. The aforementioned profile may be selected in accordance with the sex and physique and the like of a testee who becomes the object o, or a control may be executed by feeding back the X-ray intensity measured by the first imaging means S1 without depending on the profile.

In radiography type selection, an image such as a linear scan transmission image, a panoramic image and other images captured as a scout view image is displayed in the display section 14 with a cursor which is moveable on the image, where operators use a mouse of the operating section 15 or the like to move the cursor to the interested area R such as a sectional plane and diagnosis part, and the interested area R can be confirmed by a mouse click operation and the like. Then, if a radiography type of a sectional image is selected by an operation such as pressing a predetermined key and the like, it starts to capture a selected sectional plane. As a sectional image, a linear sectional image, CT image and panoramic image can be selected.

In capturing a sectional image, the X-ray broad beam BB is irradiated from the X-ray generating section 12 while moving the X-ray generating section 12 and the X-ray detecting section 13 synchronously along a predetermined radiographic orbit, and transmission images of the object o are captured for a plurality of times as a frame having predetermined expansion by the second imaging means of the X-ray detecting section 13, so that a plurality of transmission images obtained corresponding to a position of a radiographic orbit is subjected to image processing such as composite or arithmetic processing in order to obtain sectional images of the interested area R.

In this radiography, the orbit control means 16f reads out orbit data stored in a radiographic orbit memory not shown and controls the moving means 11 through the motor control means 11d, so that the X-ray generating section 12 and the X-ray detecting section 13 are moved synchronously along a radiographic orbit. Moreover, the X-ray generation control means 16a causes the X-ray generating section 12 to irradiate the X-ray broad beam BB to the interested area R of the object o in a predetermined position of a radiographic orbit in accordance with a profile which is specifically intensity data registered in irradiation intensity memory not shown, and the X-ray detection control means 16*l* simultaneously causes the second imaging means S2 to measure an X-ray transmitted through the interested area R and transmit a transmission image to the image generating means 16*m* in each measurement. When it is completed to capture images, the image generating means 16*m* performs predetermined processes with respect to a plurality of the transmitted transmission images, so that a sectional image of the interested area. R can be generated. The aforementioned profile may be selected in accordance with the sex and physique of a testee who becomes the object o, or the control process may be achieved by feeding back X-ray intensity measured by the second imaging means S2 without depending on the profile.

Radiographic orbits for use in taking a scout view image including a linear scan transmission image and a panoramic image, and examples of the transmission images to be obtained will be explained here in accordance with diagrams.

Figure 5:
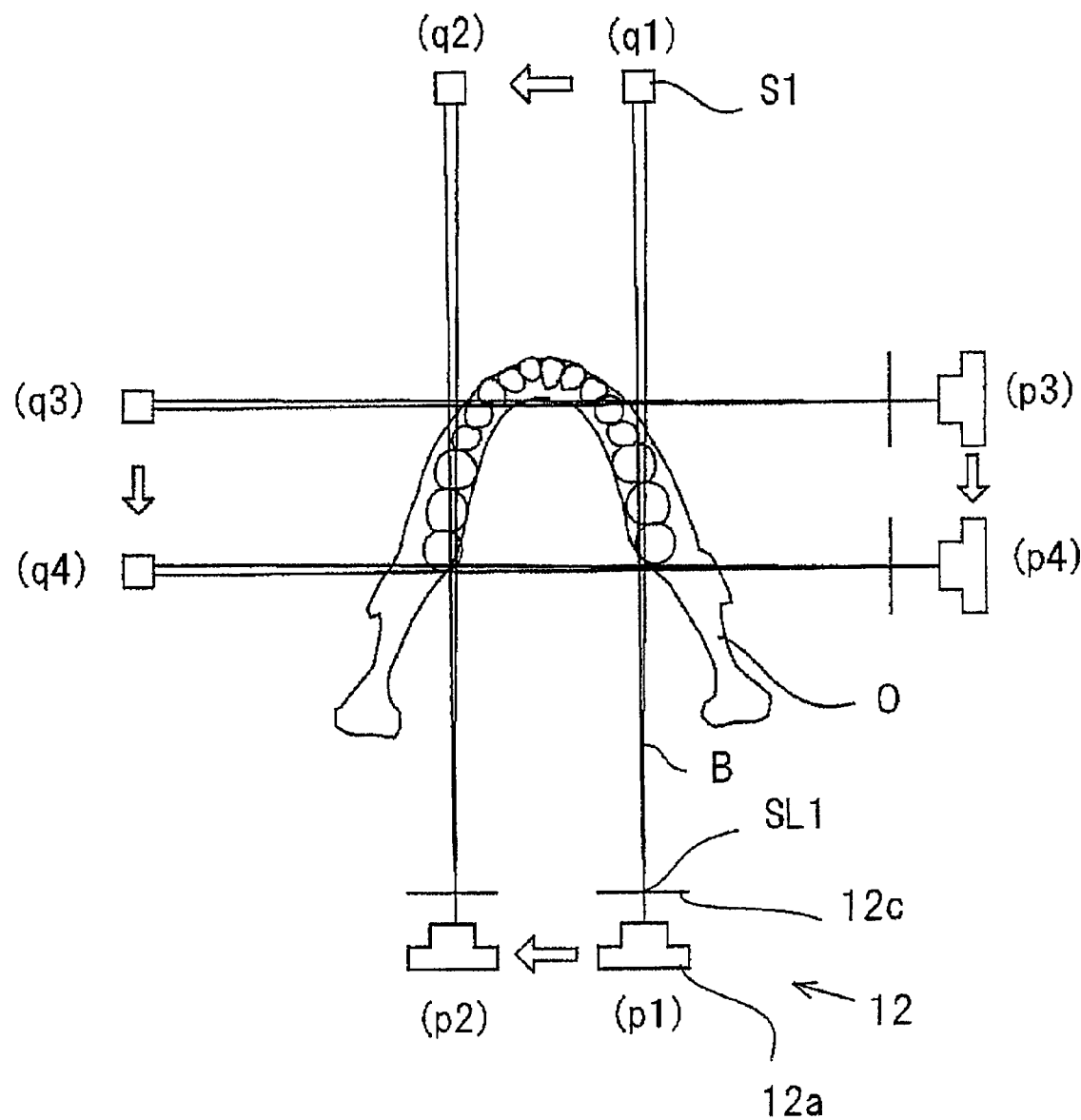
FIG. 5 is a plane view to explain a radiographic orbit in capturing a linear scan transmission image.
Figures 6A, 6B:
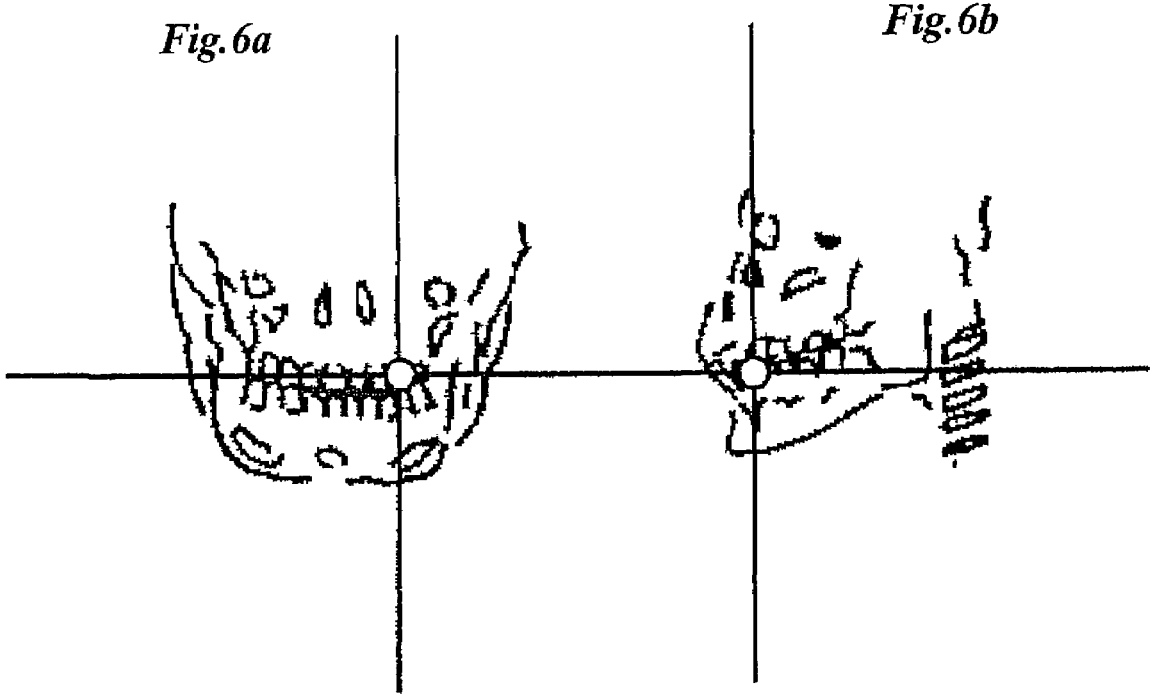
FIGS. 6a and 6b show examples of linear scan transmission images captured from two directions of an object to be examined.

FIG. 5 is a plane view to explain radiographic orbits where the X-ray generating section 12 and the X-ray detecting section 13 are moved synchronously in capturing a linear scan transmission image as a scout view image, while FIGS. 6*a* and 6*b* show examples of dual directional linear scan transmission images of the object o obtained by the radiography, and these images are turned into transmission images displayed in radiography type selection. In this example, a lower jaw of a human being is used as the object o, and a cross cursor for specifying the interested area R is also drawn therein.

In this case, the orbit control means 16*f* causes the X-ray generating section 12 which is made to irradiate the X-ray slit beam B, to move along a radiographic orbit in a direction from a position (p1) to a position (p2), and causes the first imaging means S1 of the X-ray detecting section 13 to move synchronously along the radiographic orbit in a direction from a position (q1) to a position (q2). Due to such scanning in accordance with a radiographic orbit, a front linear scan transmission image of the object o is obtained as shown in FIG. 6*a*.

Similarly, according to scanning of moving the X-ray generating section 12 which is made to irradiate the X-ray slit beam B, along a radiographic orbit in a direction from a position (p3) to a position (p4) and synchronously move the first imaging means S1 of the X-ray detecting section 13 along the radiographic orbit in a direction from a position (q3) to a position (q4), a side linear scan transmission image of the object o can be obtained as shown in FIG. 6*b*. Front and side linear scan transmission images of the object o thus captured are simultaneously displayed in the display section 14 and used to set the interested area R of the object o.

In the case of obtaining a scout view by the second imaging means S2, the X-ray broad beam BB may be used to obtain a simple X-ray transmission image (referred to as a "simple radiography" in this application), but a configuration of FIG. 51 can also be applied.

FIG. 51 shows an example of obtaining a scout view image from the X-ray slit beam B by using the second imaging means S2. Although a basic configuration remains the same with that of FIG. 5, the difference is to capture images by fixing the second imaging means S2. FIG. 51 shows that the top of a front teeth side of a dental arch is directed upward in the drawing, where the X-ray generator 11 is moved from right to left in the drawing in a direction from a position (p51) to a position (p52) in order to obtain a scout view.

It is of course possible to obtain scout views of front and side surfaces by this radiography method in the same manner with the example of FIG. 5.

An advantage of the configuration in FIG. 51 is to enable irradiation of a limited region in the second imaging means S2. If it is sufficient enough to obtain a scout view in the vicinity of one of temporomandibular joints for example, only the vicinity of one of temporomandibular joints can be irradiated. This radiography method is referred to as "transmission image scanning" in this application.

Figure 24:
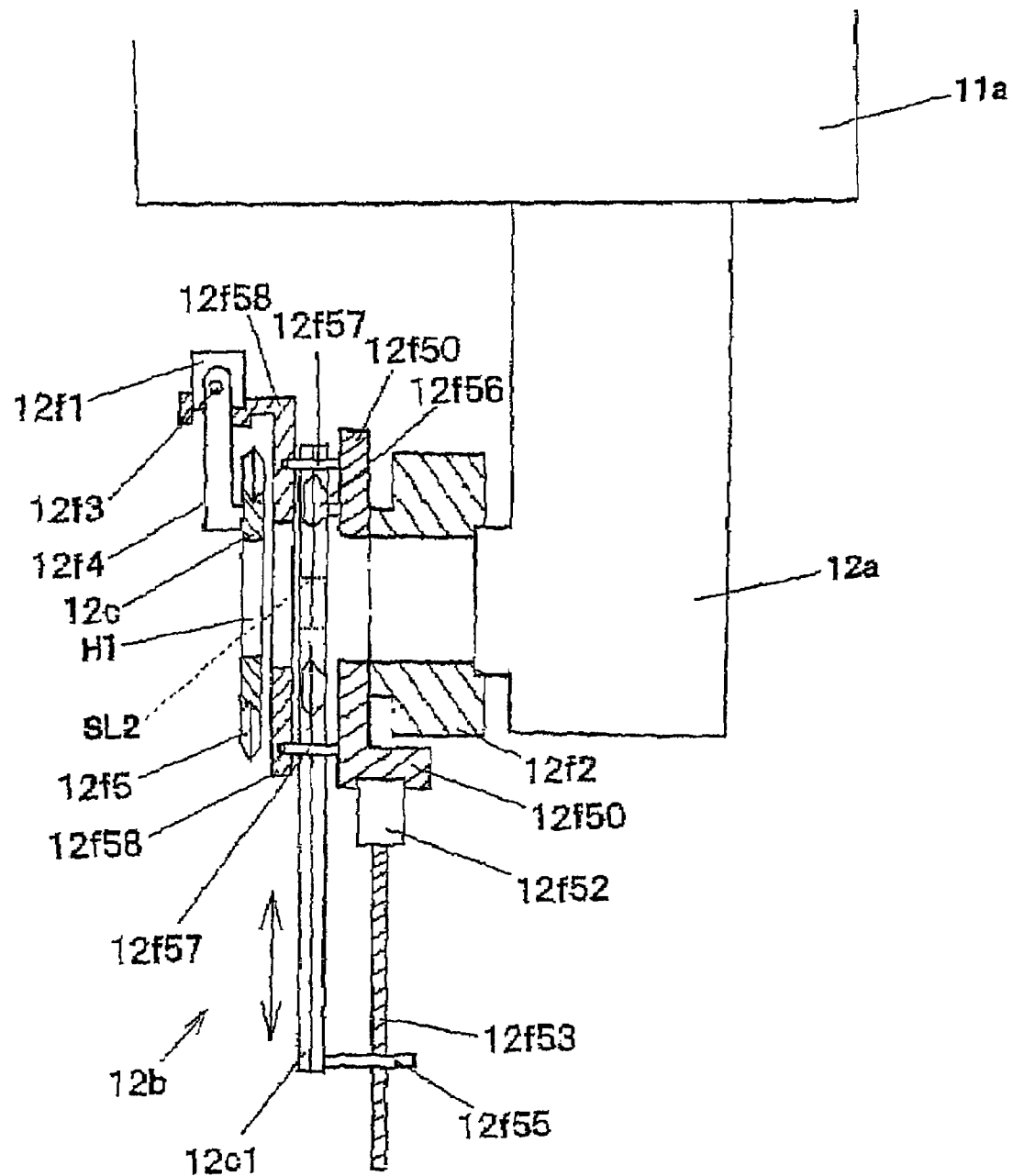
FIG. 24 is a longitudinal sectional view to explain another configuration of the X-ray generating section.

As for an orbit in panoramic radiography, it is possible to employ a configuration of a known panoramic radiography apparatus for moving an X-ray detector and an X-ray generator so as to draw an envelope curve orbit of a substantially triangle which is horizontally symmetrical across a protruding top of a moving orbit of an X-ray slit beam directed toward a front teeth portion of a dental arch as shown in FIG. 24.

Figure 8:
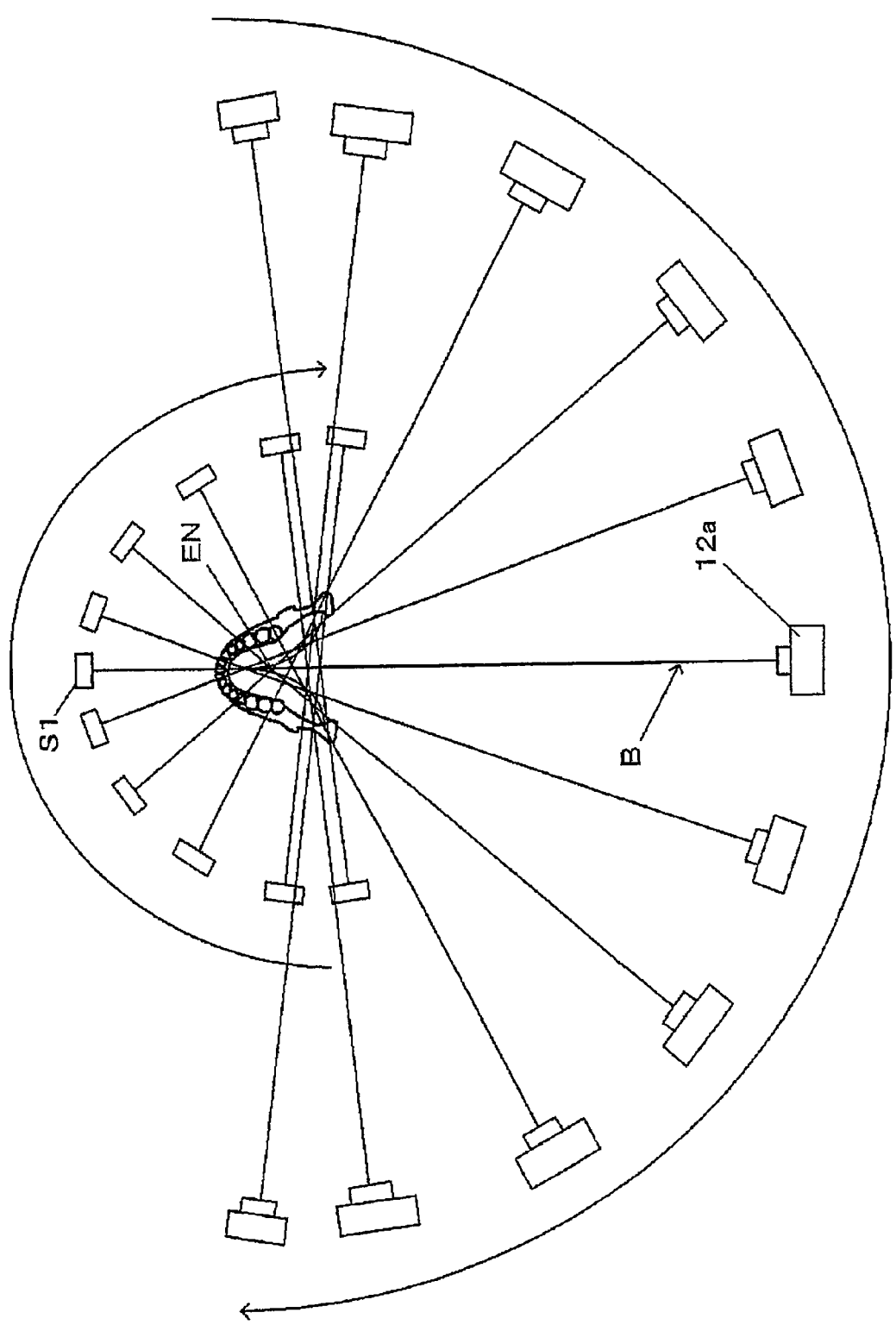
FIG. 8 is a diagram to explain an envelope curve of an orbit of an X-ray slit beam.

FIG. 8 shows a state of an envelope curve EN drawn by an orbit of the X-ray slit beam B which is irradiated from the X-ray generator 12*a* toward the first imaging means S1 at this time. The envelope curve EN is formed by the orbit of the X-ray slit beam B in a combination of rotation of the X-ray generator 12*a* and rotation of the first imaging means S1 due to rotation of the supporting means 11*a*, and movement of the rotary shaft A of the supporting means 11*a*.

Figure 9:
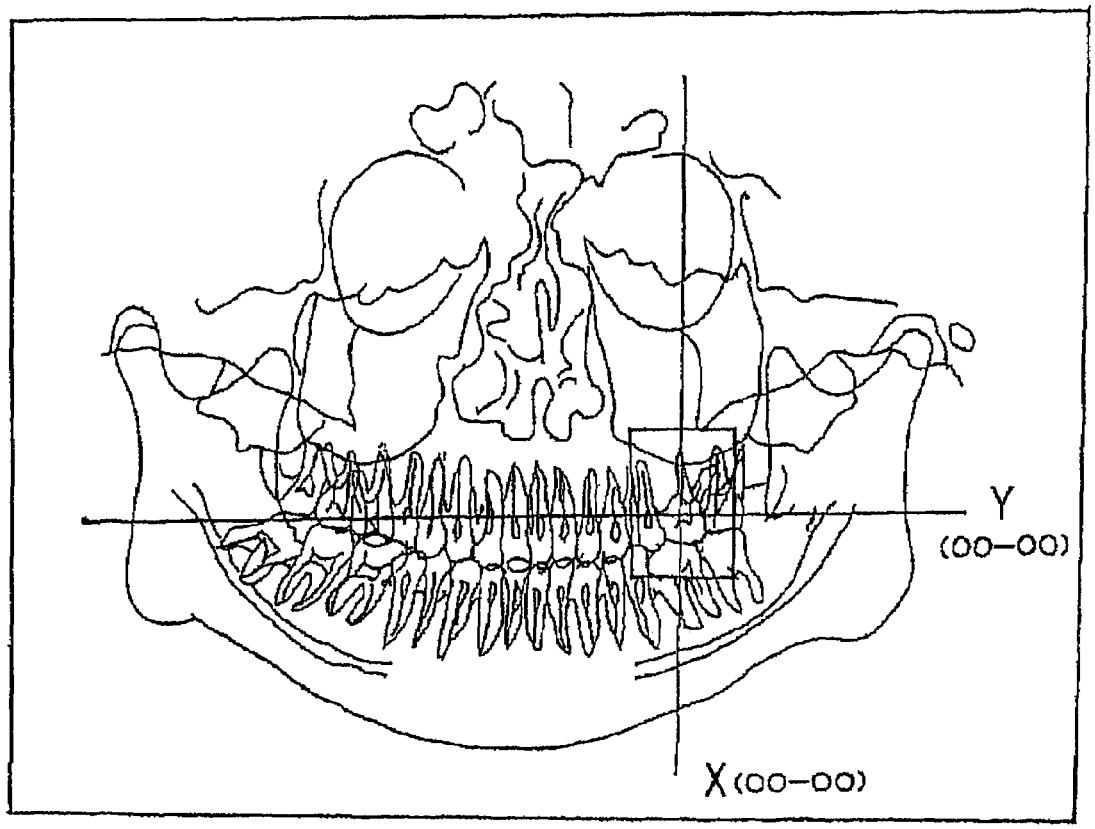
FIG. 9 shows a panoramic image example.

FIG. 9 shows a panoramic image example, showing a developed image of the object o with a cursor in X and Y axes to specify the interested area R. The cursor is not limited and may be any of an arrow-shaped cursor, cross-shaped cursor, and rectangular cursor to display a frame of an interested area, or a cursor in combination thereof. Due to such a cursor, coordinates of a position of the interested area R can be explicitly designated with respect to two coordinate axes orthogonal on a panoramic image. Coordinates in the vicinity of a central portion of a dental arch thickness may also be automatically designated with respect to one of the coordinate axes in a thickness direction of a panoramic image on the basis of the size of a dental arch image.

Explained next will be examples of radiographic orbits in capturing a linear sectional image or a CT image to become a sectional image in accordance with diagrams. It is also possible to capture a panoramic image as a sectional image.

In panoramic radiography here, the X-ray slit beam B is vertically irradiated to a dental arch being the interested area R set in the object o and segmented transmission images of the dental arch are overlapped one after another in order to obtain one panoramic image, where transmission images captured from microscopically different angles are overlapped, so that classification as a sectional image is applied. That is, a panoramic image is realized by sequentially overlapping or compositing segmented transmission images so as to emphasize a cross section of a dental arch.

Moreover, in linear sectional radiography, the object o is irradiated with the X-ray broad beam BB at different projection angles to capture transmission images of the object o, and these transmission images are deviated so as to emphasize only a predetermined sectional plane, so that a sectional image is obtained. As for a radiography position, a plurality of points having different projection angles on a radiographic orbit are contained. It is also possible to capture a linear sectional image by using the X-ray slit beam B.

Figure 10A:
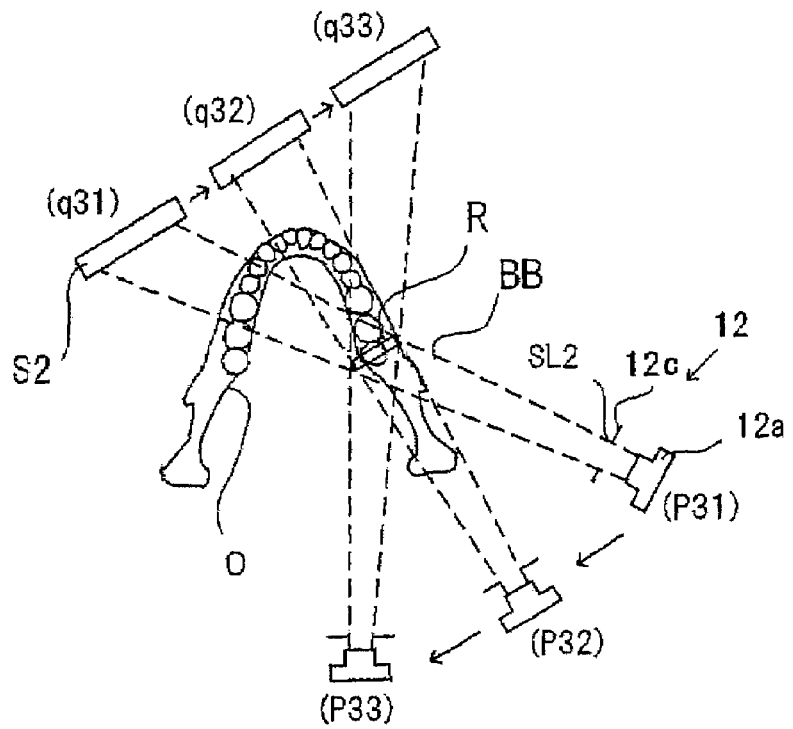
FIGS. 10a and 10b are plane views to explain mutually different radiographic orbits in capturing a linear sectional image.

FIG. 10*a* is a plane view to explain radiographic orbits on which the X-ray generating section 12 and the X-ray detecting section 13 are moved synchronously when capturing a linear sectional image as a sectional image. A sectional plane is set here as the interested area R of the object o.

Figure 10B:
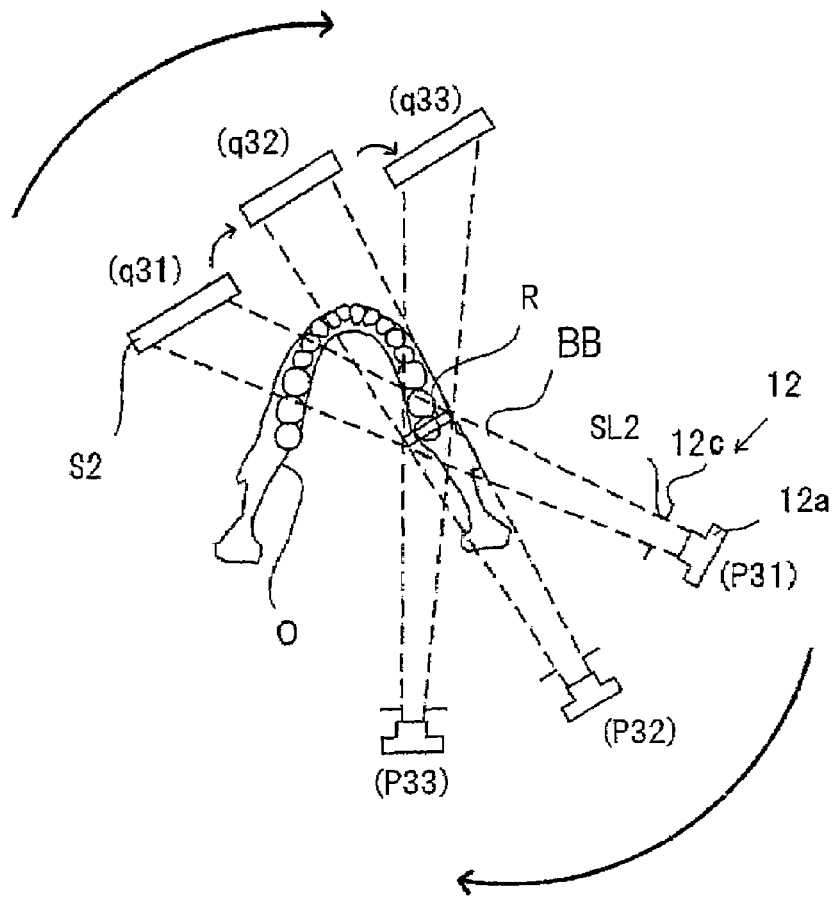

FIG. 10b shows the orbits of movement of the X-ray generating section 12 and the X-ray detecting section 13, which differ from those of FIG. 10a. That is, the X-ray generating section 12 and the X-ray detecting section 13 are rectilinearly moved in mutually different directions in the orbit of FIG. 10a, whereas the X-ray generating, section 12 and the X-ray detecting section 13 exhibit circular arc movement in mutually different directions in the orbit of FIG. 10b.

In this case, the orbit control means 16f causes the X-ray generating section 12 for irradiating the X-ray broad beam BB to move along a radiographic orbit from a position (p31) to a position (p33) by controlling the moving means 11, and causes the second imaging means S2 of the X-ray detecting section 13 to move synchronously along the radiographic orbit from a position (q31) to a position (q33). Transmission images obtained by such radiography along the radiographic orbits are subjected to image processing to exclusively overlap and emphasize portions of the interested area R being an objective sectional plane, so that composition of linear sectional plane images can be achieved.

Meanwhile, in CT image capturing, the X-ray broad beam BB is rotated by at least 180 degrees or more by using the interested area R as a center so as to always include the interested area R set in the object o, and backprojected images of a plurality of transmission images captured at each predetermined rotation angle are calculated to obtain sectional images in arbitrary directions.

Figure 11A:
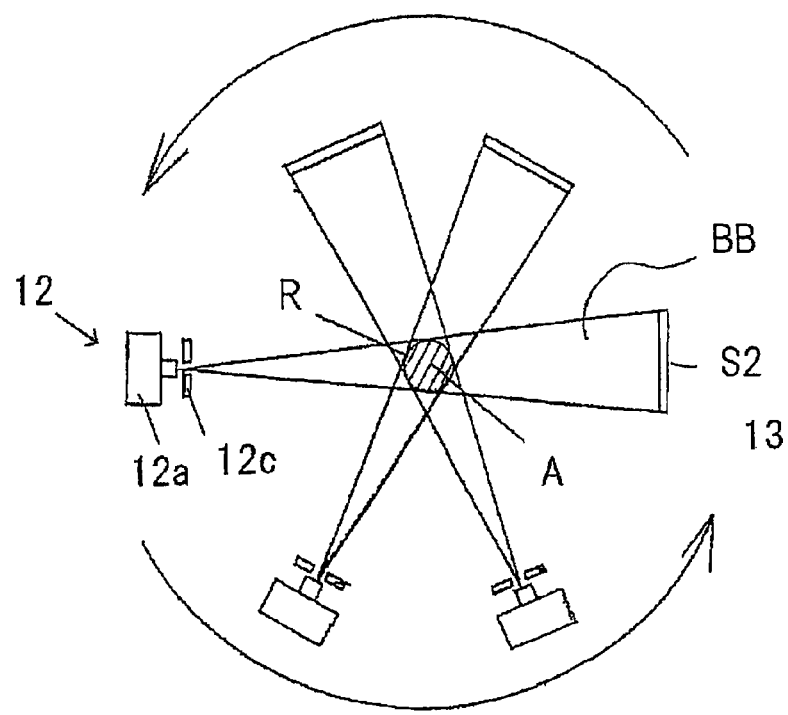
FIG. 11a is a plane view to explain an orbit for normal computed tomography.
Figure 11B:
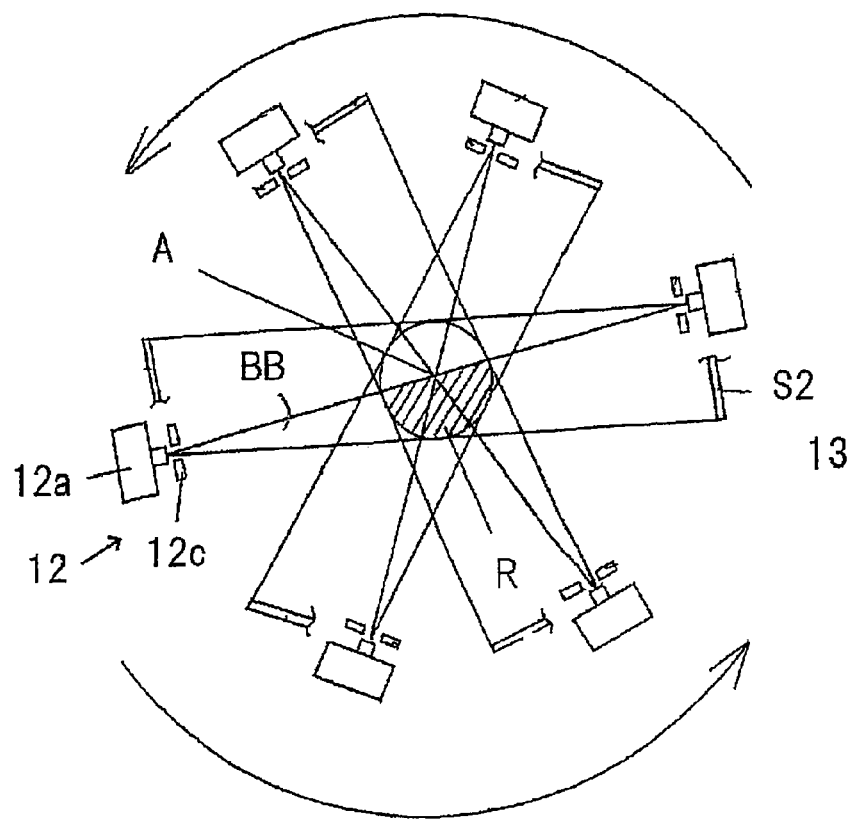
FIG. 11b is a plane view to explain an orbit for offset scan computed tomography.

Here, FIG. 11a shows an orbit for normal computed tomography, and FIG. 11b shows orbit for offset scan computed tomography. In normal computed tomography, the X-ray generator 12a and the second imaging means S2 are turned synchronously for at least half rotation or more in a state that the rotary shaft A positioned to the center of each interested area R is made to be an optical rotary shaft, so that the interested area R is entirely and constantly projected to the second imaging means S2 by the X-ray broad beam BB.

On the other hand, in offset scan computed tomography, the X-ray generator 12a and the second imaging means S2 are turned synchronously for at least one rotation or more in a state that the rotary shaft A positioned to the center of each interested area R is made to be an optical rotary shaft and the second imaging means S2 is offset in front or rear of the turning direction with respect to the X-ray generator 12a and the interested area so that half or more portion of the interested area R is constantly projected to the second imaging means S2. The second imaging means S2 is thus offset in front or rear of a turning direction, namely forward or backward in a turning direction in offset scan computed tomography, where the interested area R is entirely projected while partially and constantly projecting the specified interested area R in order to achieve computed tomography of the interested area R.

Offsetting the second imaging means S2 can be easily realized by, for example, a configuration of moving the supporting means 11a entirely on a plane intersecting the rotary shaft A, or a configuration of adjustably positioning the X-ray detecting section 13 on a plane intersecting the rotary shaft A with respect to the supporting means 11a. Various modifications are possible in the orbit for offset scan computed tomography. Radiography method as stated above is called "offset scan" here.

Figure 12:
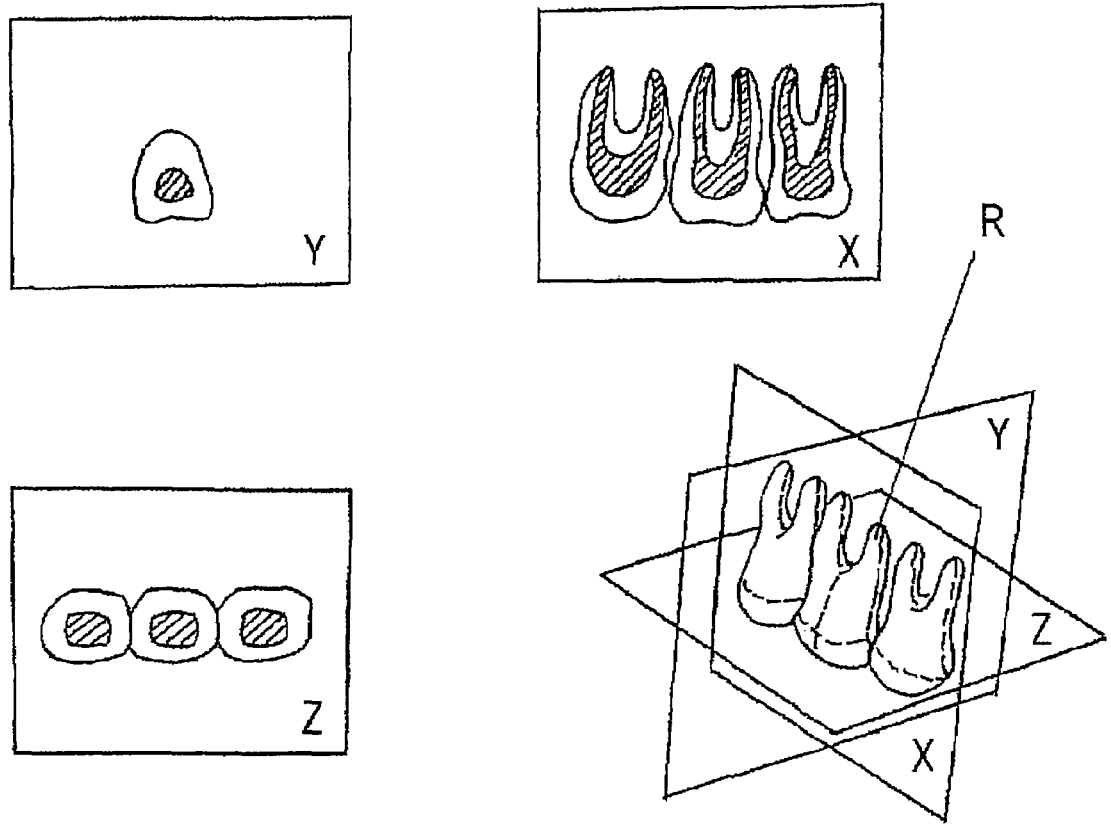
FIG. 12 shows a CT image example.

FIG. 12 shows examples of CT images displayed on the display section 14 after completion of capturing transmission images of the interested area R. In FIG. 12, cross sections orthogonal to an X plane, Y plane and Z plane are applied to the regions of interest R, and sectional images in the respective cross sections are displayed. The regions of interest R can be arbitrarily rotated or moved with respect to these orthogonal cross sections, and sectional images corresponding thereto are reconstructed from captured transmission images.

Figure 13:
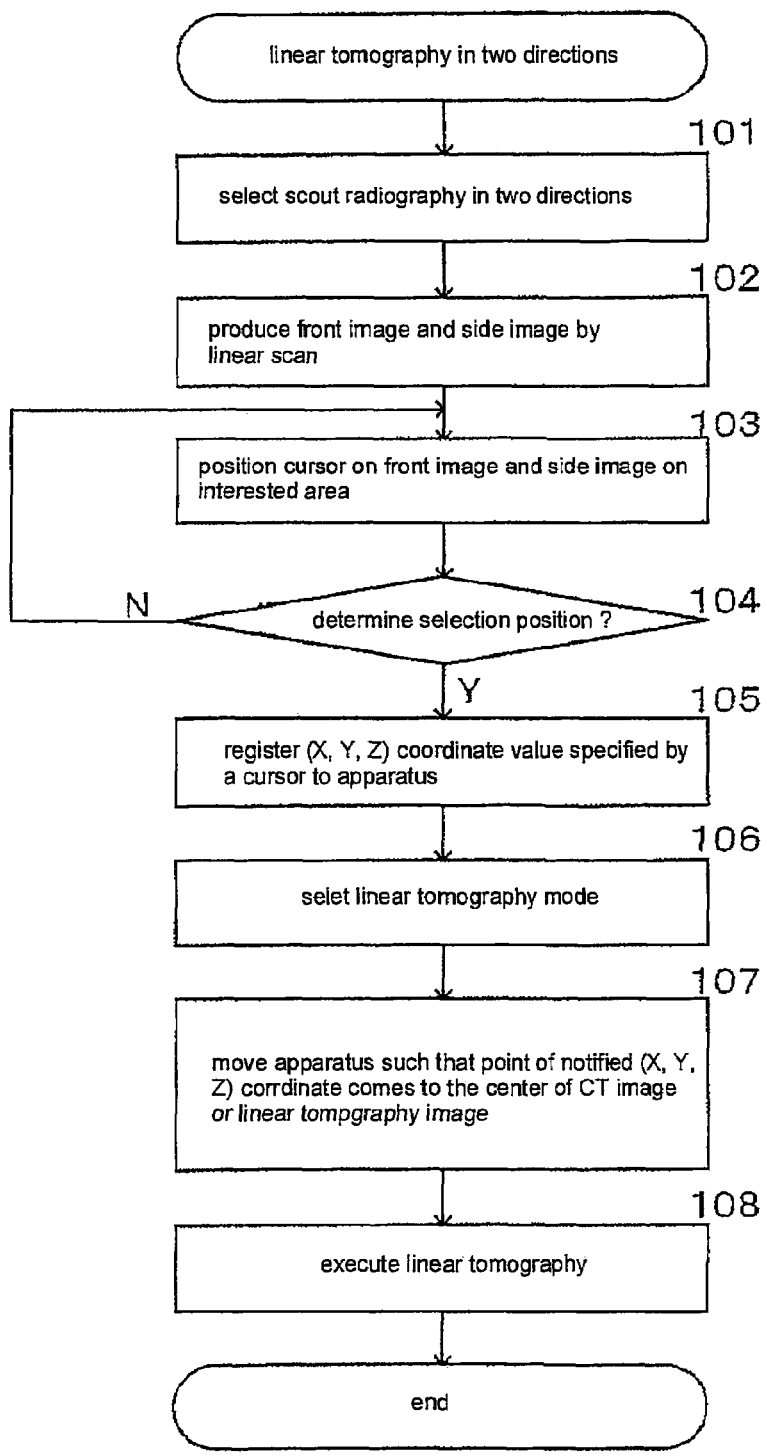
FIG. 13 is a flowchart to explain a basic operation of the radiography apparatus.
Figure 14:
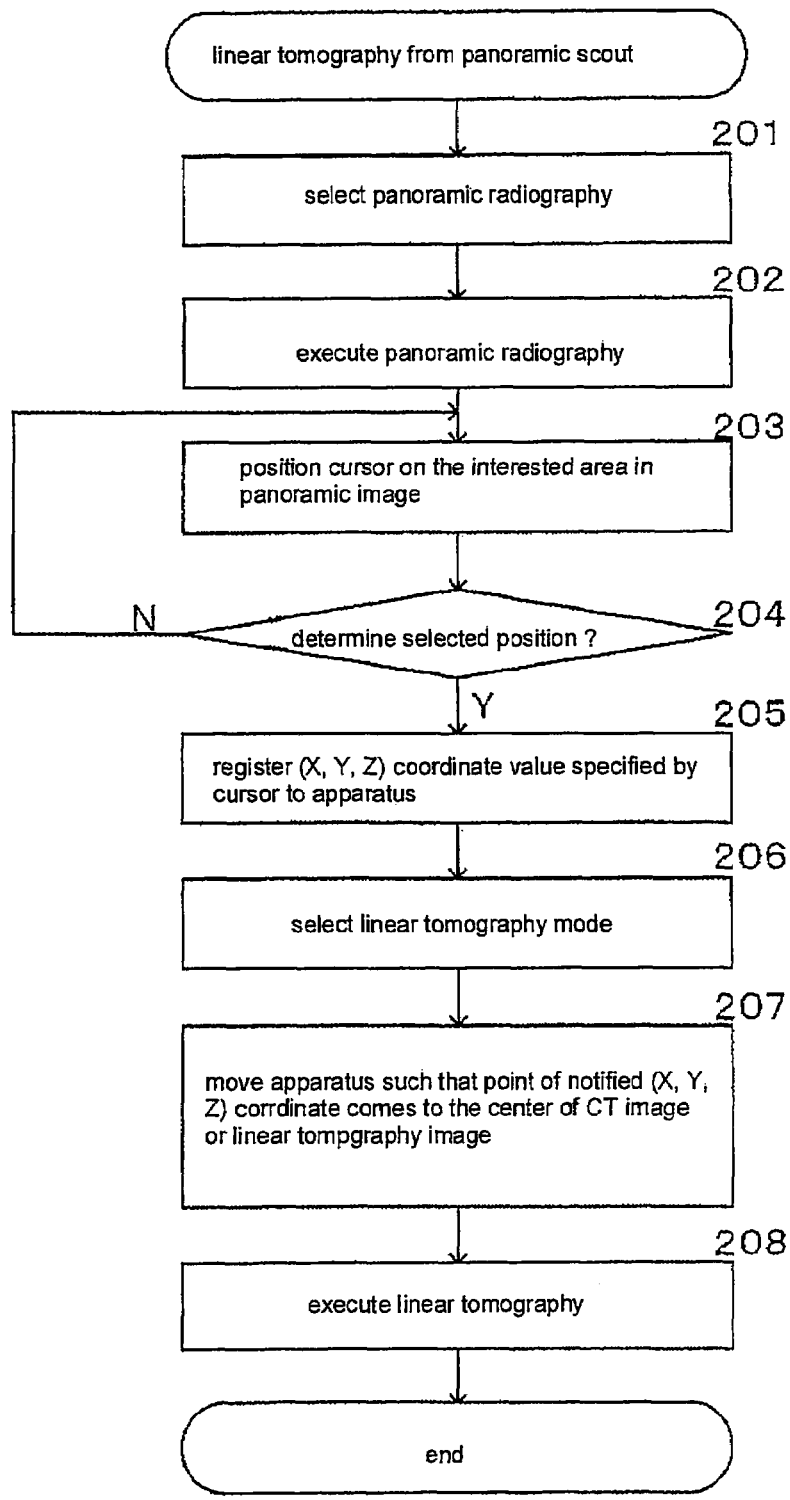
FIG. 14 is a flowchart to explain another basic operation of the radiography apparatus.
Figure 15:
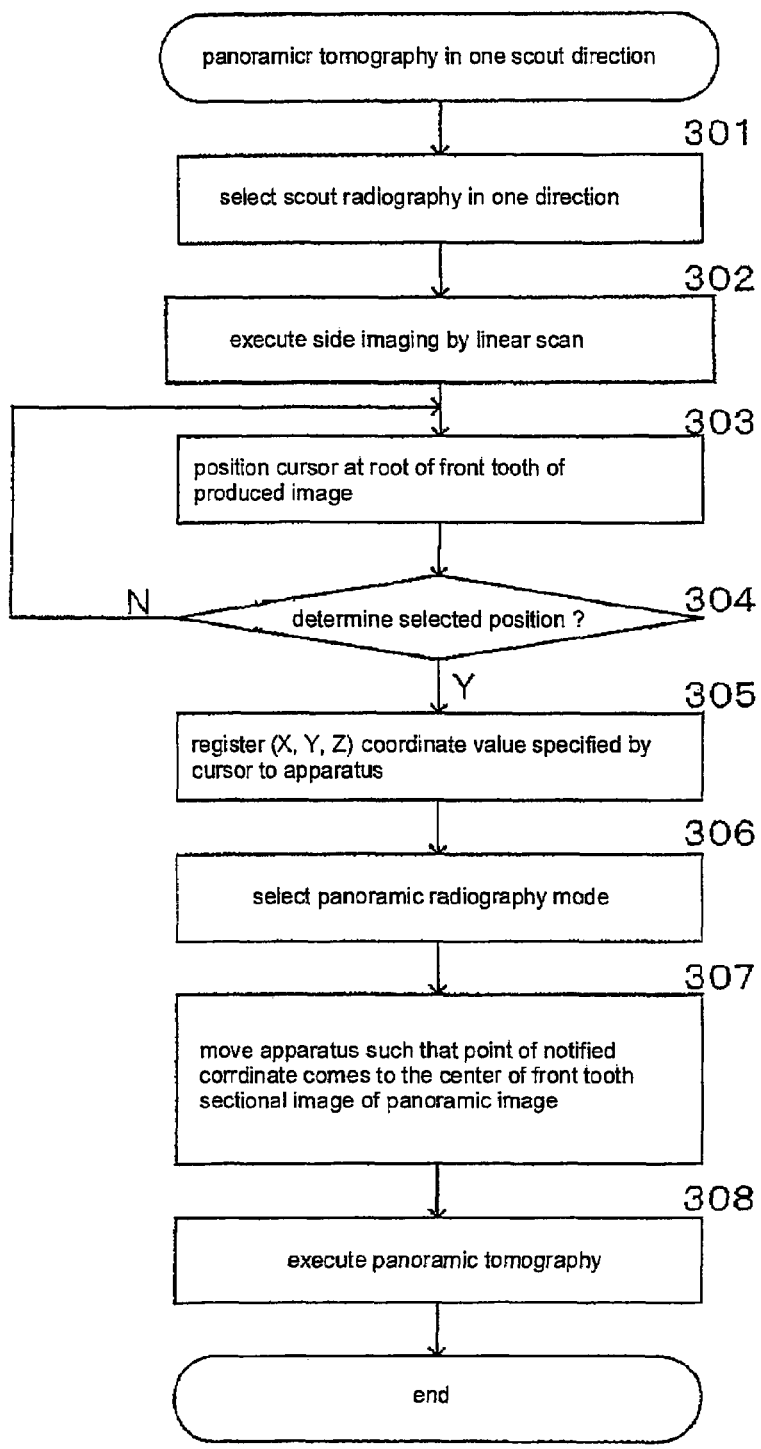
FIG. 15 is a flowchart to explain yet another basic operation of the radiography apparatus.

Next, a series of operations including scout view image capturing, radiography type selection, and sectional image capturing in this radiography apparatus M is shown in flowcharts of FIGS. 13 to 15.

FIG. 13 is a flowchart showing procedures of capturing a linear scan transmission image in two directions as a scout view image (i.e. biplane scout), selecting a linear sectional image by radiography type selection, and capturing a sectional image.

Here, a linear scan transmission image is captured in two directions in steps 101 and 102, the interested area R is selected and a linear sectional image is further selected as a sectional image in steps 103 to 106, and a sectional image is captured in steps 107 to 108.

FIG. 14 is a flowchart showing procedures of capturing a panoramic image as a scout view image, selecting a linear sectional image by radiography type selection, and capturing a sectional image.

Here, a panoramic image is captured in steps 201 and 201, the interested area R is selected and a linear sectional image is further selected as a sectional image in steps 203 to 206, and a sectional image is captured in steps 207 and 208.

FIG. 15 is a flowchart showing procedures of capturing a linear scan transmission image in one direction as a scout view image (i.e. unidirectional scout), selecting a panoramic image by radiography type selection, and capturing a sectional image.

Here, the linear scan transmission image is captured in one direction in steps 301 and 302, the interested area R is selected and a panoramic image is further selected as a sectional image in steps 203 to 306, and a sectional image is captured in steps 307 and 308.

In the radiography apparatus M of this embodiment, the X-ray generating section 12 is allowed to selectively switch and generate the X-ray slit beam B and the X-ray broad beam BB, and the X-ray detecting section 13 is configured to include the longitudinal first imaging means S1 having a small width to capture segmented transmission images of the object o by receiving the X-ray slit beam B, and the second imaging means S2 to capture transmission images of the object o by receiving the X-ray broad beam BB, where a scout view image of the object o captured by the X-ray slit beam B and the first imaging means S1 is used to select the interested area R.

However, ideas of this invention are not limited to the aforementioned configurations, and configurations with following modifications can also be applied. That is, provided is a configuration to include the X-ray generating section 12 allowed to generate the X-ray broad beam BB and the imaging means S2 for capturing a transmission image of the object o by receiving the X-ray broad beam BB, where a scout view images of the object o captured by the X-ray broad beam BB and the imaging means S2 is used to allow selection of the interested area R from the object o. The other component elements are common to those corresponding to the above-mentioned embodiment. In this modified configuration, the X-ray broad beam BB may be differently expanded in scout view image capturing and in tomography of the interested area R.

It is also possible to apply a configuration modified as follows. Namely, provided is a configuration to include the X-ray generating section allowed to generate either the X-ray slit beam B or the X-ray broad beam BB, and the imaging means S2 for capturing segmented transmission images of the object o by receiving the X-ray slit beam B and capturing a transmission image of the object o by receiving the X-ray broad beam BB, where the scout view image of the object o captured by either the X-ray slit beam B or the X-ray broad beam BB and the imaging means S may be used to select the interested area R from the object o. The other component elements are common to those corresponding to the above-mentioned embodiment. The imaging means S2 having a rectangular light receiving section corresponding to the X-ray broad beam BB is used in this configuration, and the light receiving section may be partially used in capturing segmented transmission images of the object o by receiving the X-ray slit beam B.

Moreover, the X-ray generating section 12 and the first and second imaging means S1 and S2 (i.e. X-ray detector and X-ray detecting section) achieves a relative movement with respect to the object o in this embodiment. Accordingly, the X-ray generating section 12 and the imaging means S1 and S2 may be moved by fixing the object o, or the object o may be moved by fixing the X-ray generating section 12 and the imaging means S1 and S2. As stated above, entire movement of the X-ray generating section 12 and the first and second imaging means S1 and S2 with respect to the object is defined relatively in this invention.

If the X-ray generating section 12 and the first and second imaging means S1 and S2 need to be relatively turned (or rotated) with respect to the object o in capturing a sectional image, for example, the X-ray generating section 12 and the first and second imaging means S1 and S2 may be turned while fixing the object o, or the object o may be rotated and moved while fixing the X-ray generating section 12 and the first and second imaging means S1 and S2. Furthermore, the object o may be turned and moved in combination while turning the X-ray generating section 12 and the first and second imaging means S1 and S2. Similar operations are applied other than turning (or rotation).

In the above two configurations, a transmission image of the object o may be used as a scout view image, where panoramic radiography or dual-directional linear scan transmission image radiography in two directions (i.e. simple radiography) may be employed.

FIG. 7 is a chart showing possible combinations of a scout view image and sectional image capturing in the configurations of this invention. A scout view image can be obtained as a longitudinal image with a small width obtained by the first imaging means S1, and as a rectangular image corresponding to the X-ray broad beam BB and obtained by the second imaging means S2. Images obtained by the first imaging means S1 include a linear scan transmission image, a panoramic image, and a cephalometric image, while images corresponding to the X-ray broad beam BB and obtained by the second imaging means S2 include a simple radiographic image, a panoramic image, and a cephalometric image. Sectional image capturing to be selected by the radiography type selection means includes panoramic image capturing, linear sectional image capturing, and computed tomography.

In the case of a configuration of FIG. 51, a transmission image is obtained by the second imaging means S2 according to the system of FIG. 51.

FIG. 7 shows a configuration of possible combinations. In a scout view realized by a linear scan transmission image obtained by the first imaging means S1, a linear scan transmission image may be obtained from only one direction or two directions of the object o when a panoramic image is obtained as an object of sectional image capturing selected by the radiography type selection means.

In the case of obtaining an image from only one direction, an image is specifically obtained from the side of a head portion side of a patient including a dental arch which is the object o. In panoramic radiography, front teeth positioning is important because an image obtained from the side of a head portion side of a patient allows clear understanding of a front teeth position.

In an image obtained by the second imaging means S2 and a scout view image realized by a simple radiographic image, a simple radiographic image may be obtained from only one direction or two directions of the object o when obtaining a panoramic image as a target of sectional image capturing selected by the radiography type selection means. In the case of obtaining an image only from one direction, an image is obtained from the side of a head portion of a patient including a dental arch which is the object o because of a reason similar that of the scout view realized by the linear scan transmission image.

In any sectional image capturing, a scout view image is preferably obtained from two directions of the object 0. Therefore, a three-dimensional position of the interested area R can be understood.

In any invention of this application, one or a plurality of radiography types of a scout view image may be provided, and one or a plurality of radiography types may be provided in a sectional image captured from a scout view.

Image capturing may be realized not only by capturing a scout view image by the first imaging means and a sectional image by the second imaging means, but also by capturing a scout view image by the second imaging means and a sectional image by the first imaging means, and also a scout view image may be captured by the first imaging means and a sectional image may be captured by the first imaging means.

Moreover, a scout view image may be captured by the second imaging means and a sectional image may be captured by the second imaging means. Furthermore, these combinations may be duplicated, and combinations can be freely set.

That is, the example of capturing a scout view image by the first imaging means and capturing a sectional image by the second imaging means is configured by, for example, using the first imaging means to turn a panoramic image, cephalometric image and linear scan transmission image into a scout view image and using the second imaging means to capture a CT image as a sectional image.

Furthermore, the example of capturing a scout view image by the second imaging means and capturing a sectional image by the first imaging means is configured by, for example, using the second imaging means to turn a simple radiographic image into a scout view image and using the first imaging means to capture a panoramic image as a sectional image.

The example of capturing a scout view image by the first imaging means and capturing a sectional image by the first imaging means is configured by, for example, using the first imaging means to turn a linear scan transmission image or a cephalometric image into a scout view image and using the first imaging means to capture a panoramic image as a sectional image.

An example of capturing a scout view image by the second imaging means and capturing a sectional image by the second imaging means is configured by, for example, using the second imaging means to turn a simple radiographic image into a scout view image and using the second imaging means to capture a CT image or a linear tomography image as a sectional image.

In these examples of duplicated combinations, the example of capturing a scout view image by the first imaging means and capturing a sectional image by the second imaging means is configured by, for example, using the first imaging means to turn a panoramic image, a cephalometric images and a linear scan transmission images into a scout view and using the second imaging means to capture a CT image as a sectional image, where further provided is a configuration that a simple radiographic image can be turned into a scout view image by using the second imaging means and a panoramic image can be captured as a sectional image by using the first imaging means.

Although further complicated combinations will not be explained, various combinations are possible between a scout view and a tomography in FIG. 7.

It is also possible to obtain a panoramic image of a temporomandibular joint by using a panoramic view of an entire jaw as a scout view image. Panoramic image capturing of an entire jaw is generally realized by capturing a sectional plane NP disposed along a substantially central dental arch as a center as shown in FIG. 52a, while panoramic image capturing of a temporomandibular joint is generally realized by capturing a sectional plane JP with temporomandibular joint as a center as shown in FIG. 52b. A panoramic image used in this application simply refers to a panoramic image of an entire jaw without any specific classification.

Embodiment 2

Figure 16:
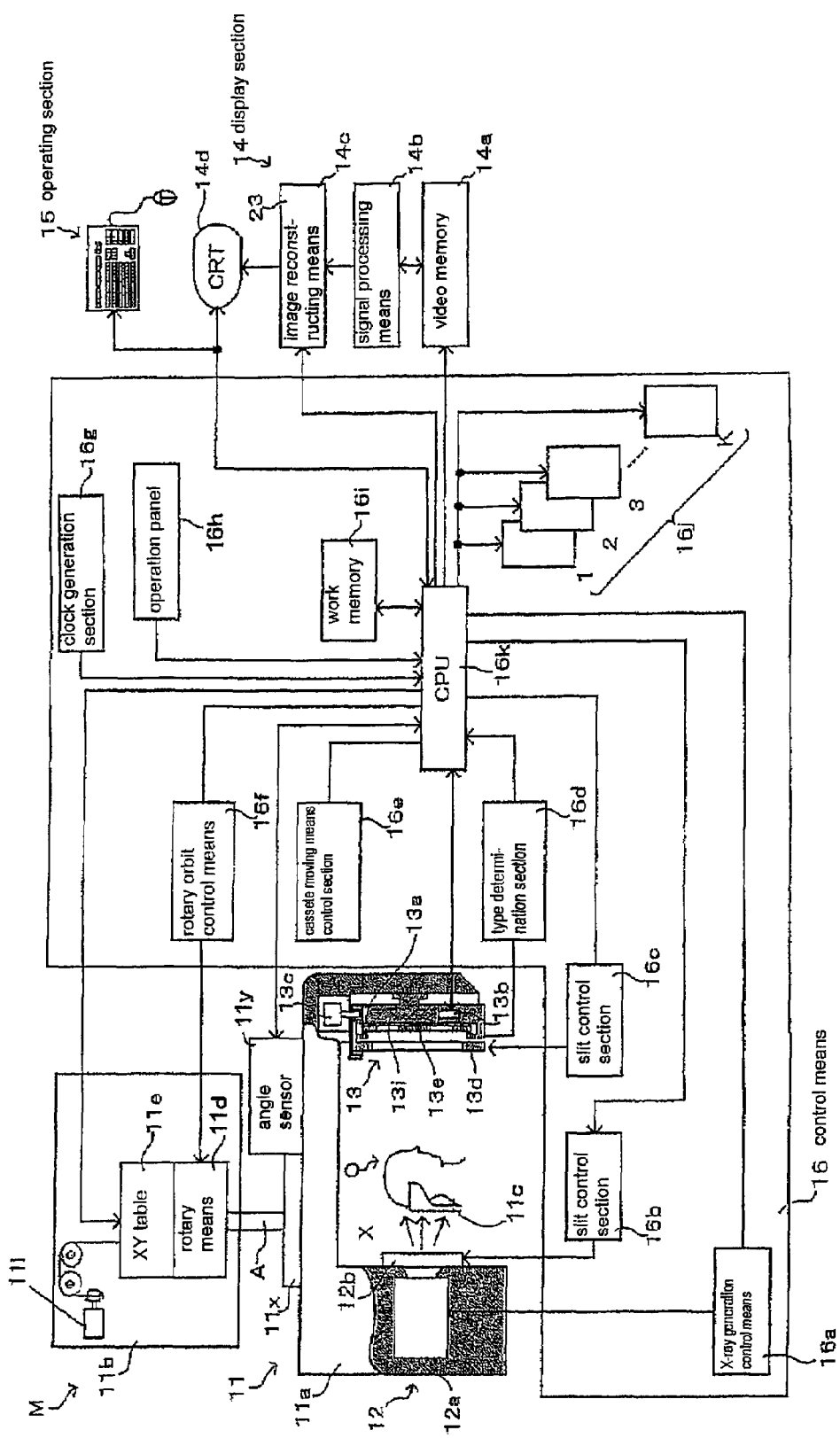
FIG. 16 is a block diagram to explain a schematic configuration of the radiography apparatus in another embodiment.
Figure 17B:
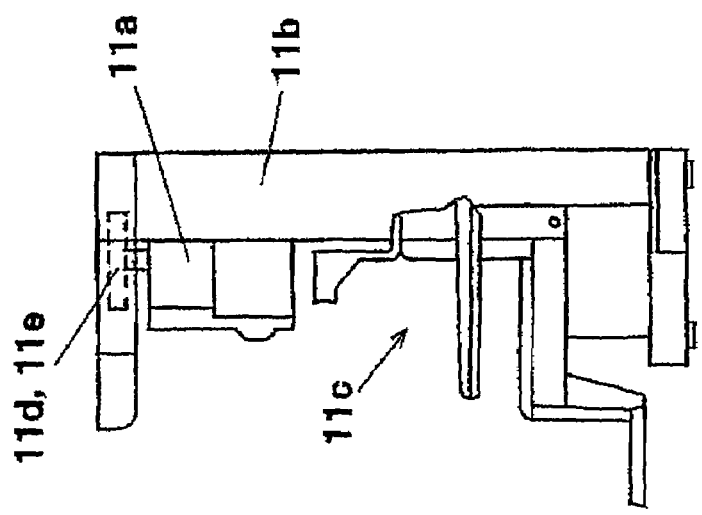
FIGS. 17a and 17b are outline views of the radiography apparatus shown in FIG. 16 to be seen from mutually different directions.
Figure 17A:
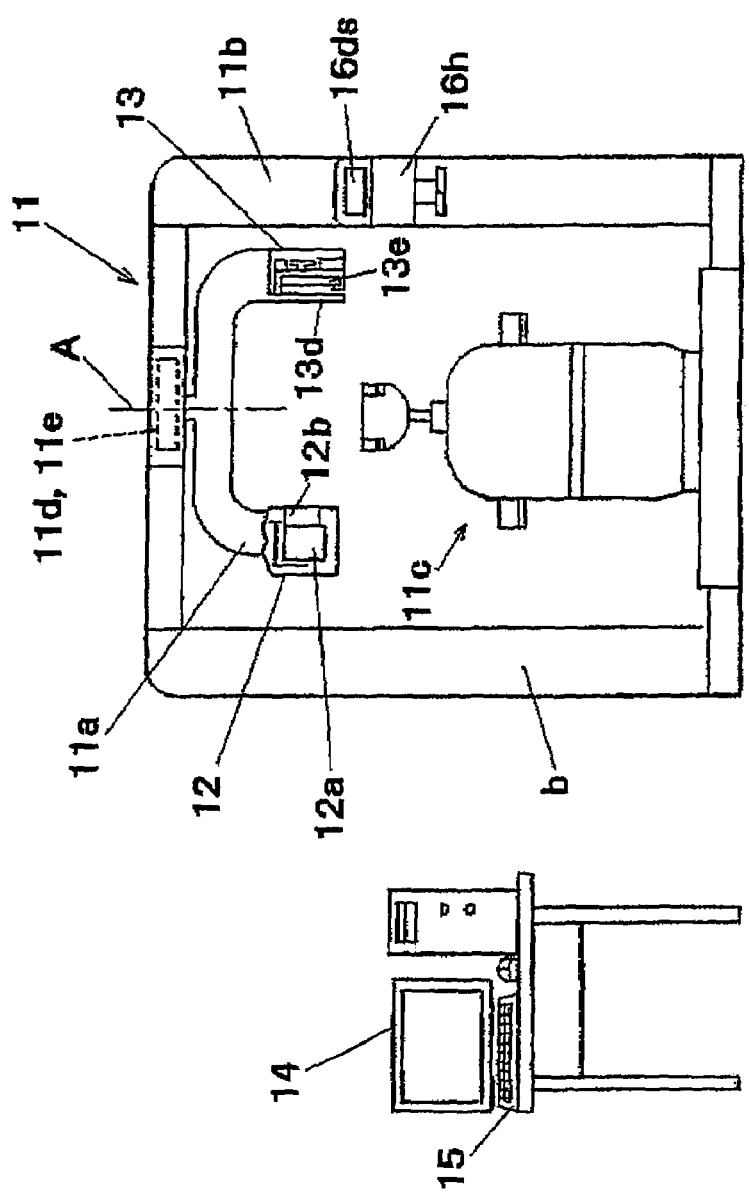
Figure 18:
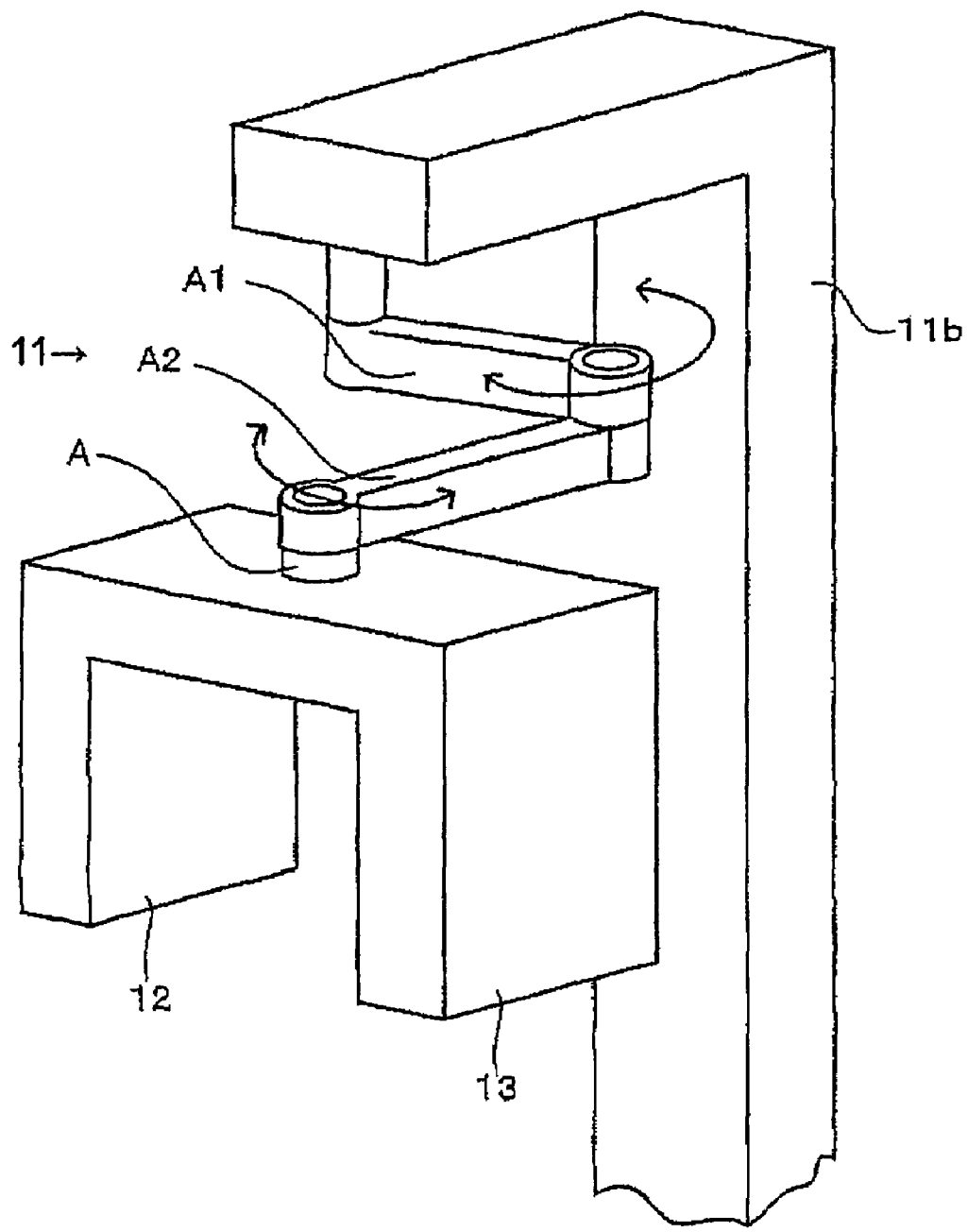
FIG. 18 is a perspective view to explain a different configuration of a moving means.

FIG. 16 is a block diagram to explain a schematic configuration of the radiography apparatus M in another embodiment, and FIGS. 17a and 17b are outline views obtained when the radiography apparatus M is seen from front and side surfaces.

The radiography apparatus M is configured by the moving means 11 for moving the X-ray generating section 12 and the X-ray detecting section 13 which are supported by the supporting means 11a by facing to each other, relative to the object o held by the object holding means 11c, the display section 14 composed of a workstation and a personal computer and the like, the operating section 15, and the control means 16 for controlling the apparatus M, where the moving means 16 is operated to capture an X-ray image of the object o.

The supporting means 11a is configured as a rotary arm connected to the rotary shaft A, and an angle sensor 11y for detecting a rotation angle of turning is attached thereto. A connecting section 11x to the rotary shaft A of the supporting means 11a may be replaced with a supporting means moving table which moves the supporting means 11a two-dimensionally on a plane intersecting the rotary shaft A preferably in one direction on an orthogonal plane and the other direction intersecting the one direction, so that a ratio between a distance from the X-ray generating section 12 to the object o and a distance from the object o to the X-ray detecting section 13 can be changed and an expansion ratio can be controlled. Although the rotary arm is used in the supporting means 11a in this embodiment, arbitrary shapes and mechanisms such as a ring shape may be employed without particularly selecting an arm shape. Moreover, not necessarily configured as the single rotary arm, it is possible to realize a configuration that the X-ray generating section 12 and the X-ray detecting section 13 are supported by different members respectively, and the X-ray generating section 12 and the X-ray detecting section 13 are individually moved but can be totally and relatively moved as an optical system with respect to the object o.

The fixing section 11b is provided with the rotating means 11d for rotating the rotary shaft A by a turn control motor (not shown), and an X-Y table 11e for controlling a position of the supporting means 11a on a plane intersecting the rotary shaft A by moving the rotary shaft A of the supporting means 11a in two-dimensional control by an X-axis control motor (not shown) and a Y-axis control motor (not shown).

The two-dimensional control refers to two-dimensional moving control of the supporting means 11a in a plurality of mutually different directions intersecting an axial direction of the rotary shaft A, or preferably in a plurality of mutually different directions orthogonal to the rotary shaft A, which can be realized by, for example, two-dimensional moving control of the rotary shaft A. It is desirable that the rotary shaft A is made by a hollow shaft so that cables to the X-ray generating section 12 and the X-ray detecting section 13 are arranged to pass therethrough and protected.

The object holding means 11c is composed of, for example, a head rest for holding a head portion of a patient who is the object o, a chin rest for putting a chin of a patient, and a chair for a patient to sit and the like, being connected to an elevation means (not shown) provided in the fixed section 11b.

The elevation means (not shown) is provided with a control motor for moving up and down so as to control a position of the object holding means 11c in a direction parallel to the rotary shaft A.

The moving means 11 is thus configured by the X-Y table 11e and the rotating means 11d of the fixed section 11b, the supporting means 11a having the rotary shaft A and the connecting section 11x, and the object holding means 11c. As for respective control motors of the moving means 11, stepping motors and other motors to allow the rotational angle control and rotational speed control are desirably used.

Therefore, the supporting means 11a for supporting the X-ray generating section 12 and the X-ray detecting section 13 by facing to each other is moved by the moving means 11, which results in moving the X-ray generating section 12 and the X-ray detecting section 13 relative to the object o held by the object holding means 11c.

However, the moving means 11 is ideally an aggregate of component elements functioning as making the supporting means 11a move relative to the object o held by the object holding means 11c, and different component elements can be provided in accordance with radiography types and configurations of the radiography apparatus. In the case of linear scanning and cephalometric radiography, for example, the supporting means 11a is not necessarily turned, so that the moving means 11 is configured by the X-Y table 11e of the fixed section 11b, the rotary shaft A, the supporting means 11a having the connecting section 11x, and the object holding means 11c in this case. Moreover, if at least one of the supporting means 11a and the object holding means 11c is subjected to positioning control by three-dimensional control to be described later, for example, the elevation means provided in the fixed section 11b also becomes an element to constitute the moving means 11.

Although the rotary shaft A of the supporting means 11a is two-dimensionally moved by the X-Y table 11e and the object holding means 11c is moved up and down by the elevation means in the configuration of this example as stated above, an elevation means 11l for moving the supporting means 11a up and down may be provided.

The elevation means 11l shown in FIG. 16 is fixed to the X-Y table 11e and uses a motor to drive a wire guided by a pulley. As will be described later, the elevation means of the object holding means 11c may be mounted onto an X-Y table similar to the above one that moves two-dimensionally in a direction intersecting the rotary shaft A, where various combinations can be considered.

That is, basically two methods exist for the moving means 11 to move the supporting means 11a relative to the object o held by the object holding means 11c. One of the methods is to move the supporting means 11a as stated above, and the other method is to move the object holding means 11c. Both the supporting means 11a and the object holding means 11c may also be moved.

Namely, the moving means 11 may be employed in a configuration that the supporting means 11a is moved relative to the object o held by the object holding means 11c which is not moved, or the moving means 11 may also be employed in a configuration that the object o held by the object holding means 11c is moved relative to the supporting means 11a which is not moved. Alternatively, the moving means 11 may also be employed in a configuration that the supporting means 11a and the object holding means 11c are both moved.

In a case of statically holding the object holding means 11c, the object holding means 11c has a function to move the supporting means 11a relative to the object o held by the object holding means 11c by being statistically held relative to the moving supporting means 11a. Accordingly, even if the object holding means 11c is statically held, it remains as an element to constitute the moving means 11.

In a case of moving the object holding means 11c, there is, for example, a method to add an X-Y table mechanism similar to that of the aforementioned X-Y table 11e to the object holding means 11c. In this configuration, the moving means 11 is configured by the rotating means 11d of the fixed section 11b, the rotary shaft A, the supporting means 11a having the connecting section 11x, and the object holding weans 11c using an X-Y table. Such a configuration as described in JP-A-2000-139902 filed by the applicant of the present invention can be appropriately used.

Therefore, this example may be realized in a configuration that, for example, the supporting means 11a is exclusively rotated by fixing a position of the rotary shaft A without providing the X-Y table 11e for moving the rotary shaft A of the supporting means 11a so that the object holding means 11c is moved two-dimensionally by an X-Y table not shown. In this case, an elevation means may be provided only for the supporting means 11a, or an elevation means may be provided only for the object holding means 11c, or an elevation means may be provided for both the supporting means 11a and the object holding means 11c.

JP-A-2000-139902 shows a configuration that a position of the object holding means 11c is controlled two-dimensionally or three-dimensionally by a holding means position adjustment mechanism. JP-A-2000-139902 also shows a configuration that a rotary arm corresponding to the supporting means 11a of this application and the object holding means 11c are both moved, and this configuration can also be appropriately used.

The supporting means 11a can be rotated by the moving means 11, and the rotary shaft A is set in a direction perpendicular to a floor surface as described in the above example. However, a direction of the rotary shaft A can be freely set, and may be configured in a parallel state or may be set at an arbitrary angle. If the rotary shaft A of the supporting means 11a is set in parallel to a floor surface, the object holding means 11c may be configured as a bed on which a patient lies down.

In this application, terms such as parallel and vertical are used on the assumption that the rotary shaft A is set in a direction perpendicular to a floor surface in such a manner as the example for convenience of explanation, where a direction of the rotary shaft A can be freely set so that the terms are not limited to the meaning of parallel and vertical to a floor surface.

Due to the respective configurations as stated above, a positioning control of the supporting means 11a is realized by the aforementioned two-dimensional control such as a control in two directions defined on a plane intersecting the rotary shaft. However, as long as at least one of the supporting means 11a and the object holding means 11c is subjected to two-dimensional positioning control, any configurations may be possible.

Moreover, one end of an arm A1 whose other end is rotatably fixed to the fixed section 11b in a plane intersecting the rotary shaft A may be rotatably joined to one end of another arm A2 on a plane of intersecting the arm A2 with the rotary shaft A by a rotary joint, so as to rotatably join the rotary shaft A to the other end of the arm A2. Moreover, positioning control of at least one of the supporting means 11a and the object holding means 11c may be realized by a three-dimensional control where one more intersecting direction in a plane intersecting the rotary shaft A, or preferably a direction horizontal to the rotary shaft A, is added to the above two-dimensional control such as control in two directions defined on a plane intersecting the rotary shaft A, in addition to the positioning control by the above-mentioned elevation means.

Explained next in detail is characteristic component elements of this embodiment which are the X-ray generating section 12 and the X-ray detecting section 13.

Figure 19:
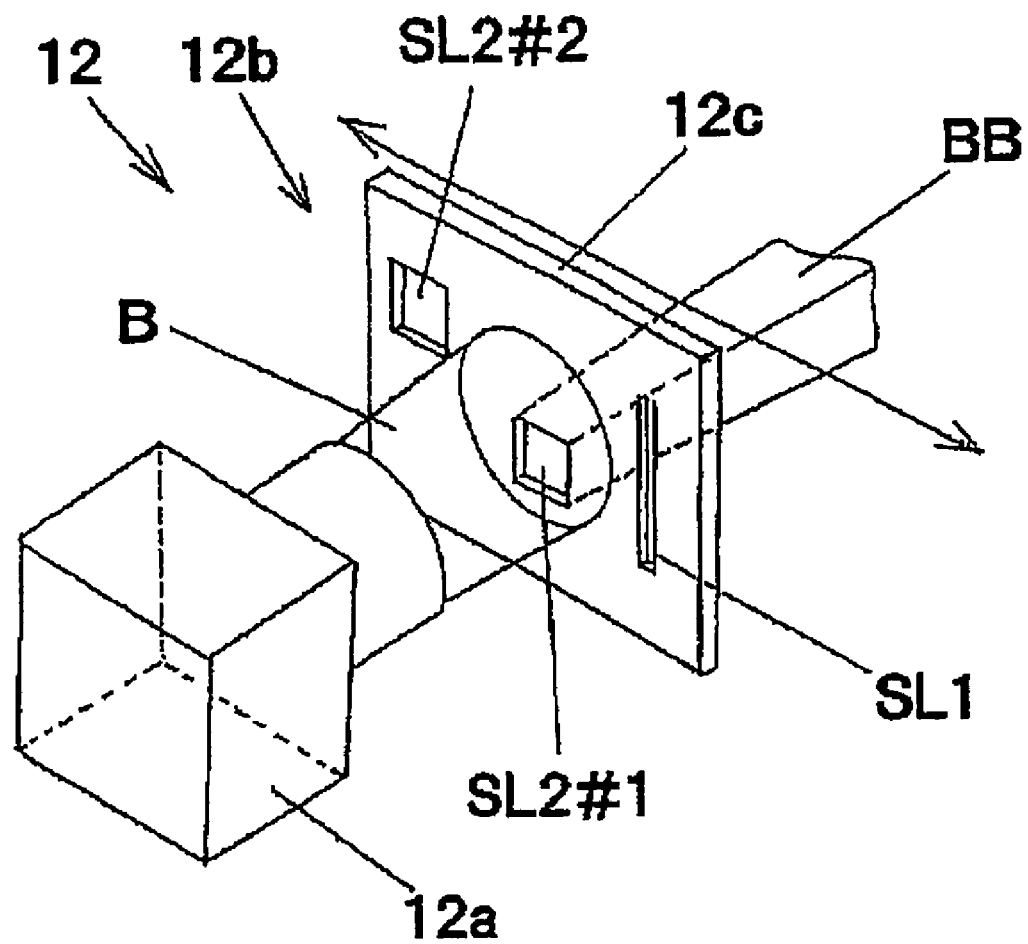
FIG. 19 is a conceptual diagram to explain a different configuration of the X-ray generating section.
Figure 20A:
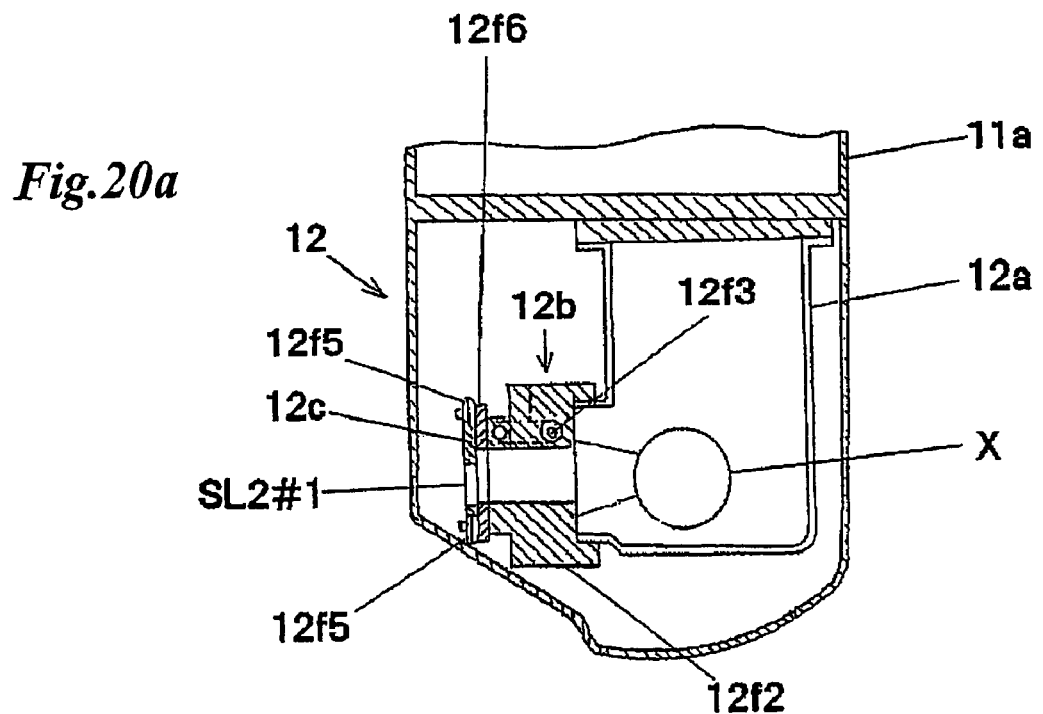
FIGS. 20a and 20b are a cross sectional view and a perspective view to explain a configuration of the X-ray generating section shown in FIG. 19 respectively.
Figure 20B:
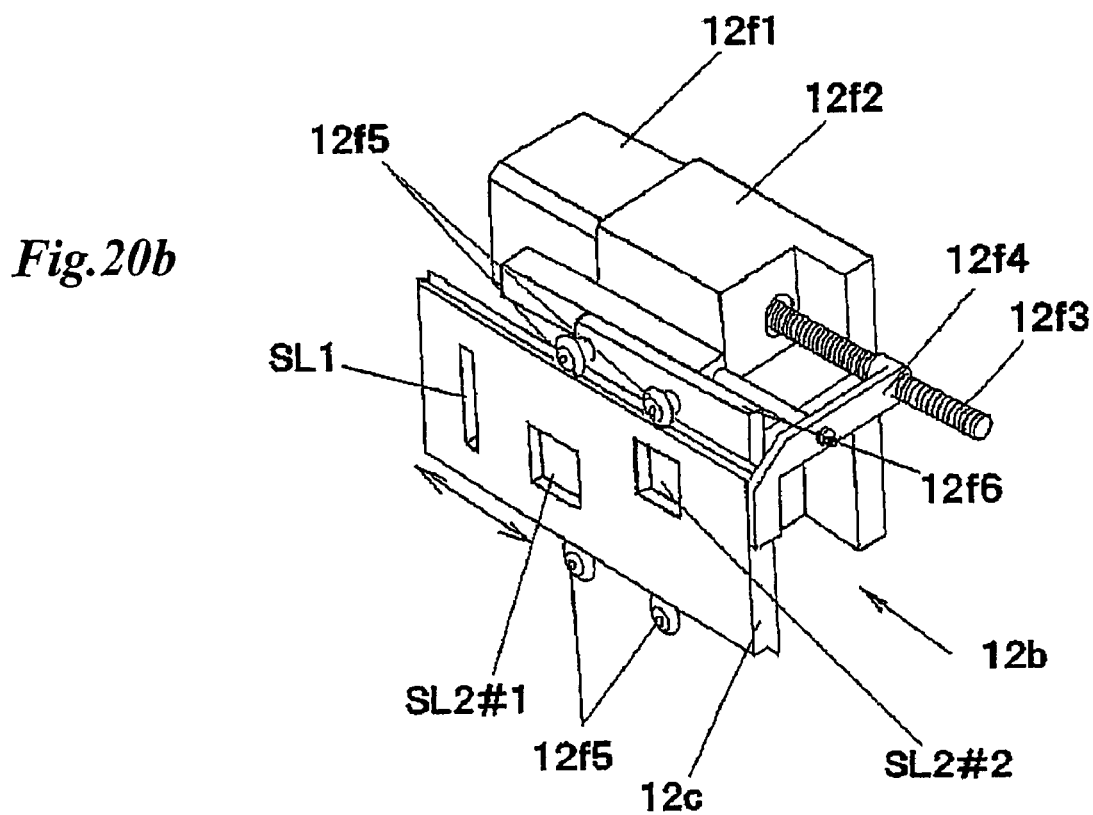

FIG. 19 is a conceptual diagram to explain a configuration of the X-ray generating section 12, and FIGS. 20a and 20b are a cross sectional view and a perspective view showing details of the configuration.

The X-ray generating section 12 here is provided with the X-ray generator 12a for irradiating X-ray beams and the irradiation field changing means 12b for changing the shape of X-ray beams by the narrow grooved slit SL1 and the like, thereby irradiating the X-ray slit beam B or the X-ray broad beam BB being an X-ray cone beam.

To be more specific, the primary slit plate 12c to constitute the irradiation field changing means 12b is arranged in front of an irradiation direction of the X-ray generator 12a for irradiating X-ray beams from an air cooling type X-ray tube X (approx. tube voltage of 90 kV, tube current of 10 mA) in the X-ray generating section 12, where the primary slit plate 12c is allowed to slide between left and right by the motor 12f1. This primary slit plate 12c corresponds to the first imaging means S1, and corresponds to the narrow grooved slit SL1 extending in a direction horizontal to the rotary shaft A, and the second imaging means S2, where two rectangular slits SL2#1 and SL2#2 having different heights in a direction parallel to the rotary shaft A are formed, so that control of an irradiation field can be changed by sliding the slit plate in a direction lateral to X-ray beams. In FIG. 19, an X-ray cone beam is controlled by the rectangular slit SL2#1, showing a state that the X-ray broad beam BB corresponding to the second imaging means S2 is irradiated forward and slightly downward from the X-ray generating section 12.

The rectangular slit SL2#2 is used to control the X-ray broad beam BB corresponding to the second imaging means S2 in the same manner with the rectangular slit SL2#1, and provided in a position higher than the rectangular slit SL2#1 in order to be used to irradiate the X-ray broad beam BB forward and slightly upward. A position of an irradiation field of the X-ray broad beam BB is changed and controlled to a direction horizontal to the rotary shaft A by selecting these rectangular slit SL2#1 and SL2#2 in the irradiation field changing means 12b. The shape of the primary slit plate 12c and the number of the rectangular slit SL2 corresponding to the second imaging means S2 are not particularly limited.

The X-ray generator 12a is fixed to the supporting means 11a in the inside of the X-ray generating section 12. X-ray beams are irradiated from the air cooling type X-ray tube X in the inside of the X-ray generator 12a, and controlled by each of the slits SL1, SL2#1, SL2#2 formed in the primary slit plate 12c provided in the irradiation field changing means 12b provided in front of the X-ray generator 12a so as to be irradiated further forward.

The irradiation field changing means 12b is fixed to the X-ray generator 12a and composed of a fixed block 12f2 having an internal through hole for allowing X-ray beams from the X-ray generator 12a to pass therethrough, the motor 12f1 fixed to the fixed block 12f2, a driven member 12f4 displaced in a direction intersecting X-ray cone beams with respect to the fixed block 12f2 by rotation of a screw shaft 12f3 which is driven to rotate by the motor, a roller fixing plate 12f6 fixed to a front surface of the fixed block 12f2, four rollers 12f5 provided in the roller fixing plate 12f6, and the primary slit plate 12c which is guided by the rollers 12f5, fixed to the driven member 12f4, and displaced in a direction intersecting X-ray beams. Accordingly, the primary slit plate 12c is displaced in a direction across X-ray cone beams by driving and controlling the motor 12f1, so that one of the slits SL1, SL2#1 and SL2#2 can be selected.

Figure 21A:
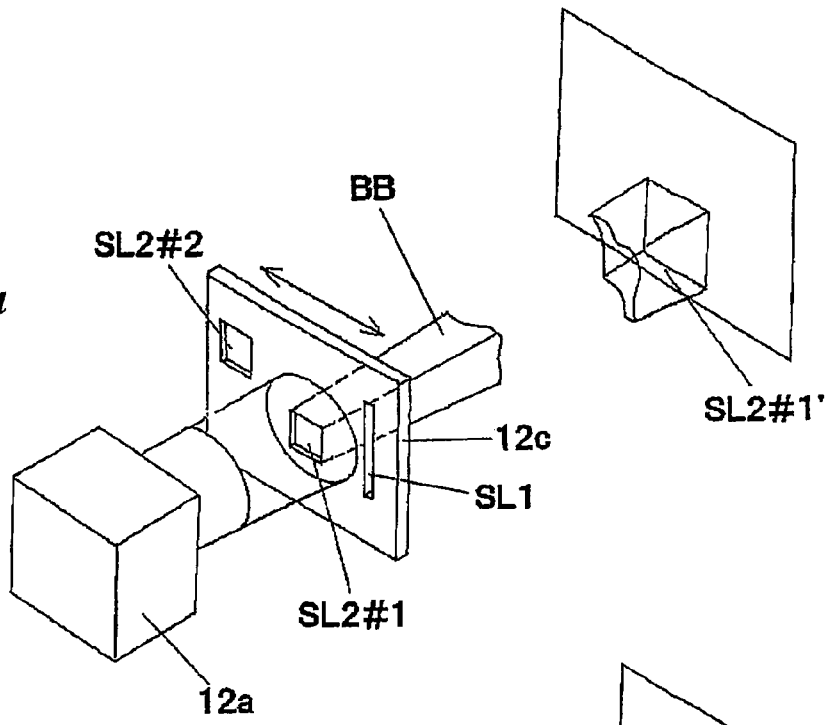
FIGS. 21a and 21b are conceptual diagrams to explain displacement of an X-ray beam irradiation field, each exhibiting a different state.
Figure 21B:
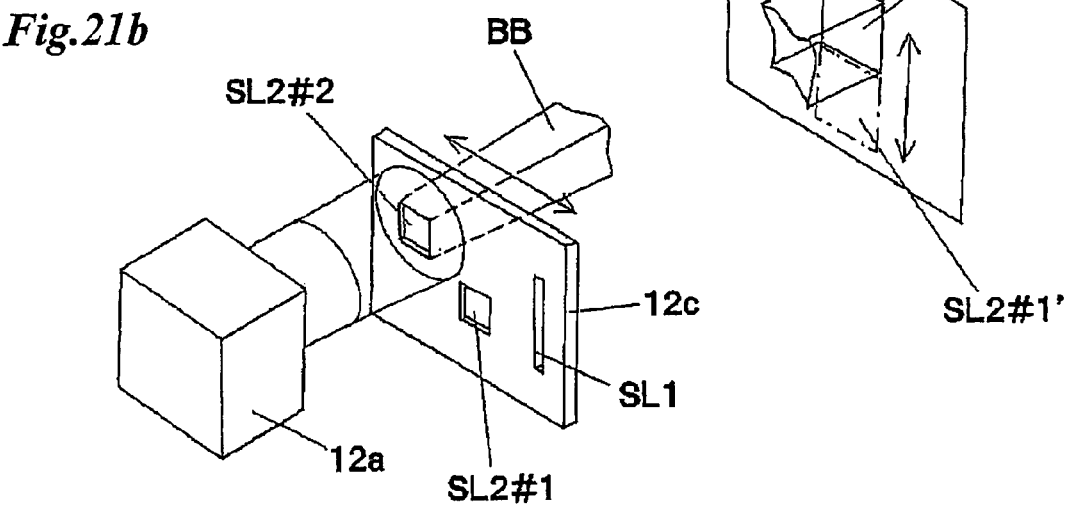

FIGS. 21a and 21b are conceptual diagrams to explain displacement of an X-ray beam irradiation field controlled by the irradiation field changing means 12b. As shown in FIGS. 21a and 21b, an irradiation field of the X-ray slit beam B or the X-ray broad beam BB corresponds to the slits SL1, SL2#1 and SL2#2 selected by the irradiation field changing means 12b, and particularly when either the rectangular slit SL2#1 or SL2#2 is selected, the irradiation field is displaced in a direction parallel to the rotary shaft A with respect to the second imaging means S2.

Figure 22A:
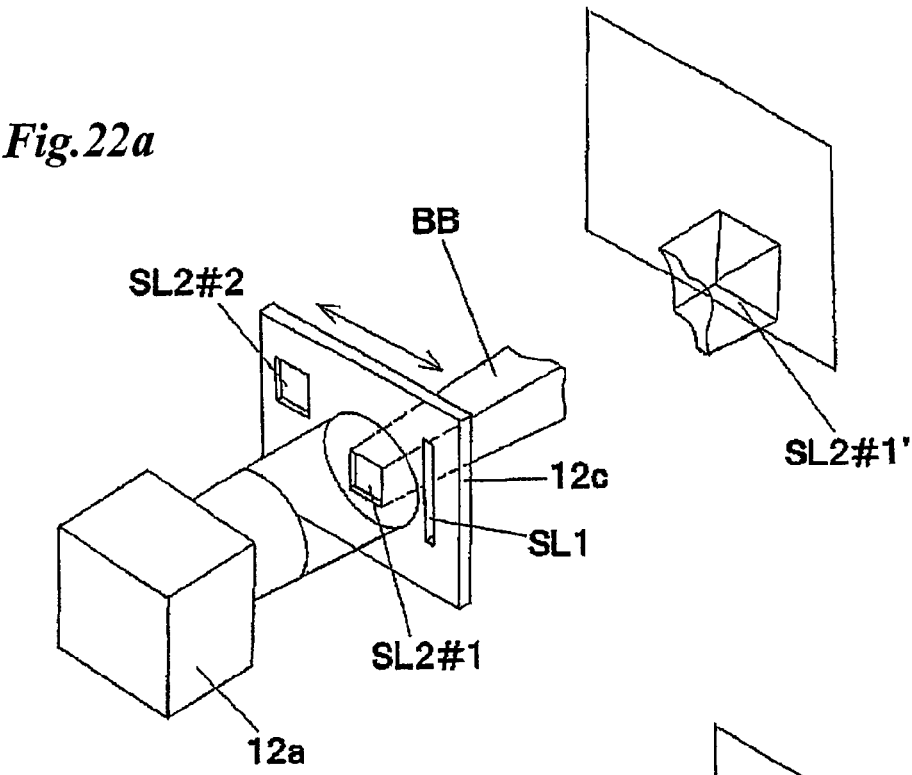
FIGS. 22a and 22b are conceptual diagrams to explain different displacement of the X-ray beam irradiation field, each exhibiting a different state.
Figure 22B:
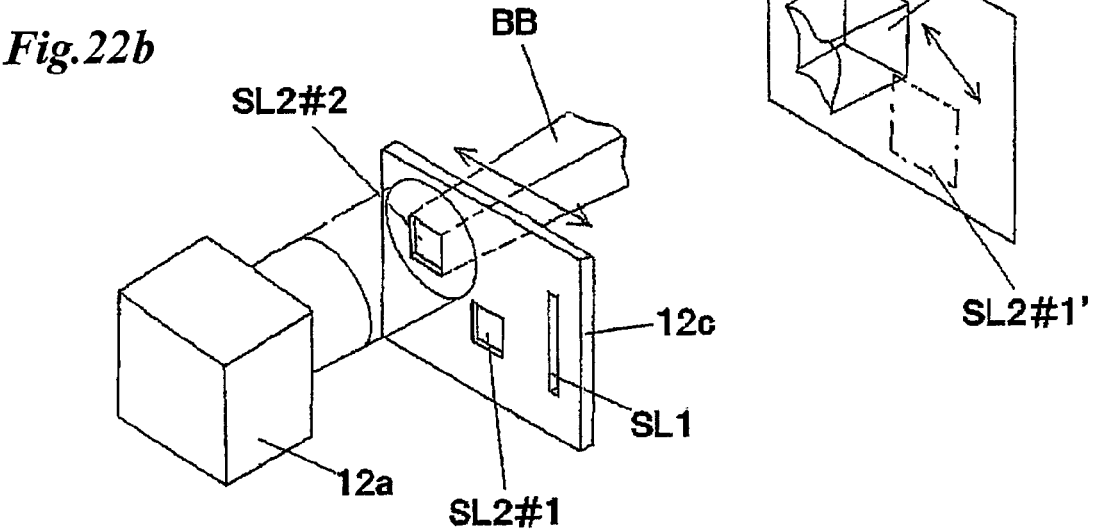

Displacement in a direction parallel to the rotary shaft A does not necessarily mean displacement in a direction which is completely consistent with the rotary shaft A as shown in FIGS. 21a and 21b, and includes displacement in a direction oblique to the rotary shaft A as shown in FIGS. 22a and 22b.

If it is explained more specifically, the X-ray broad beam BB passing through the rectangular slit SL2#1 shown in FIG. 21a is irradiated to an irradiation field SL2#1'. FIG. 21b shows a state that the primary slit plate 12c of FIG. 21a is displaced and the X-ray broad beam BB passing through the rectangular slit SL2#2 is irradiated to an irradiation field SL2#2'. At this time, the irradiation field SL#1' is changed to the irradiation field SL2#2' disposed in a direction completely in parallel with the rotary shaft A.

On the contrary, the X-ray broad beam BB passing through the slit SL2#1 shown in FIG. 22a is irradiated to the irradiation field SL2#1'. FIG. 22b shows a state that the primary slit plate 12c of FIG. 22a is displaced and the X-ray broad beam BB passing through the slit SL2#2 is irradiated to the irradiation field SL2#2'. At this time, the irradiation field SL2#1' is changed to the irradiation field SL2#2' disposed in a vertically oblique direction in FIG. 22b instead of a direction which is completely in parallel with the rotary shaft A.

Such displacement can be easily realized by adjusting a displacement amount of the primary slit plate 12c.

The above example is realized by changing an irradiation field position by displacing the primary slit plate 12c forming a plurality of slits with different heights in a direction parallel to the rotary shaft A, with respect to the X-ray generator 12a, where different systems can be employed.

Each of FIGS. 23a to 23c, FIG. 24, FIG. 25 and FIG. 26 shows a detailed example of the different system which is a modification of FIG. 20, so that explanation of common items will be omitted. In each case of FIGS. 23a to 23c, a stopper member and a movement guide member of the X-ray generator 12a can be easily realized by known mechanisms and thereby they are omitted in FIGS. 23a to 23c.

Figure 23A:
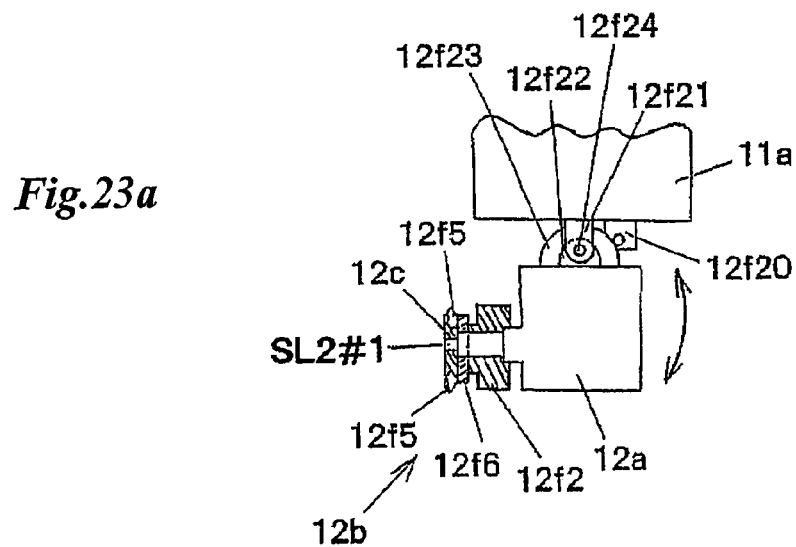
FIGS. 23a to 23c are longitudinal sectional views to explain further different configurations of the X-ray generating section.

FIG. 23a shows an example of changing an irradiation field by rotation of the X-ray generator 12a itself. This example differs from FIG. 20a because the supporting means 11a is not fixed to the X-ray generator 12a. That is, a rotation member 12f22 and a fan-shaped member 12f23 are provided on the top of the X-ray generator 12a, and a supporting member 12f21 is provided at the bottom of the supporting means 11a, where the rotation member 12f22 is joined to the supporting member 12f21 by a rotary shaft 12f24. A motor 12f20 is further provided at the bottom of the supporting member 11a and a driving axis thereof is connected to the fan-shaped member 12f23.

The rotary shaft 12f24 is set in a direction orthogonal to the rotary shaft A and also orthogonal to a direction of X-ray beams from the X-ray generating section 12 toward the X-ray detecting section 13. Accordingly, the X-ray generator 12a is rotated by drive controlling the motor 12f20, so that X-ray beams irradiated from the X-ray generating section 12 to the X-ray detection section 13 can be displaced in a direction parallel to the rotary shaft A.

Figure 23B:
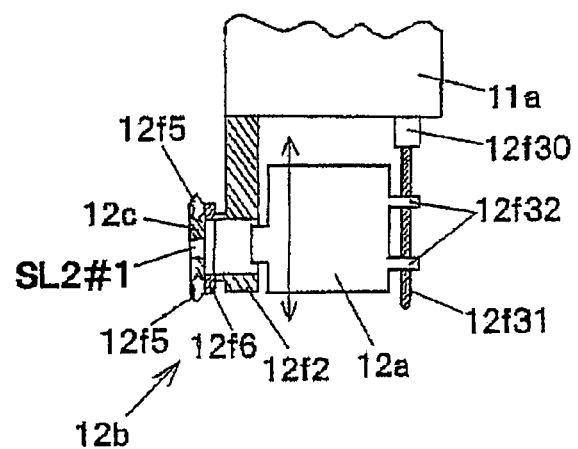

FIG. 23b shows an example of changing an irradiation field by moving the X-ray generator 12a itself up and down with respect to the primary slit plate 12c. The fixed block 12f2 is fixed to a front side of the bottom of the supporting member 11a, which differs from FIG. 23a. The X-ray generator 12a here is not directly fixed to the supporting member 11a, and moved up and down by a driven member 12f32 with respect to the supporting means 11a.

A through hole for allowing X-ray beams inside the fixed block 12f to pass therethrough is set in a size to allow a tip end of the X-ray generator 12a to be moved up and down in a predetermined range. The motor 12f30 is fixed in a rear side of the bottom of the supporting member 11a in a state that a screw shaft 12f31 being a driving shaft is directed downward. A driven member 12f32 which is internally threaded and inserts the screw shaft 12f31 thereinto is provided on a rear surface of the X-ray generator 12a. Accordingly, if the screw shaft 12f31 is driven, the X-ray generator 12a is moved up and down with respect to the fixed block 12f2 and the primary slit plate 12c, so that an irradiation field is vertically changed. That is, X-ray beams irradiated from the X-ray generating section 12 to the X-ray detecting section 13 are displaced by driving the motor 12f30, in a direction parallel to the rotary shaft A.

Figure 23C:
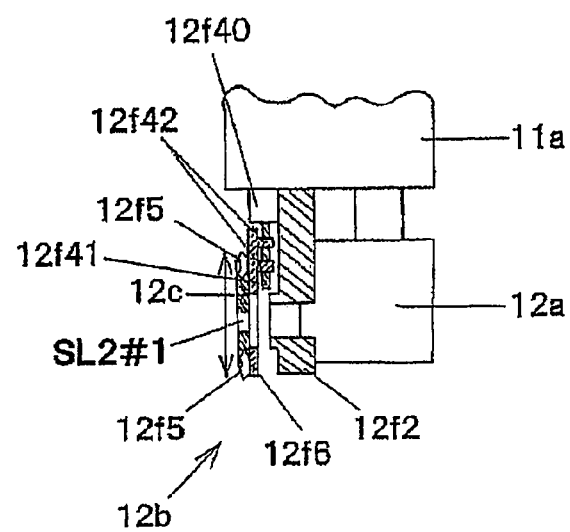

FIG. 23c shows an example of changing an irradiation field by moving the primary slit plate 12c up and down with respect to the X-ray generator 12a. The X-ray generator 12a here is fixed under the supporting means 11a and the fixed block 12f2 is fixed to the X-ray generator 12a. A motor 12f40 is fixed to a front side of the bottom of the supporting means 11a in a state that a screw shaft 12f41 being a driving shaft is directed downward. As being different from FIG. 20b, the roller fixing plate 12f6 is separated from the fixed block 12f2 and configured as an elevation member, where a driven member 12f42 which is internally threaded and inserts the screw shaft 12f41 thereinto is provided on a back surface of the roller fixing plate. Accordingly, if the screw shaft 12f41 is rotated, the primary slit 12c is moved up and down with the roller fixing plate 12f6 and an irradiation field is vertically changed. That is, X-ray beams irradiated from the X-ray generating section 12 to the X-ray detecting section 13 are displaced in a direction parallel to the rotary shaft A by driving control of the motor 12f40.

As stated above, only one rectangular slit SL2 corresponding to the second imaging means may be provided in the respective examples of FIGS. 23a to 23c.

Figure 25:
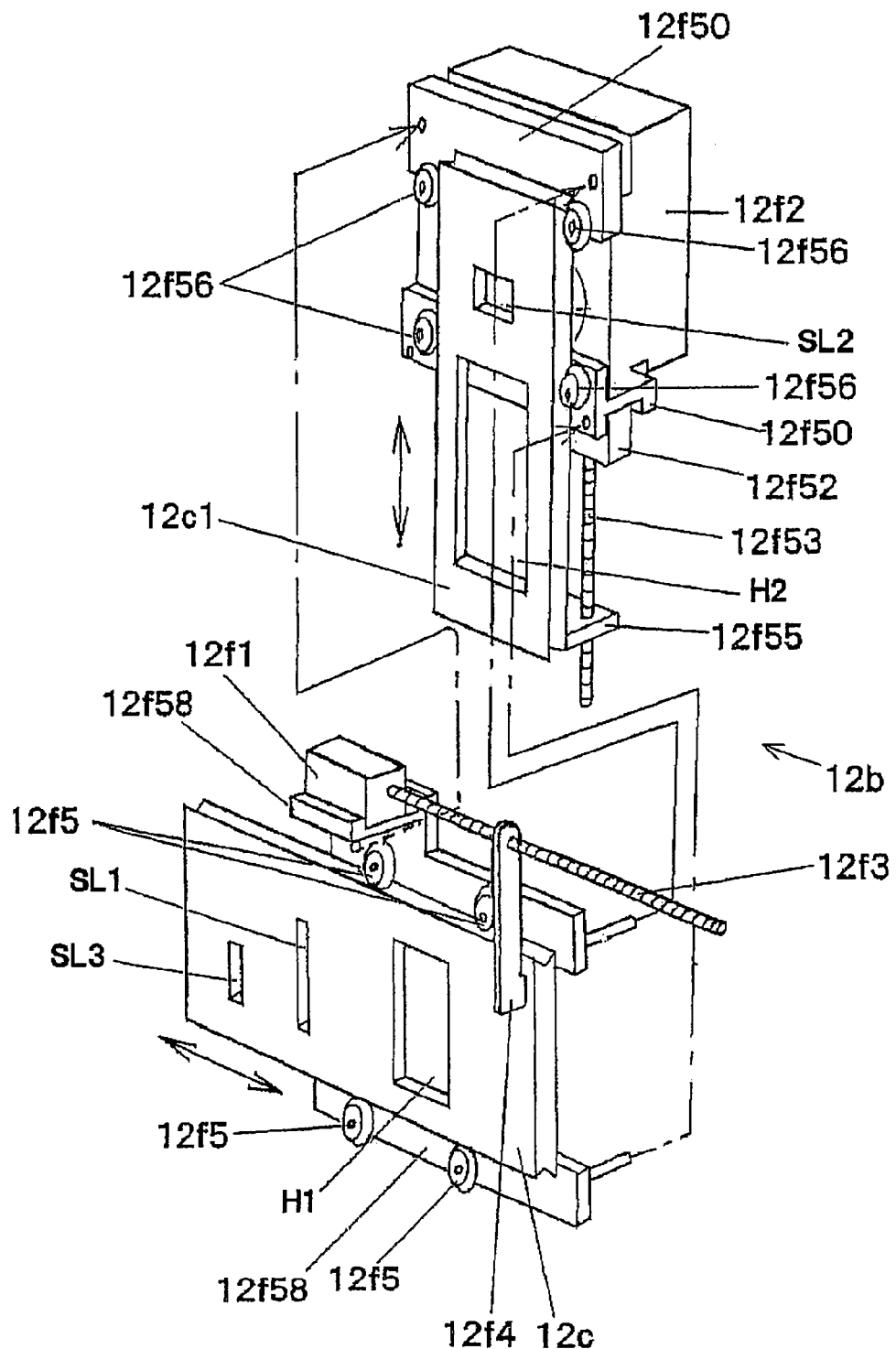
FIG. 25 is a disassembled perspective view of the X-ray generating section shown in FIG. 24.

FIGS. 24 and 25 show examples where the rectangular slit SL2 for controlling X-ray cone beams to correspond to the second imaging means S2 is formed in a slit plate 12c1 which differs from the primary slit plate 12c of FIG. 20b and is displaced in a direction parallel to the rotary shaft A.

Here, FIG. 24 is a longitudinal sectional view to explain such a configuration of the X-ray detecting section 12, and FIG. 25 is a disassembled perspective view of the irradiation field control means 12b. What is meant by a "front plane" in the following explanation is a front plane to be seen from a direction of receiving X-ray beams from the X-ray generator 12a.

In this example, the X-ray generator 12a is fixed to the supporting means 11a, and the fixed block 12/2 having an internal through hole for allowing X-ray beams to pass therethrough is fixed to the X-ray generator 12a. Two roller fixing plates 12/50 are fixed to a front plane of the fixed block 12/2. A motor 12/52 is fixed at the bottom of a roller fixing plate 12/50 on a lower side in a state that a screw shaft 12/53 being a driving shaft is fixed downward. Meanwhile, a driven member 12/55 which is internally threaded and inserts the screw shaft 12/53 thereinto is provided in the slit plate 12c1, and driving control of the motor 12/52 causes the slit plate 12c to be displaced vertically in FIG. 24a, i.e. guided by four rollers 12/56 provided in the two roller fixing plates 12/50 and displaced in a direction parallel to the rotary shaft A. Then, the rectangular slit SL2 corresponding to the second imaging means S2, and an opening section H2 which is widely opened for a purpose to be described later are formed in the slit plate 12c1.

Two roller fixing plates 12/58 are fixed to a front plane of the two roller fixing plates 12/50 by four pins in a form to hold the primary slit plate 12c so as not to interrupt movement thereof. Four rollers 12/5 are arranged in a front plane of the roller fixing plate 12/58. The motor 12/1 is fixed in an upper portion of the roller fixing plate 12/58 on an upper side in a state that the screw shaft 12/3 being a driving shaft is directed sideward. The driven member 12/4 which is internally threaded and inserts the screw shaft 12/3 thereinto is provided in a front plane of the primary slit plate 12c. Accordingly, if driving control of the motor 12/1 is performed, the primary slit plate 12c is guided by the roller 12/5 and displaced in a direction across X-ray cone beams. In this primary slit plate 12c, there are formed the narrow grooved slits SL1 and SL3 corresponding to the first imaging means S1 and extending in a direction parallel to the rotary shaft A, and an opening section H1 which is widely opened for a purpose to be described later. The slit SL1 is a narrow grooved slit for use in panoramic radiography and linear scanning, while the slit SL3 is a narrow grooved slit for use in cephalometric radiography.

Explanation is made here for an irradiation field change which is realized by displacing the slit plate 12c1 by the motor 12/52 so that the rectangular slit SL2 is disposed in a position to control X-ray cone beams in the case of computer tomography. Due to adjustments of a displacement amount, an irradiation field of the X-ray broad beam BB can be changed with respect to the second imaging means S2 in a direction parallel to the rotary shaft A. In this case, the primary slit plate 12c is displaced by the motor 12/1 so that the opening section H1 is disposed in front of the rectangular slit SL2. The opening section H1 is set in a size which does not interrupt the X-ray broad beam BB passing through the rectangular slit SL2.

On the contrary, in a case of panoramic radiography and linear scanning, the primary slit 12c is displaced by the motor 12/1 so that the narrow grooved slit SL1 is disposed in a position to control X-ray cone beams. At this time, since X-ray cone beams which are to pass through the narrow grooved slit-f1 are not interrupted, the slit plate 12c is displaced by the motor 12/52 so that the opening section H2 is disposed behind the narrow grooved slit SL1. The opening section H2 is set in a size which does not interrupt X-ray cone beams supposed to pass through the narrow grooved slit SL1.

In a case of cephalometric radiography, the narrow grooved slit SL1 is simply replaced with the narrow grooved slit SL3, and thereby detailed explanation is omitted.

Figure 26:
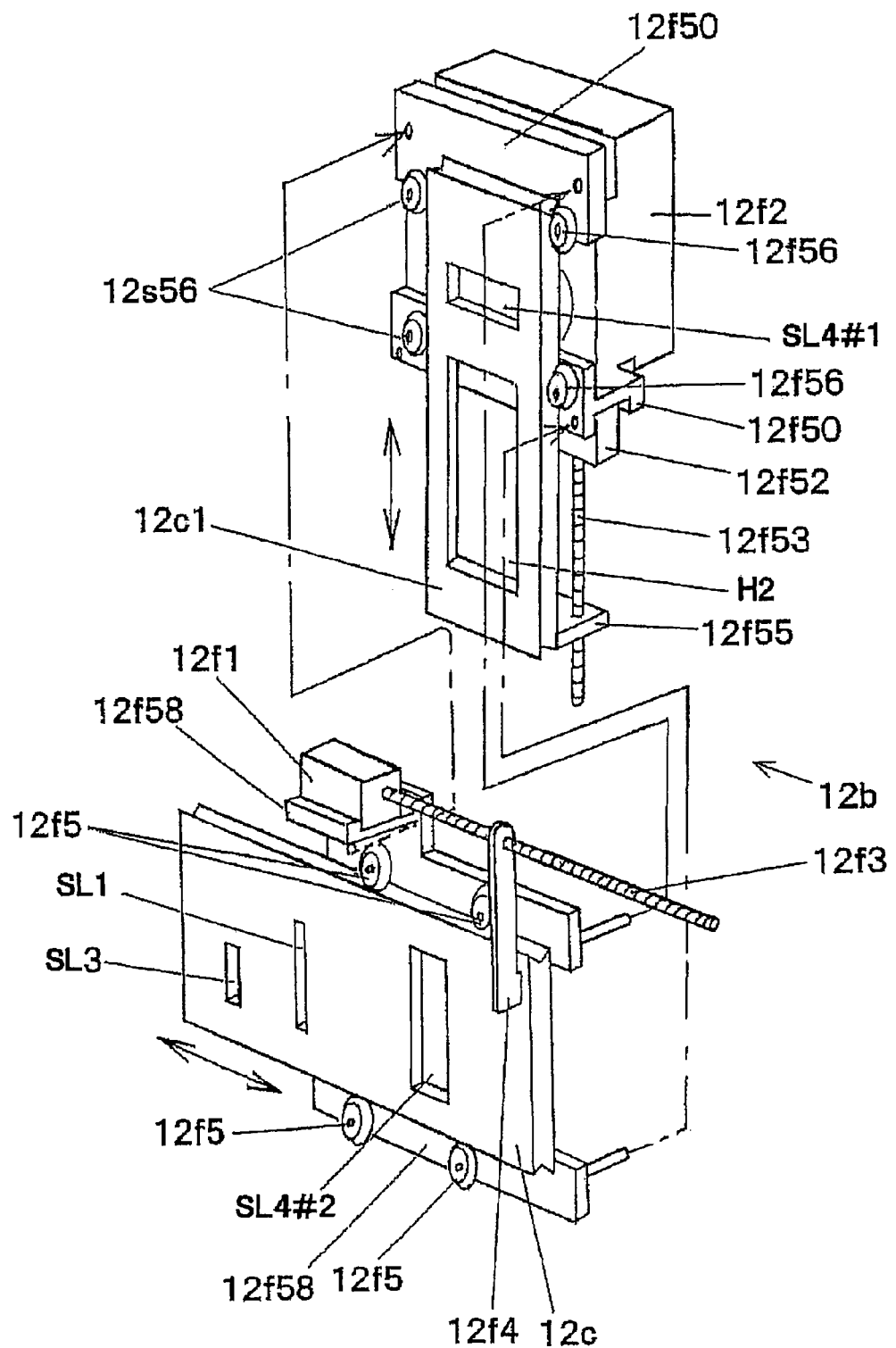
FIG. 26 is a disassembled perspective view to explain yet another configuration of the X-ray generating section.

FIG. 26 is an application diagram of FIG. 25. That is, it is simply realized by replacing the rectangular slit SL2 of FIG. 25 with a combination slit SL4#1 and replacing the opening section H2 with a combination slit SL4#2, so that the other explanation is omitted.

This example is characterized in that the combination slits SL4#1 and SL4#2 are combined to cooperate in changing an irradiation field in a case of computed tomography. A longitudinal width of the combination slit SL#1 is set to be the same length with a longitudinal width of the rectangular slit SL2, and a lateral width of the combination slit SL4#1 is set to be longer than a lateral width of the rectangular slit SL2. Meanwhile, a longitudinal width of the combination slit SL4#2 is set to be longer than a longitudinal width of the rectangular slit SL2, and a lateral width of the combination slit SL4#2 is set to be the same length with a lateral width of the rectangular slit SL2. Accordingly, combination of the combination slits SL4#1 and SL4#2 provides an opening portion which is the same with that of the rectangular slit SL2, so that two-dimensional upper, lower, left and right control of an irradiation field can be achieved by adjusting respective displacement amounts.

Figures 27A, 27B:
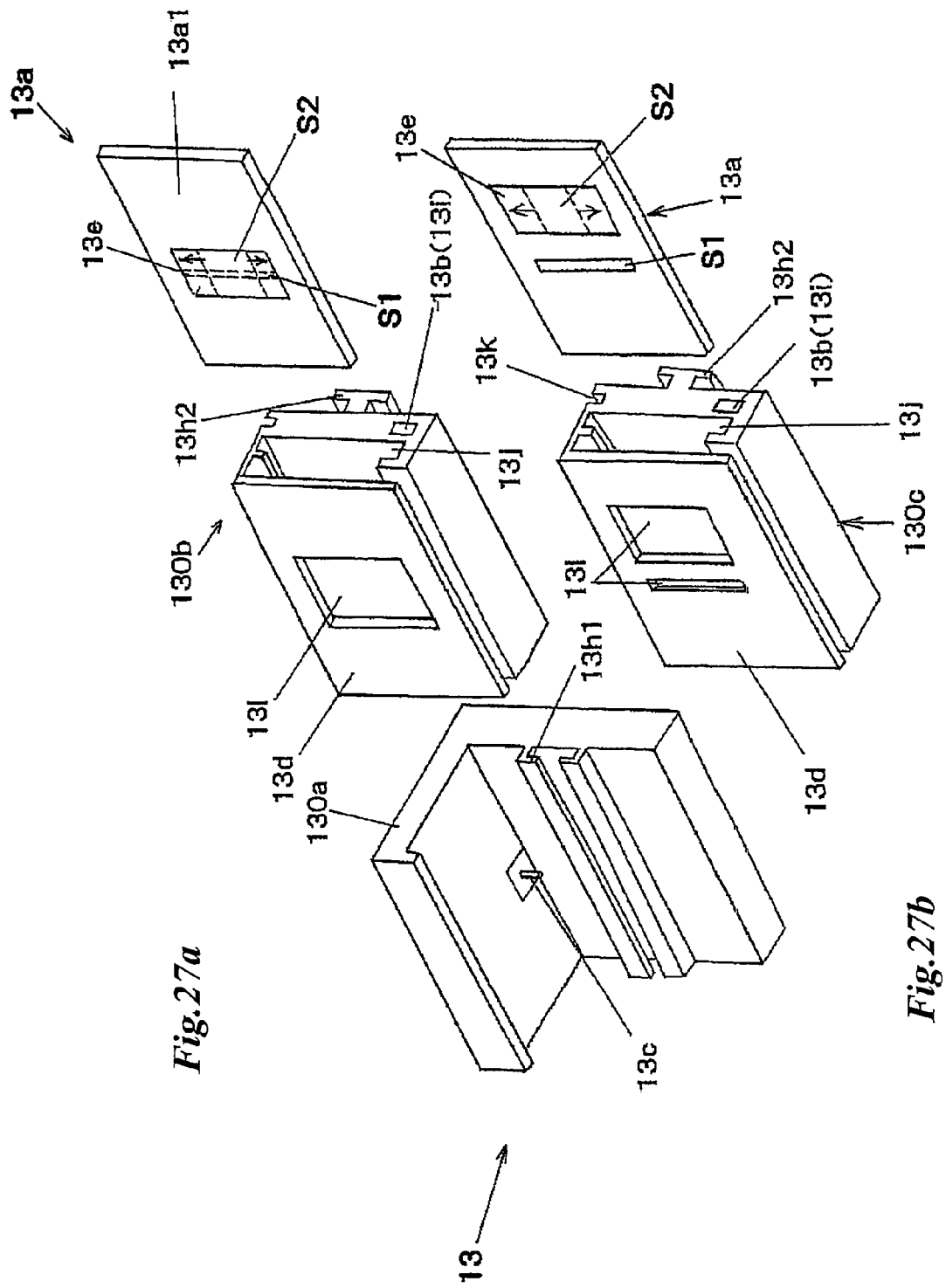
FIGS. 27a and 27b are disassembled perspective views to explain two kinds of configurations of the X-ray detecting section.
Figure 28:
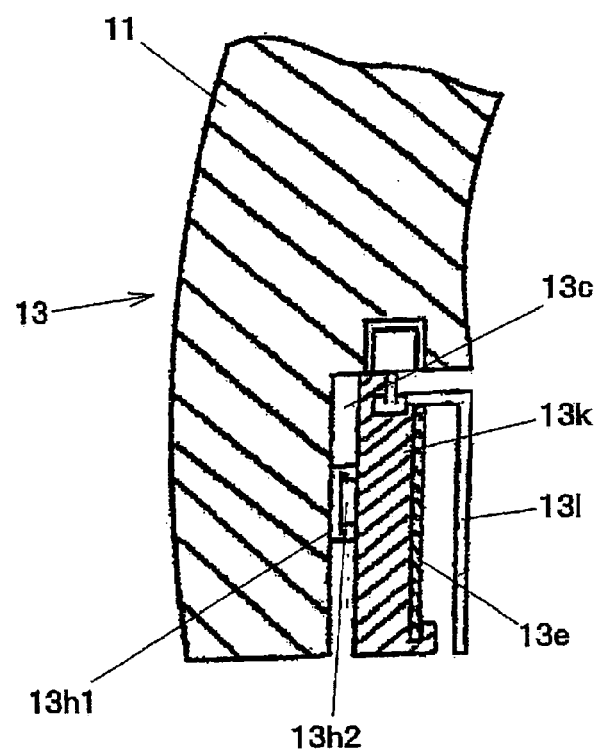
FIG. 28 is a longitudinal sectional view to explain a configuration of the X-ray detecting section shown in FIGS. 27a and 27b.

Explained next will be a configuration of the X-ray detecting section 13. FIGS. 27a and 27b are disassembled perspective views showing a basic configuration of the X-ray detecting section 13, and FIG. 28 is a longitudinal sectional view thereof. The X-ray detector 13a formed into a cassette shape is mounted onto the X-ray detecting section 13 which is provided with an X-ray detector control circuit 13b for driving control of the X-ray detector 13a. Moreover, further provided are a cassette holder 13j, a cassette moving means 13c such as a slide motor for moving the X-ray detector 13a, and an exposure field control means 13d having a slit to control an X-ray beam exposure region.

The X-ray detector 13a is formed as a case cassette replaceable, mountable, attachable and detachable to the X-ray detecting section, and the case is provided with an imaging element to which X-ray images are projected. A semiconductor X-ray detection element can be used as an imaging element so as to be configured into a two-dimensionally expanded flat panel. To be more specific, a MOS sensor, CMOS sensor, TFT sensor, CCD sensor, MIS sensor, CdTe (cadmium telluride) sensor, and X-ray solid-state image sensing device and the like are usable. Then, the imaging element constitutes the first imaging means S1 corresponding to the X-ray slit beam B and the second imaging means S2 corresponding to the X-ray broad beam BB as stated above. That is, the X-ray detecting section 13 is provided with the first imaging means S1 and the second imaging means S2 by mounting the X-ray detector 13a.

Namely, the X-ray detector 13a is a base onto which the first imaging means S1 and the second imaging means S2 are disposed. A mounting portion of the X-ray detector 13a may have a size set to be the same size and shape with a conventional X-ray film cassette so as to be convertible with the X-ray film cassette, but it does not necessarily need to be a cassette shape, and an arbitrary size and shape may be applied. Accordingly, an XII (X-ray image intensifier) can be used as the second imaging means S2. The X-ray detector 13a may also be fixed to or formed in integration with the X-ray detecting section 13 without being replaceable, mountable, attachable and detachable to the X-ray detecting section 13.

The X-ray detecting section 13 of this example is configured by a base section 130a being a base of the X-ray detecting section 13, movable sections 130b and 130c attached to the base section 130a and functioning as a sensor holder to be displaced substantially in parallel with a rotating direction of the X-ray detecting section 13, and the X-ray detector 13a mounted onto the movable section 130b or 130c, including the first imaging means S1 and the second imaging means S2.

In the X-ray detector 13a shown in FIG. 27a, the first imaging means S1 extending in a direction parallel to the rotary shaft A, and the second imaging means S2 which is more expanded than the first imaging means S1 two-dimensionally and used in computed tomography are subjected to region setting so as to be partially overlapped on a single imaging plane of the same imaging element 13e provided in the X-ray detector 13a. Meanwhile, in the X-ray detector 13a shown in FIG. 27b, region setting of the first imaging means S1 is made on an imaging element being different from the imaging element 13e in which region setting of the second imaging means S2 is made. However, in either case, a moving means of the imaging means for changing region setting of the second imaging means S2 to a position parallel to the rotary shaft A is configured in the X-ray detector control circuit 13b, where a region of the second imaging means S2 is set and changed non-mechanically by electronic or software methods.

Since irradiation fields of X-ray cone beams can be switched by the slits SL1 and SL2 and the like of the aforementioned irradiation field changing means 12b, so that an enter plane of the imaging element 13e may be always used as an effective region.

In FIG. 27a, the first imaging means S1 and the second imaging means S2 are subjected to region setting on a detection plane of the same imaging element 13e and thereby can be considered as a first imaging plane and a second imaging plane.

The first imaging means S1 and the second imaging means S2 of FIG. 27 may be configured by an imaging means S2' of FIG. 29 to be described later.

Explanation is made for the movable section 130b shown in FIG. 27a, where the base section 130a includes a guide section 13h1 for guiding a guided section 13h2 provided in the mobile section 130b, and the mobile section 130b is driven for displacement by the cassette moving means 13c composed of a motor and rollers for example. This mobile section 130b is provided with the cassette holder 13j for mounting the X-ray detector 13a, where the X-ray detector 13a shown in FIG. 27a is mounted. The movable section 130b is further provided with the exposure field control means 13d so as to cover a front surface of the X-ray detector 13a. The exposure field control means 13d is made of a flat plate member, where a secondary slit 13l of a size suitable for the first imaging means S1 and the second imaging means S2 is opened to allow irradiation of X-ray beams to the first imaging means S1 and the second imaging means S2 while interrupting the other unnecessary X-ray beams.

The movable section 130c shown in FIG. 27b is provided for mounting the X-ray detector 13a shown in FIG. 27b. The difference from the movable section 130b is that two suitable secondary slits 13l are opened to correspond to the X-ray detector 13a with individual region setting of the first imaging means S1 and the second imaging means S2. The movable section 130c is displaced with respect to the base section 130a so that a selected side of the first imaging means S1 and the second imaging means S2 of the X-ray detector 13a is disposed in a position irradiated by X-ray beams.

Although the example of FIG. 27a exhibits the first imaging means S1 and the second imaging means S2 as examples of longitudinal and rectangular shapes respectively, these shapes are not particularly limited, and any two-dimensionally extended shapes may be applied to the second imaging means S2 as opposed to the elongate first imaging means S1. What is meant by two-dimensionally expanded here is that the second imaging means S2 is wider than the first imaging means S1.

Figure 29A:
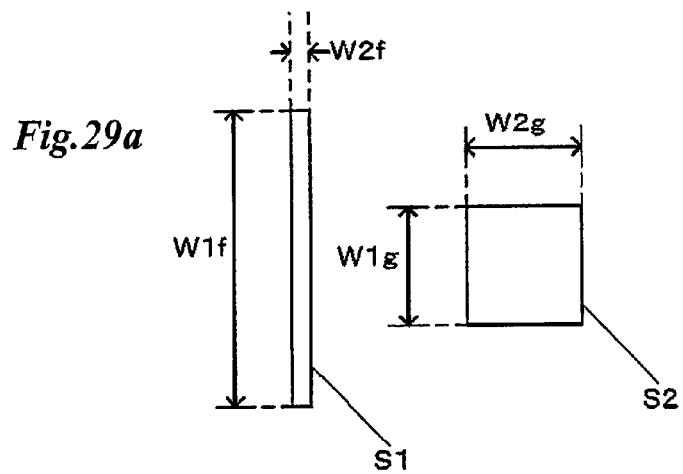
FIGS. 29a to 29d are plane views to explain examples of the first imaging means and the second imaging means in mutually different shapes.
Figure 29B:
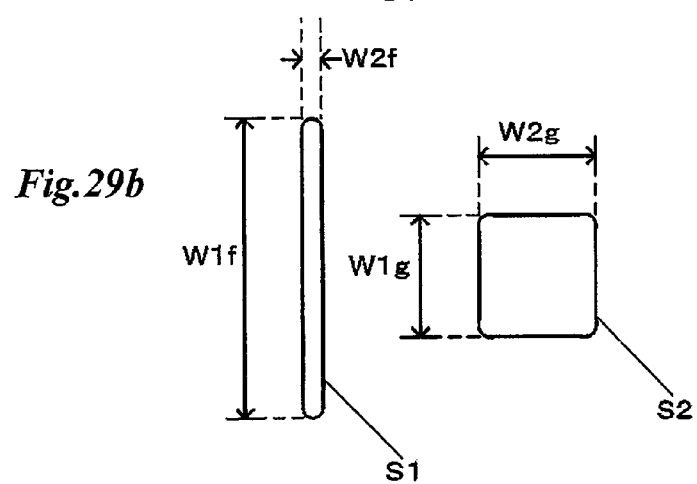

FIGS. 29a and 29b show different examples of the shape of the first imaging means S1 and the second imaging means S2. In the example of FIG. 29a, the first imaging means S1 and the second imaging means S2 are exhibited as examples of longitudinal and rectangular shapes respectively in the same manner with the example of FIG. 27a. However, shapes as shown in FIG. 29b may be possible and arbitrary shapes can be used. In the example of FIG. 28b, the first imaging means S1 is shaped into a longitudinal rectangle with four round corners, and the second imaging means S2 is substantially circular.

If it is assumed here that maximum longitudinal and lateral sizes of the first imaging means S1 are $W1f$ and $W2f$ and maximum longitudinal and lateral sizes of the second imaging means S2 are $W1g$ and $W2g$, they can be set to have a relationship of $W1f>W1g$ and $W2f<W2g$. These longitudinal and lateral sizes can be set by a ratio and may be set to have a relationship of $W1f/W2f>W1g/W2g$. For example, $W1f$ may be set by a ratio of 3 to 30 on the assumption that $W2f$ is 1, and $W1g$ may be set by a ratio of 0.3 to 2 on the assumption that $W2g$ is 1.

To be more specific, $W1f$ is set to be about 150 mm or 150 mm±30 mm which is most suitable for a conventional panoramic image, and similarly $W2f$ is set to be about 10 mm or 10 mm±5 mm which is suitable for clearly imaging an objective sectional plane, while $W1g$ is set to be about 120 mm or 120 mm±30 mm which is suitable for imaging a dental arch of a few teeth or only the vicinity of stapes of the ear, and similarly $W2g$ is set to be about 120 mm or 120 mm±30 mm which is suitable for imaging only a dental arch of a few teeth or the vicinity of stapes of the ear.

If an irradiation field shape in the first imaging means S1 of the X-ray slit beam B is formed to be suitable for the first imaging means S1 and an irradiation field shape in the second imaging means S2 of the X-ray broad beam BB is formed to be suitable for the second imaging means S2 by setting the slits, X-ray beams can be irradiated without waste.

Figure 29C:
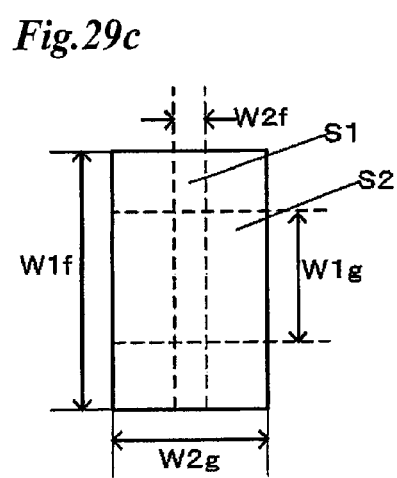

The second imaging means may be deformed and an imaging means as shown in the imaging means S2' of FIG. 29c may be employed. The imaging means S1 and imaging means S2 are both set on a detection plane of the imaging means S2'.

The imaging means S2' is set to have a maximum longitudinal width which is the maximum longitudinal width $W1f$ of the imaging means S1, and have a lateral maximum width which is the lateral maximum width size $W2g$ of the imaging means S2.

Therefore, the imaging means S1 and the imaging means S2 can be set on a detection plane of the same imaging means S2'. If this imaging means is employed, the first imaging means S1 and the second imaging means S2 can be configured by the same imaging means S2'.

Figure 29D:
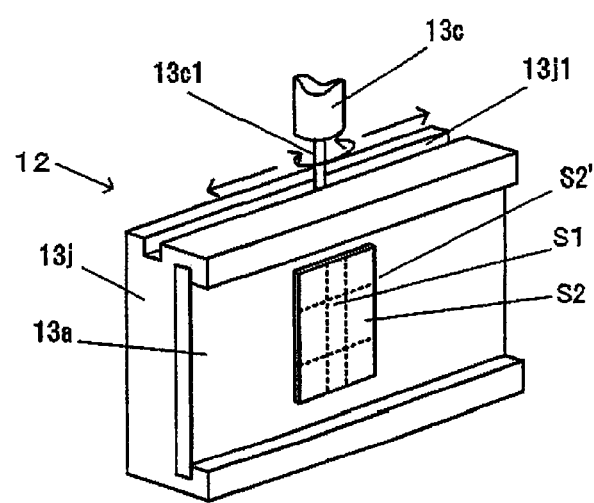

The X-ray detector 13a of FIG. 29d is configured by using the imaging means S2' as a modification of the X-ray detector 13a of FIG. 4c.

In the X-ray detector 13a of FIG. 29d, the first imaging means S1 and the second imaging means S2 of the X-ray detector 13a of FIG. 4a are configured by the same imaging means S2'.

That is, in the X-ray detector 13a of FIG. 29d, the first imaging means S1 and the second imaging means S2 are both set on a single imaging plane. The X-ray detector 13a of FIG. 29d can be employed as the X-ray detector 13a of FIG. 27a.

If the size of a lateral width of a detection plane of the entire second imaging means S2 of this invention is set in a size corresponding to a lateral width of an interested area s required in specific medical fields such as dental surgery and otorhinolaryngology (ex. interested area such as only a dental arch, only a specific portion in a dental arch, and only the vicinity of stapes of the ear), and if an irradiation field of the broad beam BB irradiated to the second imaging means S2 is set to have a size required for a detection plane of the second imaging means S2, the broad beam can be irradiated only to the interested area and reduction in an exposure amount can be achieved. Similarly, a vertical width of a detection plane of the second imaging means S2 may be set in a size corresponding to a vertical width of the interested area s, and an irradiation field of the broad beam BB irradiated to the second imaging means S2 may be set to have a size required for a detection plane of the second imaging means S2. The second imaging means S2 can be effectively used for computed tomography and the like, as needles to say.

Although the lateral width W2g of the imaging means S2' may not have a size to, for example, capture an entire head portion or an entire dental arch of a patient who becomes an object to be examined, a vertical width is set to have a size which is sufficiently enough to be used in panoramic radiography for example.

If the lateral width W2g has a small size, the supporting means 11a is displaced in a horizontal direction to change a position, and images are captured for a plurality of times to allow image composition in a wide range.

The control means 16 is configured by an X-ray generation control means 16a for controlling a tube voltage and a current of the X-ray generator 13a, a slit control section 16b for controlling the slits of the irradiation field changing means 12b, another slit control section 16c for controlling the slits of the exposure field control means 13d of the X-ray detecting section 13, a type determination section 16d for determining types of the imaging means S and an X-ray film cassette of the X-ray generator 13a, a cassette moving means control section 16e for driving the cassette moving means 13c, an orbit control means 16f for drive controlling respective control motors of the moving means 11, a clock generation section 16g for generating control clocks of the X-ray detector control circuits 13b and the imaging orbit control means 16f, an operation panel 16h for simply displaying information and receiving operation input, a work memory 16i for temporarily storing various kinds of variables for control, a frame memory 16j for storing captured X-ray images in each frame, and a CPU 16k for integrating the control means 16.

The display section 14 is configured by a workstation and a personal computer and the like connected to the control means 16 via a communication cable, including a video memory 14a for storing image data, a signal processing means 14b for executing image processing with respect to the image data stored in the video memory 14a, and an image reconstructing means 14c for reconstructing various kinds of images, where further provided are a CRT 14d for displaying images and various kinds of information. A liquid crystal display may be used in place of the CRT 14d. Alternatively, the CRT 14d and a liquid crystal display may be independently arranged from a workstation and the like so that the video memory 14a, a signal processing means 14b, and the image reconstructing means 14b are configured as a part of the control section 16.

The operating section 15 is configured by a keyboard and a mouse of the workstation and the personal computer and the like. Of course, the display 14 using a liquid crystal display and the like in a touch panel system in place of the CRT 14d may be employed so as to be served as the operating section 15.

Explained next will a basic operation of the radiography apparatus M. This invention provides a medical radiography apparatus to specify the interested area R in the object o in order to obtain CT images of the interested area R, and therefore the control means 16 performs a basic operation which is summarized by displaying a first X-ray image obtained by scanning of the object o in a wide range by the first imaging means S1, i.e. scout view image, in the display section 14, using an operation of the operating section 15 to specify the interested area R being a specific part of the object o on an image displayed in the display section 14, and, in accordance with a specified result, controlling the irradiation field changing means 12b, controlling a position of the second imaging means S2, controlling a position of the supporting means 11a and/or the object supporting means 11c, i.e. positioning control of the moving means 11 as an aggregate, and controlling to capture a second X-ray image, i.e. CT images.

Figure 30:
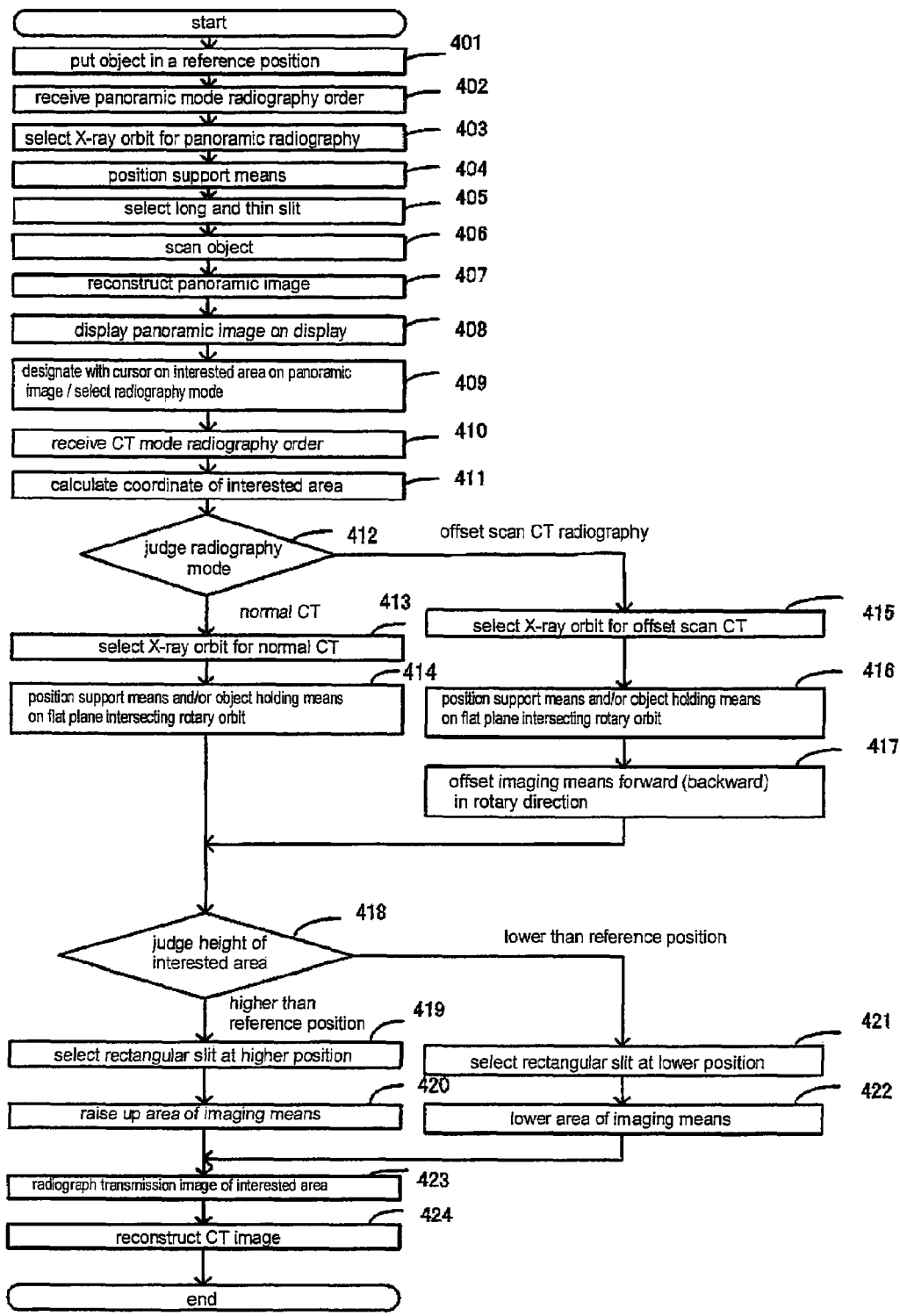
FIG. 30 is a flowchart to explain another basic operation of the radiography apparatus.

FIG. 30 is a flowchart showing control procedures to realize a basic operation by the control means 16. According to this flowchart, the control means 16 initially executes arrangement steps to arrange the object o in a reference position. That is, if a predetermined operation is received by a keyboard of the operating section 15 or the operation panel 16h, the object holding means 11c holding the object o is moved up and down to position the object o in a reference position (step 401).

Then, a panoramic mode is selected as a radiography type of the first X-ray image by an operation of a keyboard of the operating section 15 or the operation panel 16h, and if radiography command is further received (step 402), preliminary radiography steps are executed, including selection of a panoramic radiography orbit as an X-ray beam orbit (step 403), positioning of the supporting means 11a on a plane intersecting the rotary shaft A (step 404), selection of the narrow grooved slit SL1 in the irradiation field changing means 12b (step 405), and scanning of the first X-ray image by using the first imaging means S1 (step 406).

Figure 31:
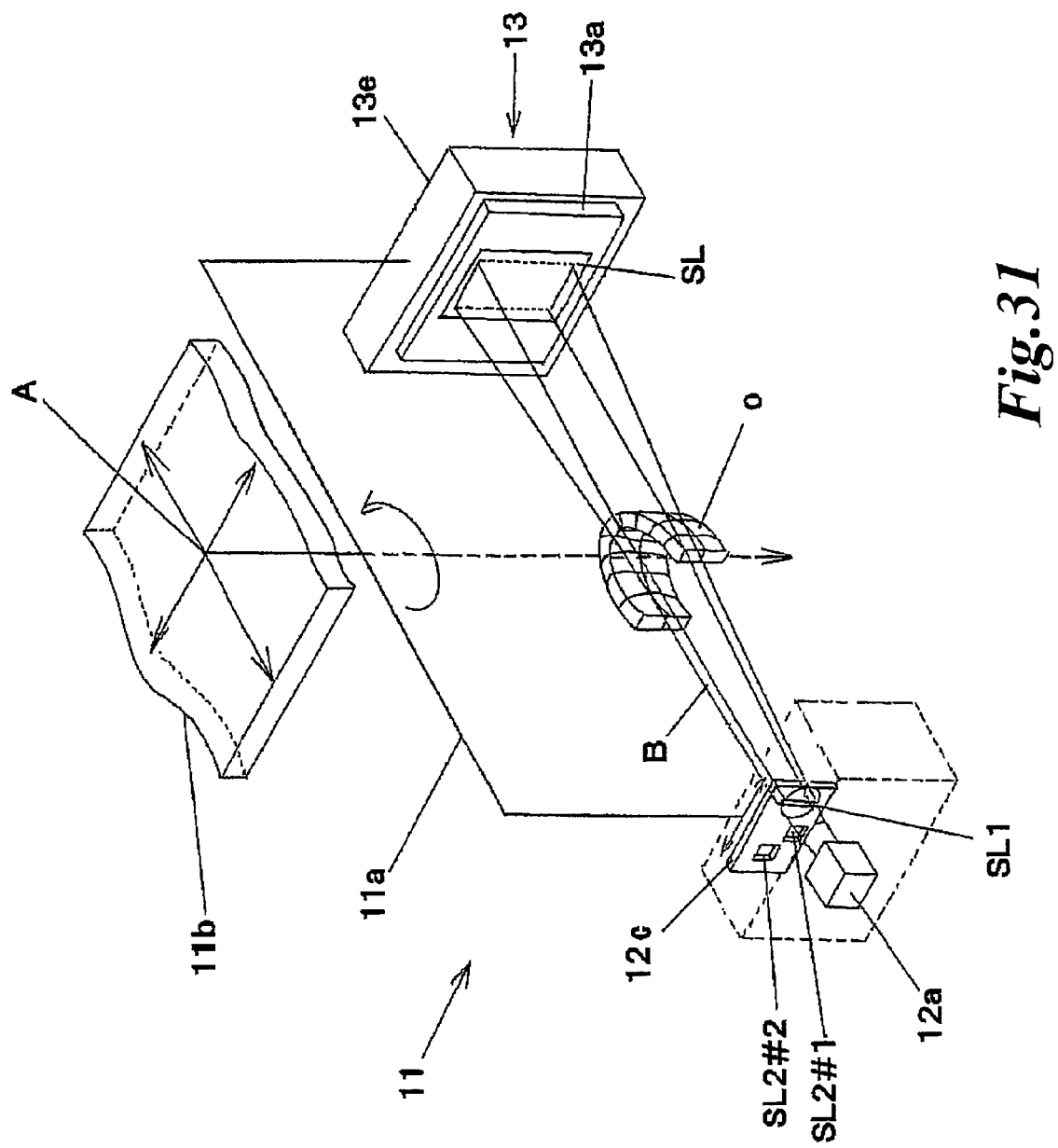
FIG. 31 is a schematic diagram to explain a state in scanning.

FIG. 31 is a schematic diagram to explain a state in scanning. In FIG. 31, an extension line of the rotary shaft A passes through a central portion of a dental arch of a patient typically drawn as the object o. The X-ray slit beam B is controlled by the slit SL1 of the primary slit plate 12c, and an elongate transmission image of the dental arch is projected to the first imaging means S1.

When radiography of the first X-ray image is thus completed, interested area specifying steps are executed, including processing and reconstructing obtained image data (step 407), displaying a panoramic image in the display section 14 (step 408), and specifying the interested area R on a panoramic image by a cursor interlocked with a mouse operation of the operating section 15 and the like in order to select a type of the second X-ray image (step 409).

Thereafter, a normal CT mode or an offset scan CT mode is selected as a radiography type of the second X-ray image by an operation of a keyboard of the operating section 15 or the operation panel 16h. This offset scan is as described above. Then, if a radiography command is further received (step 410), radiographic position adjustment steps are executed. Coordinates of a position of the specified interested area R are calculated (step 411), followed by determining a type of the second X-ray image (step 412). If a type of the second X-ray image is normal computed tomography, select a normal CT orbit as an X-ray beam orbit (step 413), and move and position the supporting means 11a on a plane intersecting the rotary shaft A (step 414). Meanwhile, if a type of the second X-ray image is offset scan computed tomography, select an offset scan CT orbit as an X-ray beam orbit (step 415), move and position the supporting means 11a on a plane intersecting the rotary shaft A (step 416), and position the second imaging means S2 to be offset with respect to the X-ray generator 12 and the interested area R by sliding the X-ray detector 13a forward or backward in its rotating direction (step 417). Next, a height of the interested area R is determined (step 418), and if the interested area R is positioned higher than a reference position, select the rectangular slit SL2#2 in the irradiation field changing means 12b (step 419), and set a region of the second imaging means S2 in an upper imaging plane of the imaging element 13e (step 420) in order to position the interested area in a direction parallel to the rotary shaft A. Meanwhile, if the interested area R is positioned lower than a reference position, select the rectangular slit SL2#1 in the irradiation field changing means 12b (step 421), and set a region of the second imaging means S2 in a lower imaging plane of the imaging element 13e (step 422) in order to position the interested area in a direction parallel to the rotary shaft A.

Figure 43:
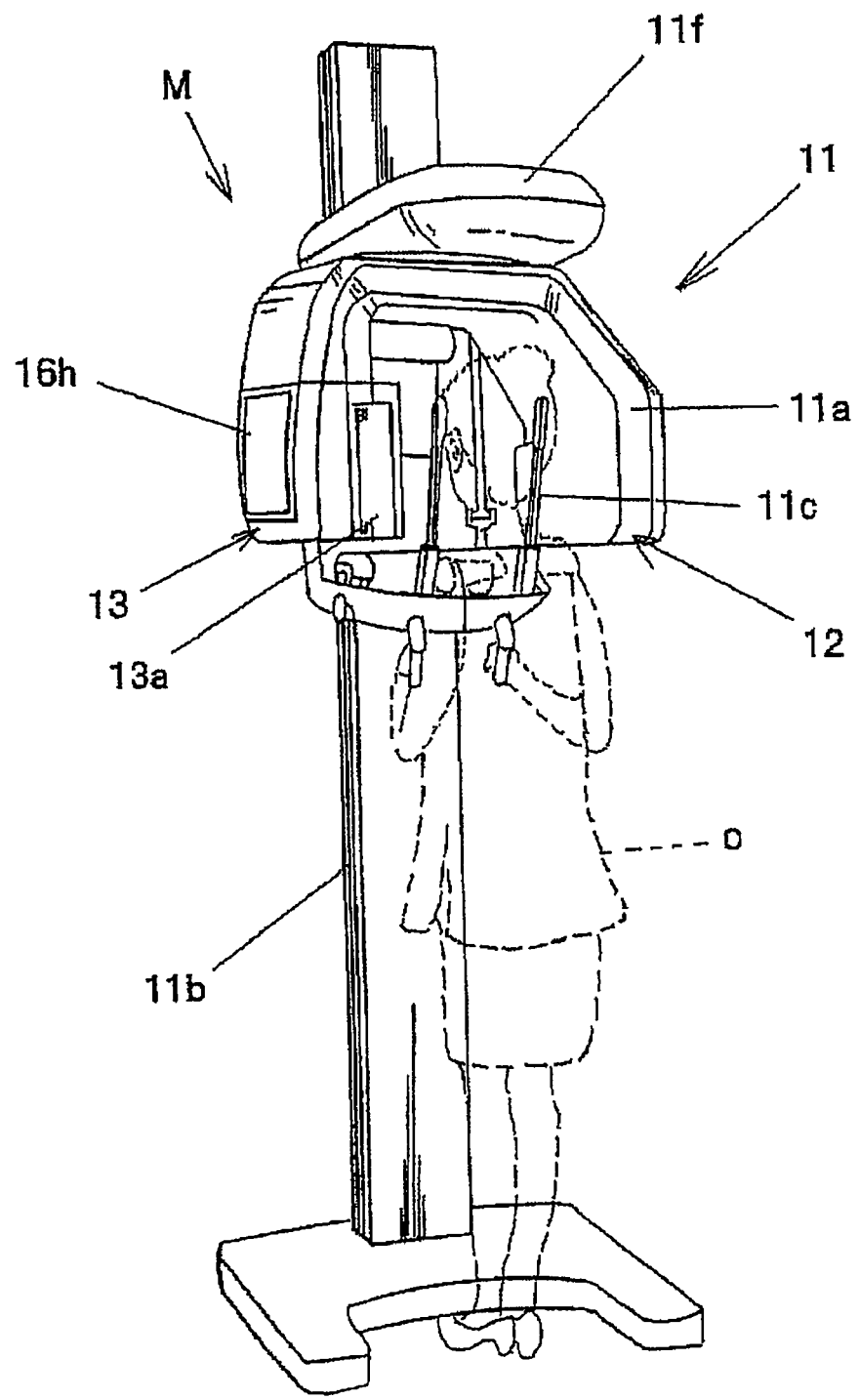
FIG. 43 is a perspective view to explain an appearance of the radiography apparatus in yet different embodiment.

If it is controlled to raise and lower in the supporting means 11a and the object holding means 11c at this time in addition to region setting to provide different positions of the second imaging means S2 on the imaging element 13e, an application range can be more expanded with respect to a position of the interested area R. In order to raise and lower the supporting means 11a and the object holding means 11c, it is possible to use an elevation means not shown for the object holding means 11c provided in the fixed section 11b according to the explanation of FIG. 16, FIGS. 17a and 17b, and a housing frame 1 if to be described later for moving the supporting means 11a up and down according to the later descried explanation of FIG. 43.

On the basis of positioning in the radiography position adjustment steps, main radiography steps are executed, including driving the moving means 11 to capture transmission images including an entire or more than half portion of the interested area R by the second imaging means S2 at each predetermined angle (step 423), and reconstructing CT images for a desired sectional plane of the interested area R by image processing of obtained transmission images (step 424).

In the radiography type selection, at least a panoramic mode and a CT mode can be selected, where a normal CT mode and an offset scan CT mode can be further selected as a CT mode. However, a linear scan mode or other modes may be further added to the selection, and a CT mode may also be automatically selected if the interested area R is specified on the display section 14 displaying a panoramic image in a state that a panoramic mode is selected. Moreover, cephalometric radiography may also be carried out as radiography by the first imaging means S1.

Figure 32:
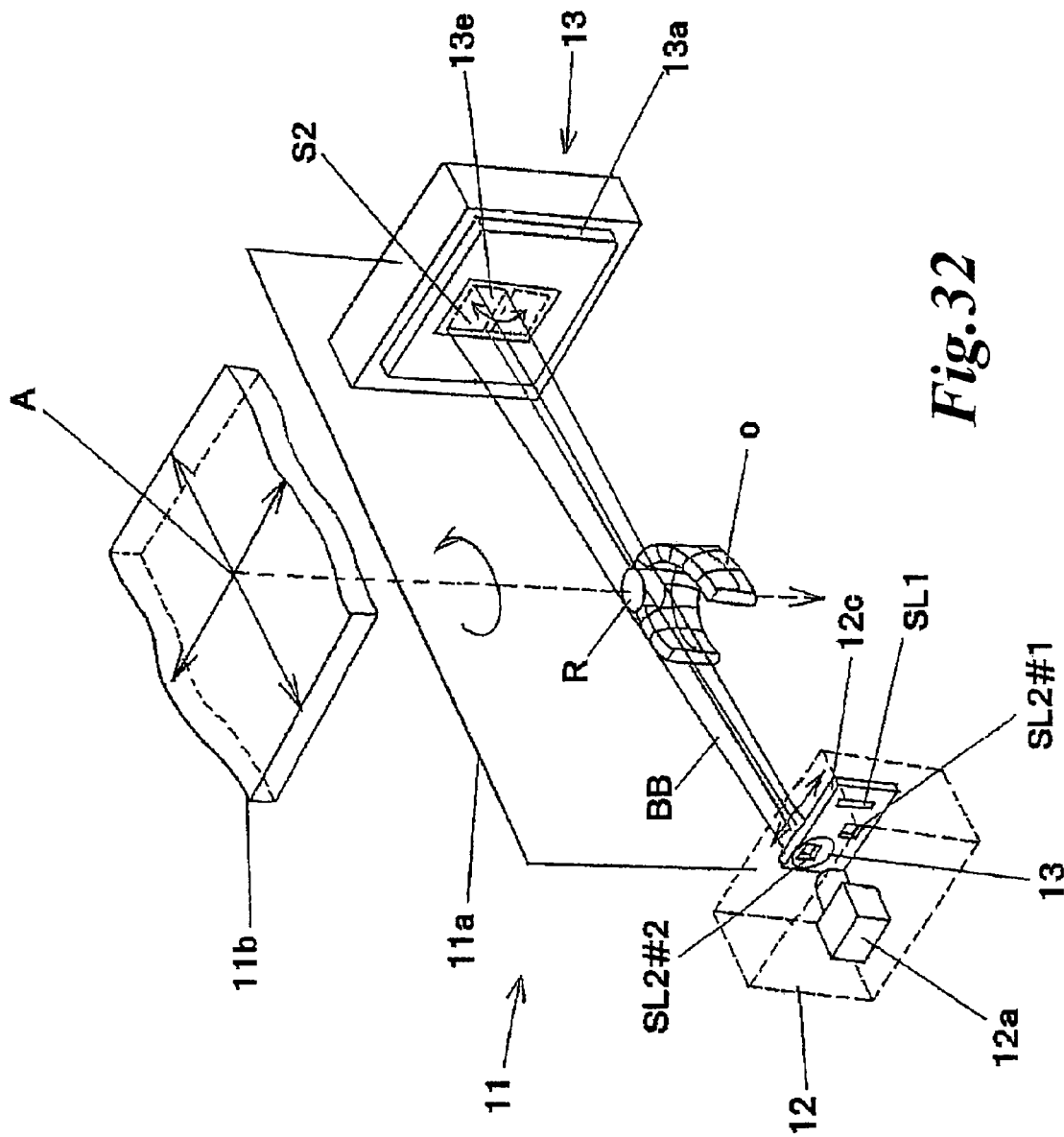
FIG. 32 is a schematic diagram to explain a state of transmission image capturing.

FIG. 32 is a schematic diagram to explain a state in capturing a transmission image of the interested area R. FIG. 32 indicates a state in normal computed tomography, where an extension line of the rotary shaft A passes through the center of the interested area R of a cylindrical body. The X-ray broad beam BB is also controlled by the rectangular slit SL2#2 of the primary slit plate 12c, and a transmission image including the entire interested area R is projected to the second imaging means S2 whose region is set in an upper imaging plane of the imaging element 13e. The X-ray generating section 12 and the X-ray detecting section 13 are moved synchronously along a turning orbit with the rotary shaft A as an optical rotary shaft.

Although the examples of FIGS. 31 and 32 show that the first imaging means S1 and the second imaging means S2 are set on an imaging plane of the same imaging element 13e in the same manner with FIG. 27a, individual imaging plane may be provided for the first imaging means S1 and the second imaging means S2 as shown in FIG. 27b.

Moreover, it is not necessary to limit the setting of the interested area R on a displayed panoramic image to one part per one time, where a plurality of parts may be specified. In this case, it is possible to provide a configuration that a plurality of specified parts are subjected to computed tomography continuously in desired sequence. Setting the interested area R may also be interlocked with computed tomography. That is, in a configuration of automatically selecting a CT mode when the interested area R is specified on the display section 14 displaying a panoramic image as stated above, a process may be further advanced to execute computed tomography instead of simply becoming a CT mode.

Furthermore, the interested area R does not necessarily be specified in a state that a patient who is the object o is fixed to the object holding means 11c after completing panoramic radiography. That is, as long as reproducibility of an object holding state can be sustained, a patient may be released from the object holding means 11c for once and the patient may be fixed to the object holding means 11c again in another time in the same position at the time of completing panoramic radiography, so that a panoramic image recorded in the video memory 14a is invoked to specify the interested area as stated above. In this case, identity information is set for each patient, an object holding state is detected by a detection means such as a potentiometer and stored in a separately provided storage section in association with the identity information, so that an object holding state associated with the identity information may be invoked at the time of fixing a patient again, or the object holding means 11c may be automatically driven to reproduce an object holding state.

Third Embodiment

Explained next is yet another embodiment in accordance with diagrams. In this example, the X-ray detecting section 13 is configured differently from the above embodiments and provided as an X-ray detector 13A, but the other items are commonly configured so that explanation of an entire configuration will be omitted (refer to FIG. 16).

The X-ray detector 13a in a configuration different from that of the above embodiments is mounted onto the X-ray detecting section 13A, and the X-ray detector control circuit 13b for driving and controlling the X-ray detector 13a is provided.

Figures 33A, 33B:
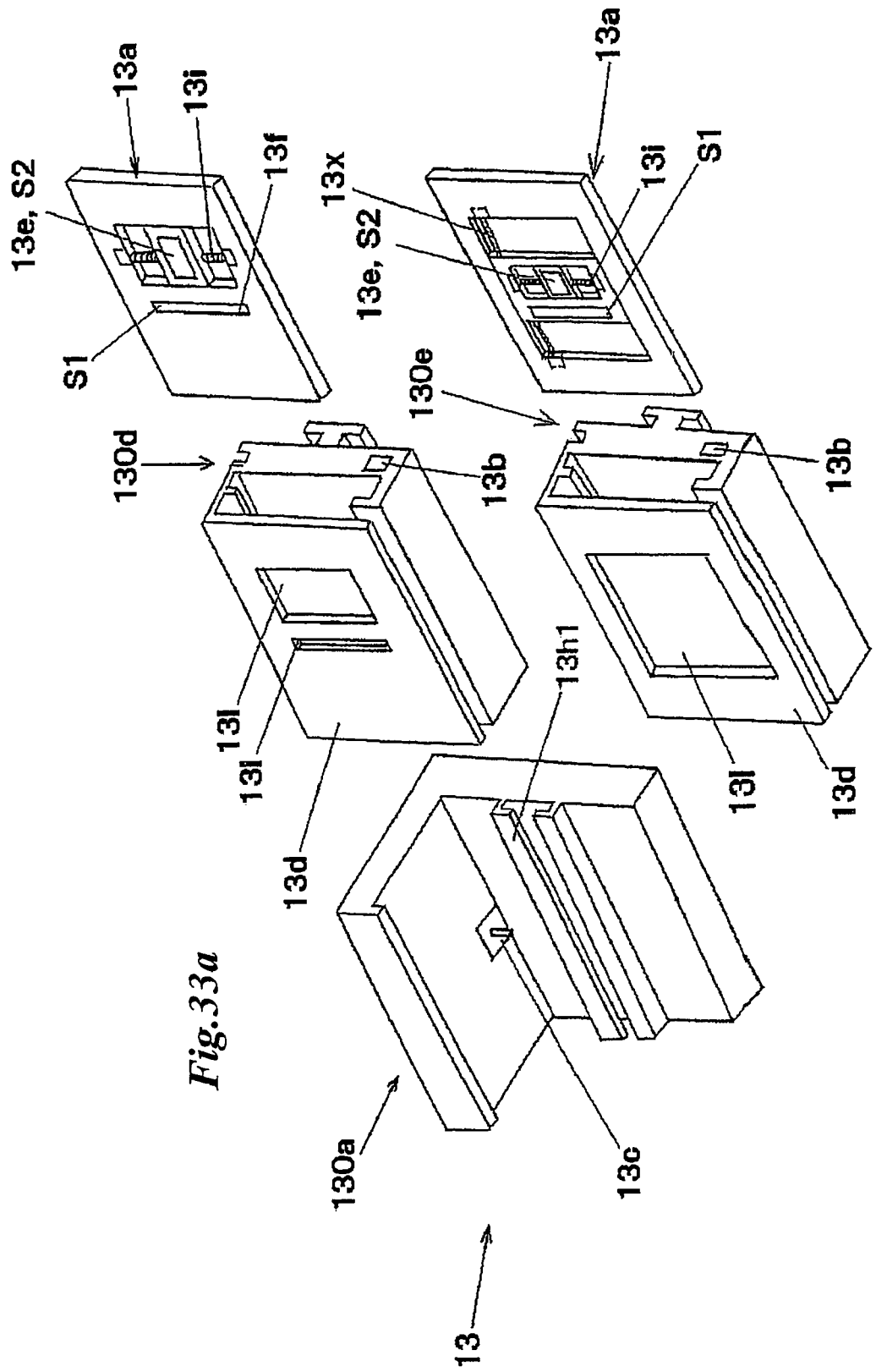
FIGS. 33a and 33b are disassembled perspective views to explain two kinds of further configurations of the X-ray detecting section.

FIGS. 33a and 33b are disassembled perspective views showing basic configurations of the X-ray detector 13A. In either configuration of FIGS. 33a and 33b, the X-ray detector 13a is provided with the first imaging means S1 extending in a direction parallel to the rotary shaft A of the supporting means 11a, and the second imaging means S2 which is for use in computed tomography and two-dimensionally expanded with respect to the first imaging means S1, where only the second imaging means S2 can be mechanically moved up and down in an axial direction of the rotary shaft A of the supporting means 11a by the imaging means moving means 13i in a configuration shown in FIG. 33a, whereas the first imaging means S1 and the second imaging means S2 are both allowed to move not only in a direction parallel to the rotary shaft A of the supporting means 11a but also in a horizontal direction intersecting thereto by the imaging means moving means 13i in a modified configuration shown in FIG. 33b.

A movable section 130d shown in FIG. 33a has the same configuration with the movable section 130c of FIG. 27b and thereby explanation thereof will be omitted, but a movable section 130e shown in FIG. 33b is different because an opening size of a secondary slit 13l is made larger in accordance with parallel movement of the first imaging means S1 and the second imaging means S2.

Figure 34A:
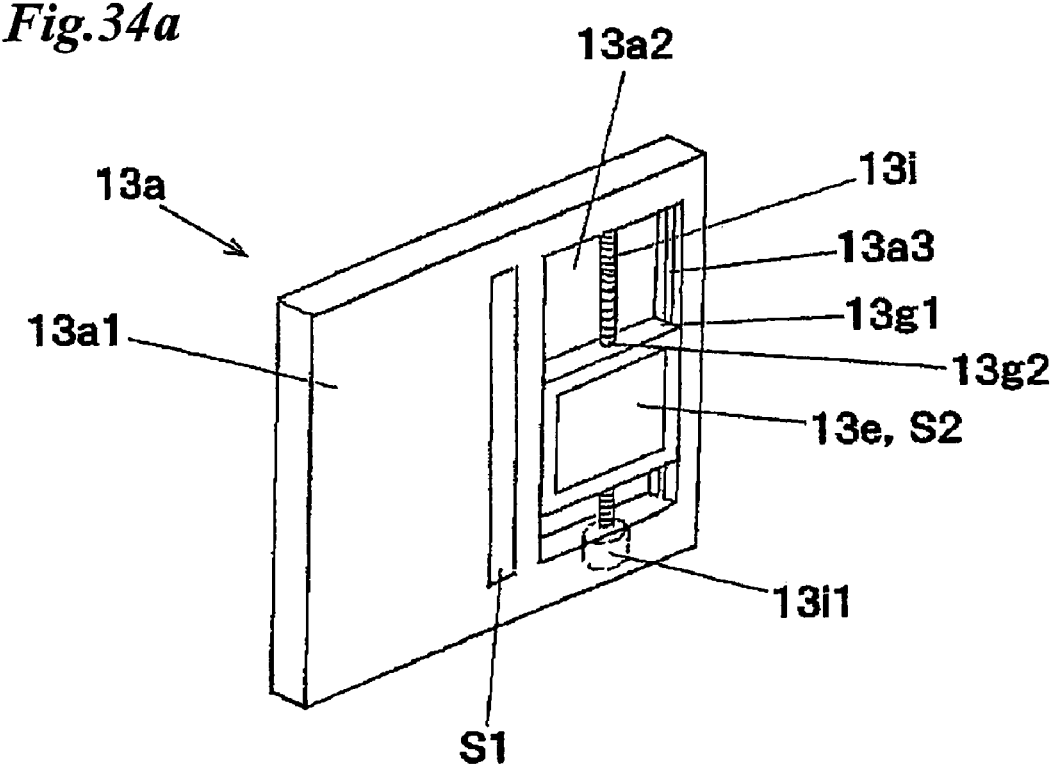
FIGS. 34a and 34b are more detailed perspective views of the X-ray detector shown in FIGS. 33a and 33b.
Figure 34B:
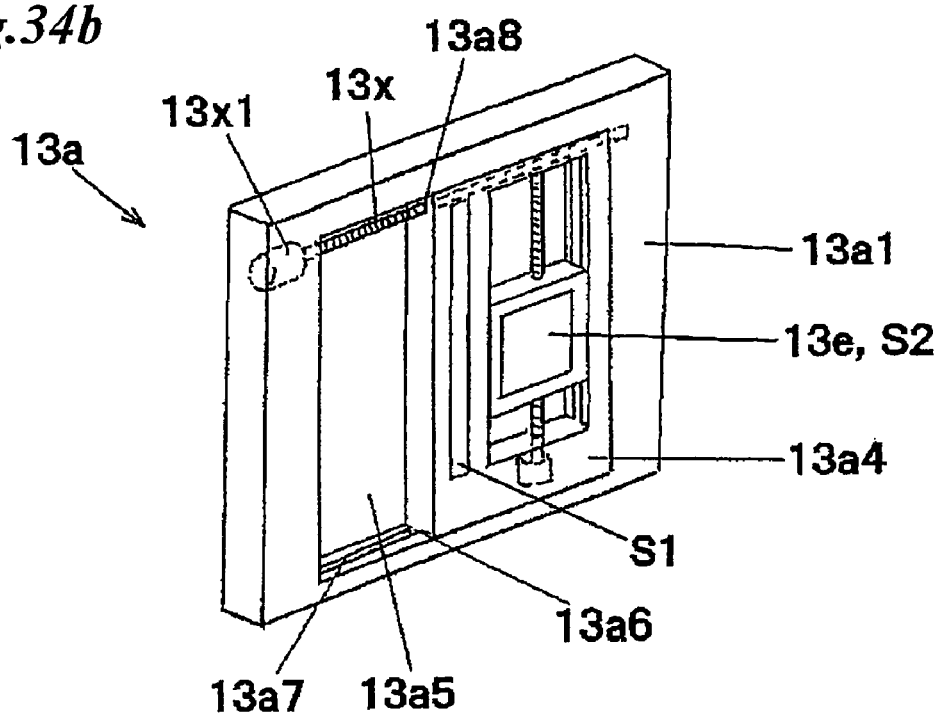

FIGS. 34a and 34b are perspective views showing more detailed configurations of the X-ray detector 13a of FIGS. 33a and 33b.

The X-ray detector 13a shown in FIG. 34a is basically composed of a base board 13a1 formed as a cassette attachable/detachable to/from the movable section 130d which functions as a cassette holder, the first imaging means S1, the second imaging S2, and an imaging means moving means 13i for moving up and down and positioning the second imaging means S2 in the base board 13a1, where the first imaging means S1 is provided substantially in the center of the base board 13a1 and the second imaging means S2 is provided in its side.

A rectangular opening 13a2 is provided in the center of the base board 13a1, and the second imaging means S2 is formed into a size and shape so that moving up and down is allowed inside the opening 13a2. Then, protruding sections 13g1 are provided on left and right side surfaces of the second imaging means S2, and recessed grooves 13a3 corresponding to the protruding sections 13g1 are formed in the opening 13a2. Therefore, the protruding sections 13g1 are fitted into the recessed grooves 13a3 and guided to move up and down in a direction parallel to the rotary shaft A.

The second imaging means S2 is provided with a hole 13g2 which is internally threaded and vertically penetrates therethrough, where the imaging means moving means 13i made of a vertically extending ball screw passes through the hole 13g2 in a state of being engaged with the thread. The imaging means moving means 13i which is fixed to edges of the opening 13a2 in a vertically rotatable state is driven to rotate by the motor 13i1 in order to move the second imaging means S2 up and down.

Meanwhile, a detailed configuration of the X-ray detector 13a shown in FIG. 34b has following differences from the X-ray detector 13a shown in FIG. 34a.

That is, the X-ray detector 13a shown in FIG. 34a is provided with the base board 13a1 including the first imaging means S1 and the second imaging means S2 which is moved up and down by the imaging means moving means 13i, while the X-ray detector 13a shown in FIG. 34b is provided with a large opening 13a5 in the center of the base board 13a1, where another base board 13a4 is displaced in the substantially same direction with a rotating direction of the X-ray detecting section 13 in the inside of the opening 13a5. Then, this base board 13a4 is provided with the first imaging means S1 and the second imaging means S2. A mechanism of moving the second imaging means S2 up and down is the same with that of FIG. 34a, so that explanation thereof will be omitted.

Here, the square opening 13a5 is provided in the center of the base board 13a1, and the base board 13a4 is formed into a size and shape so as to be horizontally moved inside the opening 13a5. Then, protruding sections 13a6 are provided on upper and lower side surfaces of the base board 13a4, and recessed grooves 13a7 corresponding to the protruding sections 13a6 are provided in the opening 13a5. Therefore, the protruding sections 13g6 are fitted into the recessed grooves 13a7 and guided to be displaced substantially in the same direction with a rotating direction of the X-ray detecting section 13.

The base board 13a4 is provided with a hole 13a8 which is internally threaded and horizontally penetrates therethrough, and a base board moving means 13x made of a horizontally extending ball screw passes through the hole 13a8 in a state of being engaged with the thread. The base board moving means 13x which is fixed to edges of the opening 13a5 in a horizontally rotatable state is driven to rotate by a motor 13x1 so as to displace the second imaging means S2. This configuration can also be used in offset displacement of the second imaging means S2 in offset scanning.

Explained next will be a basic operation of the radiography apparatus M of this example.

Figure 35:
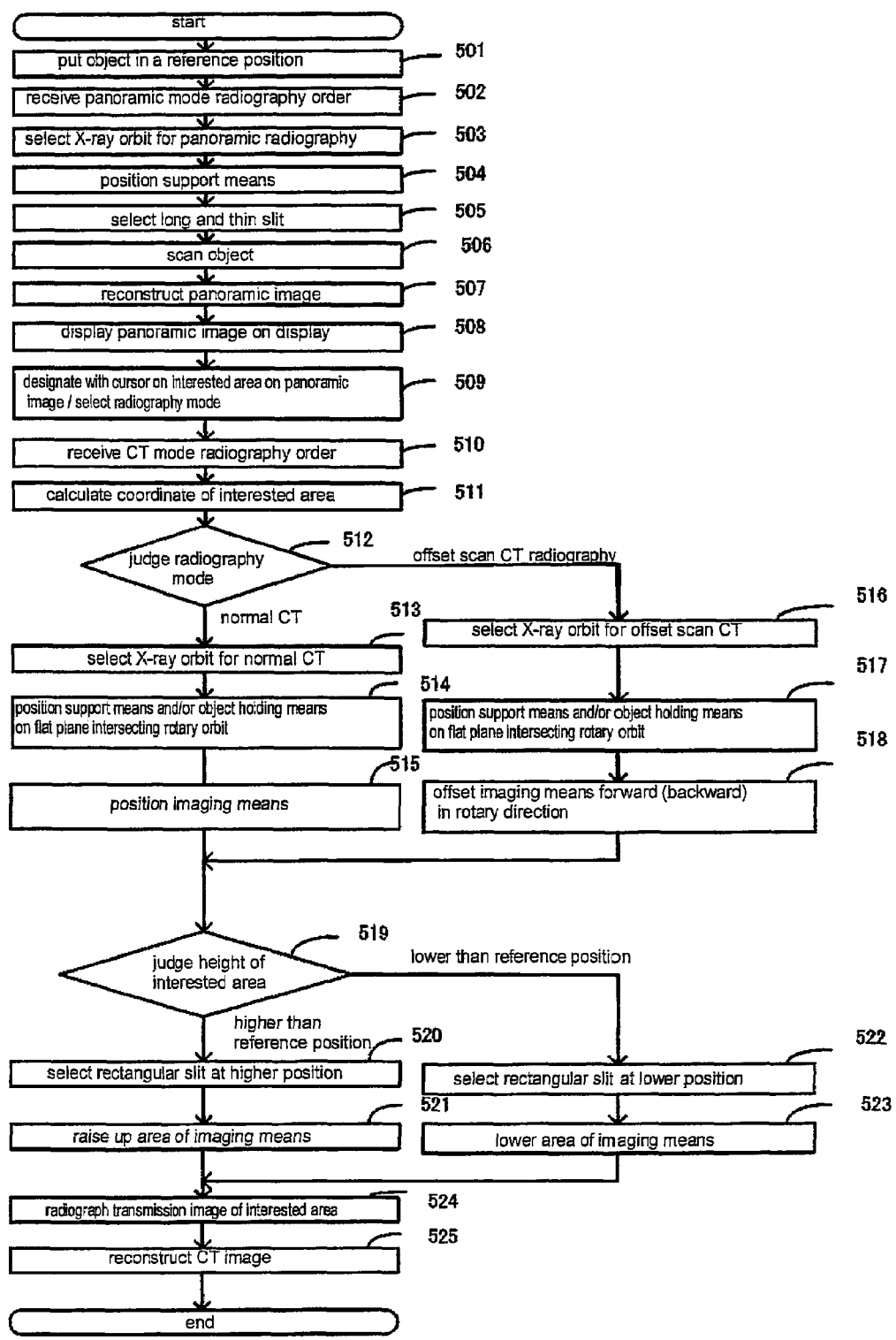
FIG. 35 is a flowchart to explain further different basic operation of the radiography apparatus.

FIG. 35 is a flowchart showing control procedures by the control means 16 in order to realize the basic operation. According to this flowchart, the control means 16 initially executes an arrangement step to arrange the object o in a reference position (step 501), and executes preliminary radiography steps to perform scanning of the object o by using the first imaging means S1, in the same manner with the second embodiment.

Figure 36:
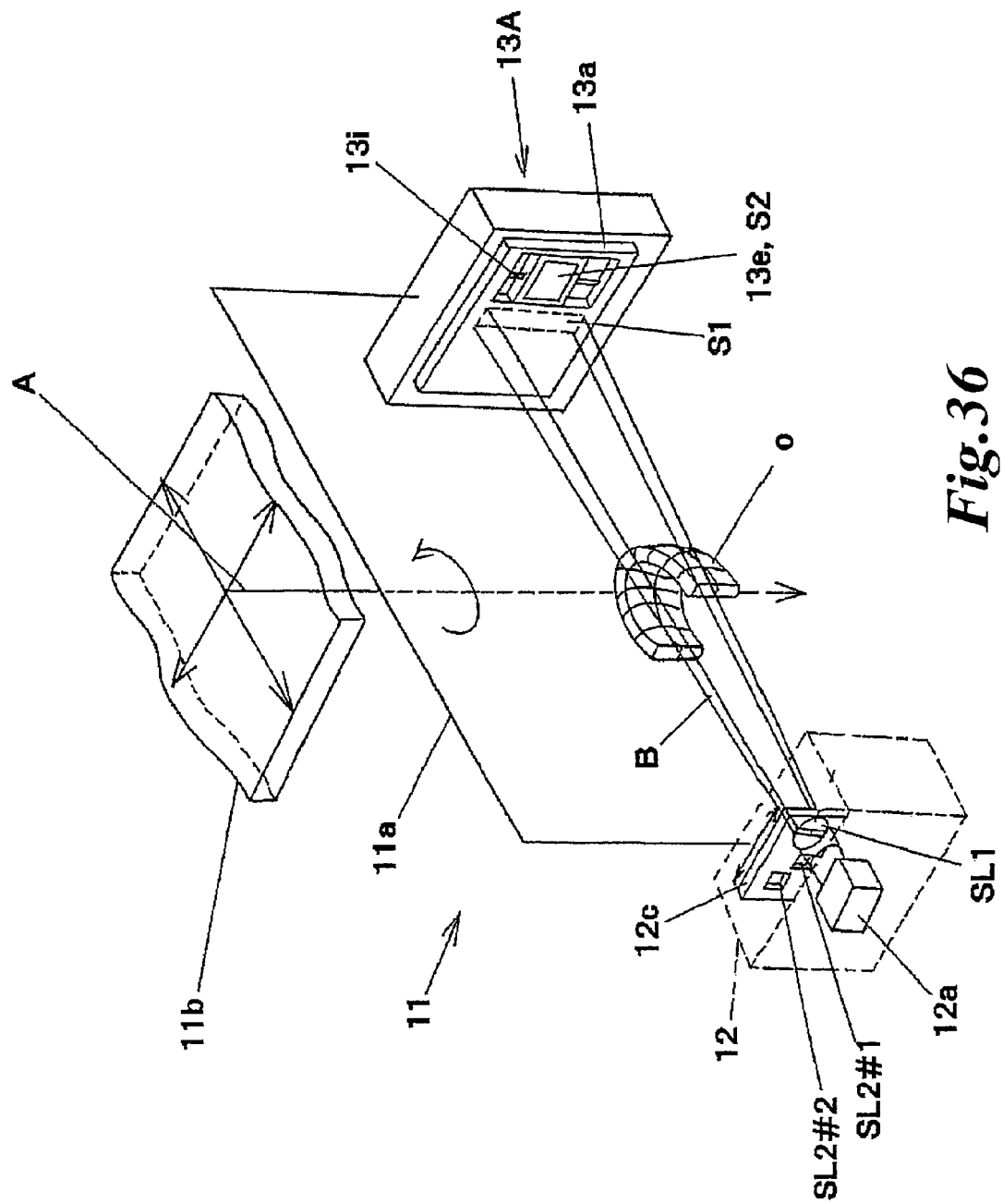
FIG. 36 is another schematic diagram to explain a state in scanning.

FIG. 36 is a schematic diagram to explain a state in scanning of the object o. In FIG. 36, an extension line of the rotary shaft A passes through a central portion of a dental arch of a patient who is drawn as the object o. The X-ray slit beam B is controlled by the narrow grooved slit SL1 of the primary slit plate 12c, and an elongate transmission image of a dental arch is projected to the first imaging means S1. Orbits of the X-ray generating section 12 and the X-ray detecting section 13A at this time remain the same with those of the second embodiment. Steps 501 to 507 are similar to the steps 401 to 407 shown in FIG. 30.

Interested area specifying steps are executed next, including displaying a panoramic image in the display section 14 (step 508), and receiving specification of the interested area R in the object o and a type selection of the second X-ray image by a cursor operation on the display screen or other operation in the operating section 15 (step 509).

Thereafter, if a radiography command of the second X-ray image is received from a keyboard of the operating section 15 or the operation panel 16h (step 510), radiography position adjustment steps are executed. Coordinates of a position of the specified interested area R are calculated (step 511), and a type of the second X-ray image is determined (step 512). If a type of the second X-ray image indicates normal computed tomography, select a normal CT orbit as an orbit of the X-ray broad beam BB (step 513), move and position the supporting means 11a in a plane intersecting the rotary shaft A (step 514), and position the second X imaging means S2 by sliding the X-ray detector 13a forward or backward in a rotating direction so as to dispose in series the X-ray generating section 12, the interested area R and the second imaging means S2 (step 515). If a type of the second X-ray image indicates offset scan computed tomography, select an offset scan CT orbit as an orbit of the X-ray broad beam BB (step 516), move and position the supporting means 11a on a plane intersecting the rotary shaft A (step 517), and position the second imaging means S2 so as to be offset with respect to the X-ray generating section 12 and the interested area R by sliding the X-ray detector 13a forward or backward in a rotating direction by a distance being different from that of normal computed tomography (step 518). Next, a position of the interested area R is determined (step 519), and if the interested area R is positioned higher than a reference position, select the rectangular slit SL2#2 in the irradiation field changing means 12b (step 520), and mechanically raise and position the second imaging means S2 in a direction parallel to the rotary shaft A (step 521). Meanwhile, if the interested area R is positioned lower than a reference position, select the rectangular slit SL2#1 in the irradiation field changing means 12b (step 522), and mechanically lower and position the second imaging means S2 in a direction parallel to the rotary shaft A (step 523).

Next, actual radiography steps are executed in the same manner with the second embodiment, including capturing a transmission image of the interested area R at each predetermined rotation angle on the basis of the positioning in the radiography position adjustment steps (step 524), and reconstruct CT images for a desired sectional plane of the interested area R (step 525).

Figure 37:
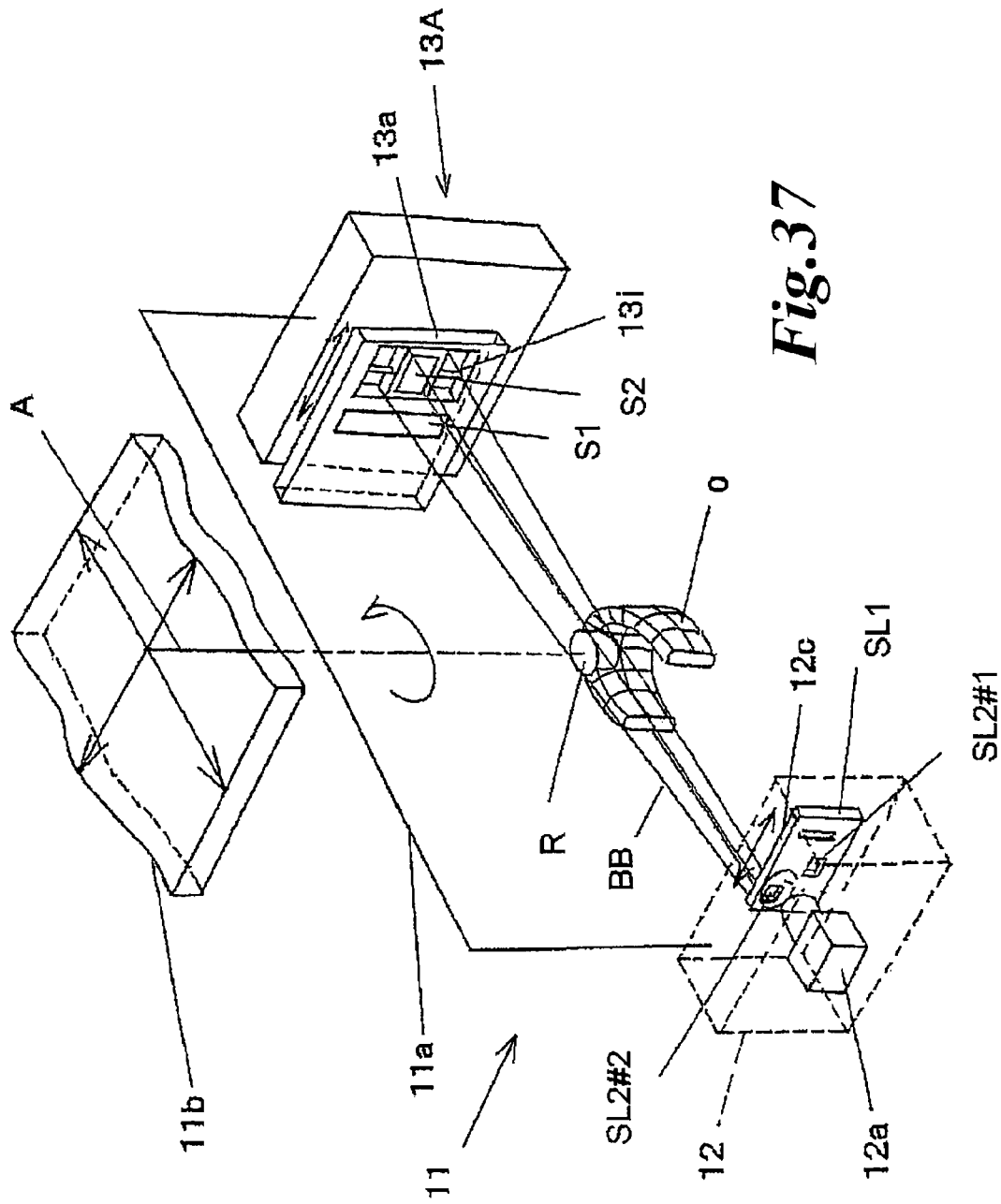
FIG. 37 is another schematic diagram to explain a state in transmission image capturing.

FIG. 37 is a schematic diagram to explain a state in transmission image radiography of the interested area R. FIG. 37 corresponds to a state in normal computed tomography, where an extension line of the rotary shaft A passes through the center of a cylindrical body of the interested area R. The X-ray broad beam BB is also controlled by the rectangular slit SL2#2 of the slit plate 12c, and a transmission image including the entire cylindrical body of the interested area R is projected to the second imaging means S2 whose position is mechanically adjusted by the imaging means moving means 13i. Orbits of the X-ray generating section 12 and the X-ray detecting section 13A are similar to those of the first embodiment.

Fourth Embodiment

Explained next will be a fourth embodiment in accordance with drawings. This embodiment differs from the second embodiment in a configuration of an X-ray detecting section 13B and a further provided elevation means 11w in the object holding means 11c, but the other items are commonly configured, so that duplicated explanation will be omitted.

Figure 38:
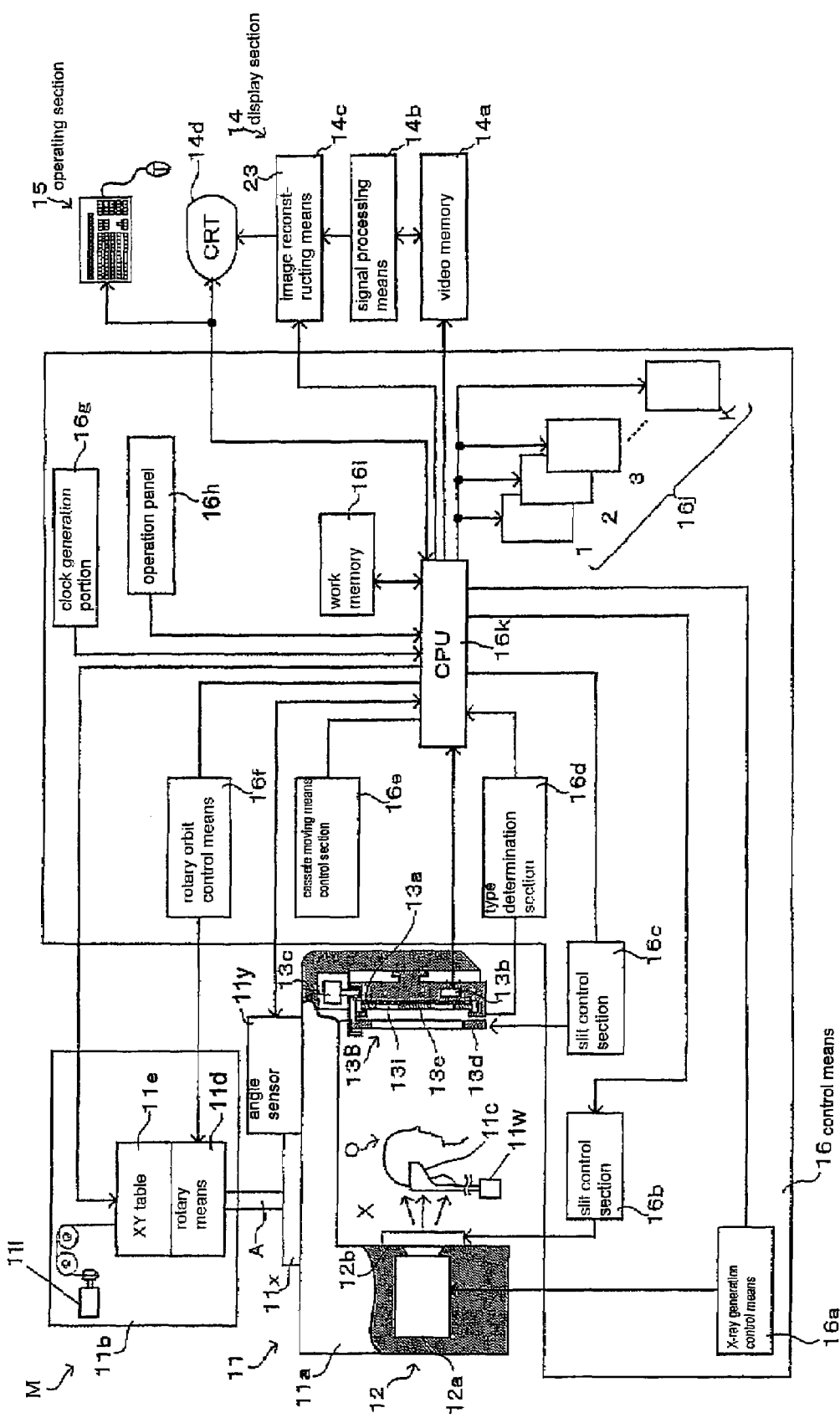
FIG. 38 is a block diagram to explain a schematic configuration of the radiography apparatus of yet another embodiment.

FIG. 38 is a block diagram to explain a schematic configuration of the radiography apparatus M of this embodiment.

The X-ray generating section 12 is provided with the X-ray generator 12a for irradiating X-ray cone beams and the irradiation field changing means 12b for controlling the shape of X-ray cone beams by the slits, having a configuration explained in FIG. 2c, FIGS. 3a and 3b.

Figure 39:
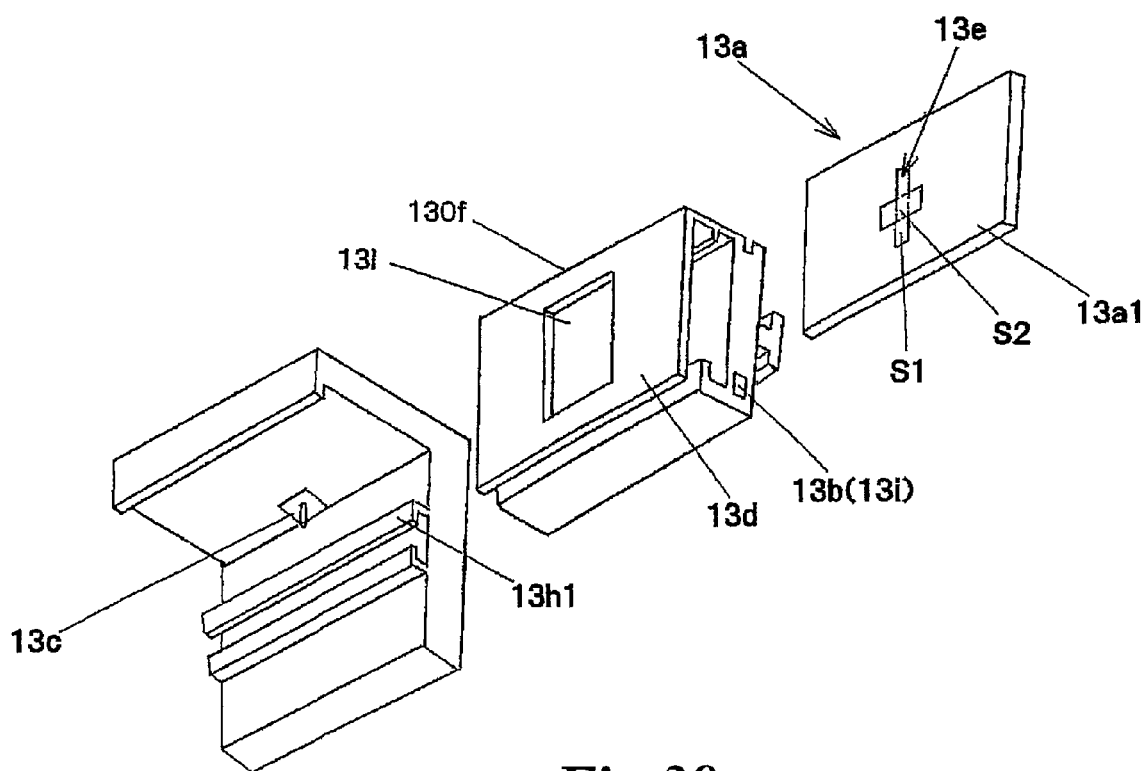
FIG. 39 is a disassembled perspective view to explain a further different configuration of the X-ray detecting section.

FIG. 39 is a disassembled perspective view showing a basic configuration of the X-ray detecting section 13B. The X-ray detector 13a shown in FIG. 39 is basically composed of the base board 13a1 formed as a cassette attachable/detachable to/from a movable section 130f which functions as a cassette holder, the first imaging means S1 and the second imaging means S2. The X-ray detector 13a is configured in such a manner that the first imaging means S1 extending in a direction parallel to the rotary shaft of the supporting means 11a, and the second imaging means S2 which is used in computed tomography and two-dimensionally expanded are combined as the single imaging element 13e. This imaging element 13e may be formed as a single imaging element or may be formed by bringing a plurality of imaging elements into close contact, but the latter one is more cost effective. There is no particular limitation in the shape of combining the first imaging means S1 and the second imaging means S2.

Figure 39A:
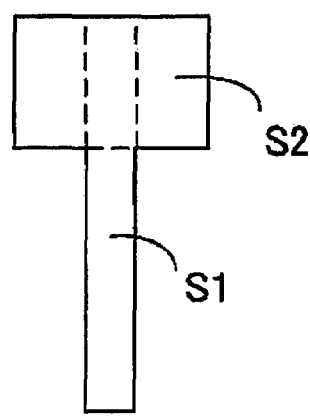
FIGS. 39Aa to 39Ae show examples of a first imaging means S1 and a second imaging means S2 in different shapes.
Figure 39A:
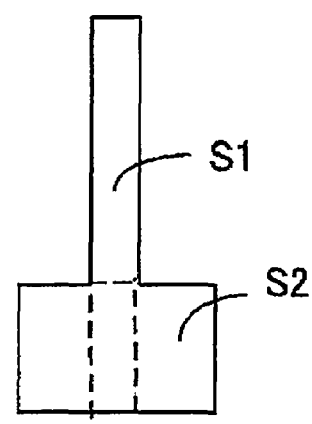
Figure 39A:
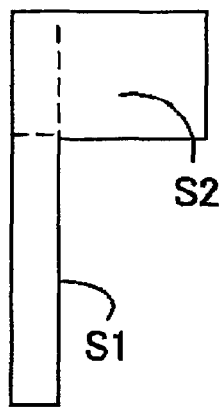
Figure 39A:
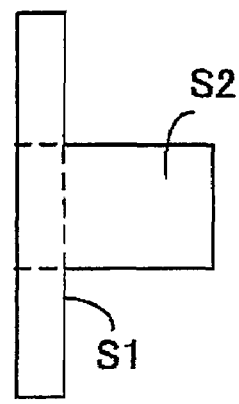
Figure 39A:
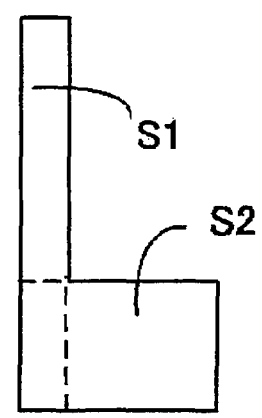

FIGS. 39Aa to 39Ae are diagrams to show different examples in the shape of the first imaging means S1 and the second imaging means S2. For example, FIG. 39 shows examples of sharing the center of the second imaging means S2 in a lateral direction with a part of the first imaging means S1 in a vertical direction, where the second imaging means S2 is positioned in an upper portion of the first imaging means S1 in an example of FIG. 39Aa, and the second imaging means S2 is positioned in a lower portion of the first imaging means S1 in an example of FIG. 39Ab.

Moreover, FIGS. 39Ac to 39Ae show examples of sharing an end portion of the second imaging means S2 in a lateral direction with a part of the first imaging means S1 in a vertical direction. That is, FIG. 39Ac shows an example of positioning the second imaging means S2 in an upper portion of the first imaging means S1, FIG. 39Ad shows an example of positioning the second imaging means S2 in the center of the first imaging means S1, and FIG. 39Ae shows an example of positioning the second imaging means S2 in a lower portion of the first imaging means S1.

Since the movable section 130f for mounting the X-ray detector 13a shown in FIG. 39 has the same configuration with the movable section 130b of FIG. 27a, explanation thereof will be omitted.

Explained next is a basic operation of the radiography apparatus M of this example.

Figure 40:
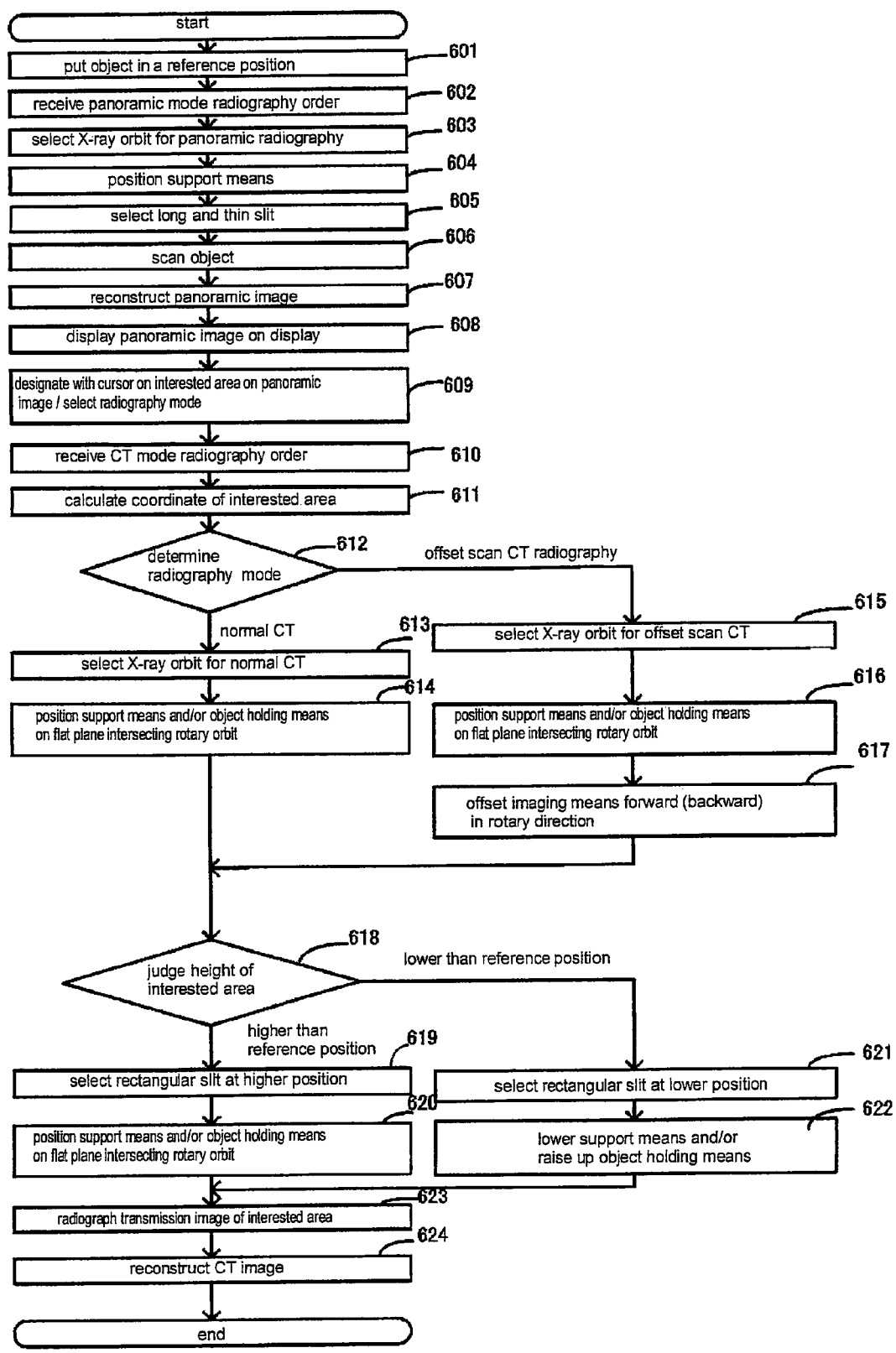
FIG. 40 is a flowchart to explain yet further basic operation of the radiography apparatus.

FIG. 40 is a flowchart showing control procedures by the control means 16 in order to realize the basic operation. According to this flowchart, the control means 16 executes an arrangement step to put the object o in a reference position (step 601), and preliminary radiography steps to perform scanning by using the first imaging means S1, in the same manner with the second embodiment.

Figure 41:
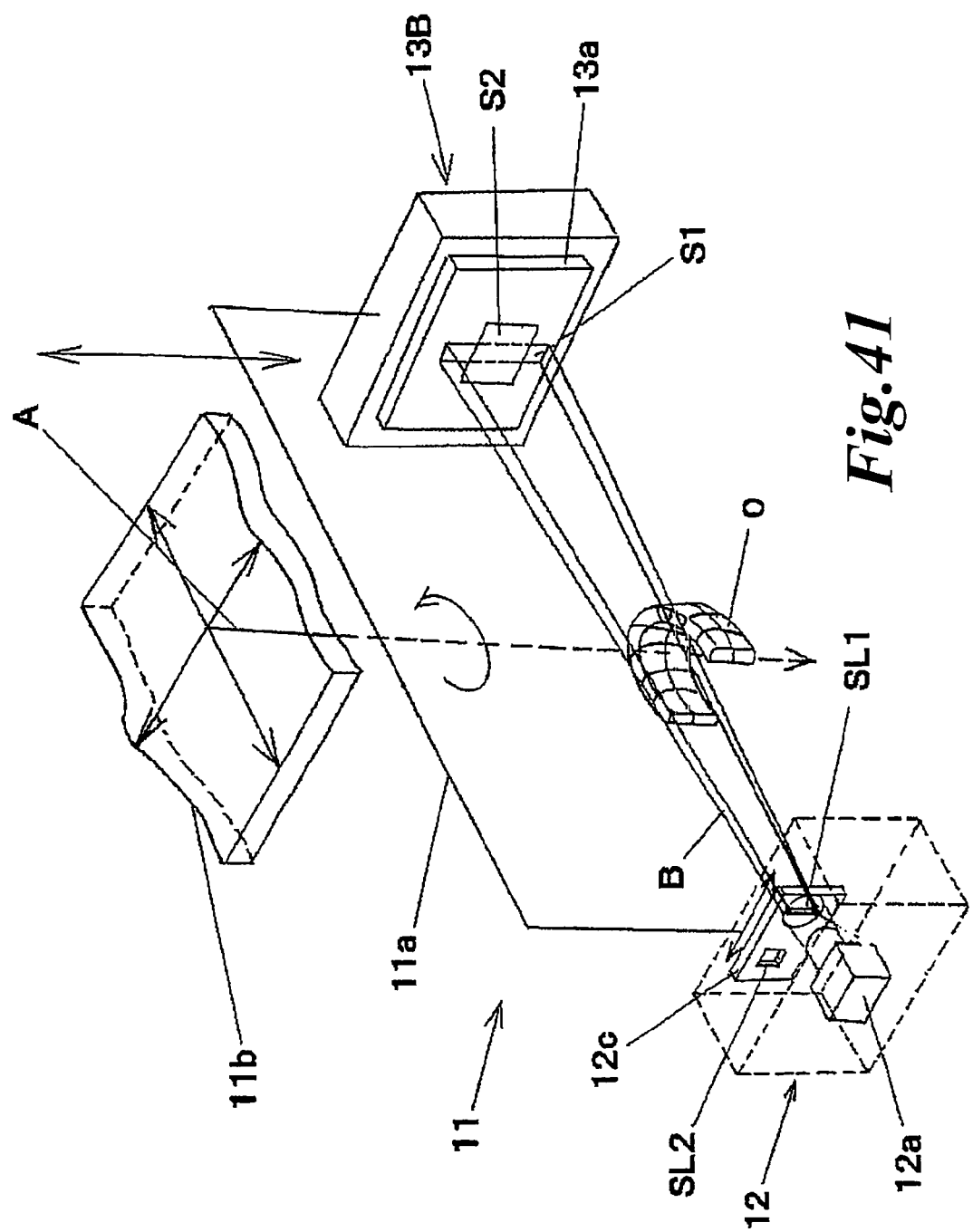
FIG. 41 is yet another schematic diagram to explain a state in scanning.

FIG. 41 is a schematic diagram to explain a state in scanning of the object o. In FIG. 41, an extension line of the rotary shaft A passes through a central portion of a dental arch of a patient who is drawn as the object o. X-ray cone beams are controlled by the narrow grooved slit SL1 of the primary slit plate 12c, and an elongate transmission image of a dental arch made by the X-ray slit beam B is projected to the first imaging means S1. Orbits of the X-ray generating section 12 and the X-ray detecting section 13 are similar to those of the second embodiment.

Next, interested area specifying steps are executed (i.e. steps 607 to 609), including displaying a panoramic image in the display section 14 (step 608), and receiving specification of interested area R in the object o and selection of a type of the second X-ray image by a cursor operation on the display screen or other operation in the operating section 15 (step 609).

Thereafter, if a radiography command of the second X-ray image is received from a keyboard of the operating section 15 or the operation panel 16g (step 610), radiography position adjustment steps are executed. Coordinates of a position of the specified interested area are calculated (step 611), followed by determining a type of the second X-ray image (step 612). If a type of the second X-ray image indicates normal computed tomography, select a normal CT orbit as an X-ray beam orbit (step 613), and move and position the supporting means 11a on a plane intersecting the rotary shaft A (step 614). Meanwhile, if a type of the second X-ray image indicates offset scan computed tomography, select an offset scan CT orbit as an X-ray beam orbit (step 616), move and position the supporting means 11a on a plane intersecting the rotary shaft A (step 616), and further slide the X-ray detector 13a forward or backward in a rotating direction and position the X-ray detector 13a so as to be offset with respect to the X-ray generating section 12 and the interested area R (step 617). Next, a position of the interested area R is determined (step 618), and if the interested area R is positioned higher than a reference position, select the rectangular slit SL2 in the irradiation field changing means 12b (step 619), and raise the supporting means 11a and/or lower the object holding means 11c for positioning in a direction parallel to the rotary shaft A (step 620). Meanwhile, if the interested area R is positioned lower than a reference position, select the slit SL2 in the irradiation field changing means 12b (step 621), and lower the supporting means 11a and/or raise the object holding means 11c for positioning in a direction parallel to the rotary shaft A (step 622).

Thereafter, actual radiography steps are executed, including capturing a transmission image at each predetermined rotation angle on the basis of the positioning in the radiography positioning adjustment steps, (step 623), and reconstructing CT images for a desired sectional plane of the interested area R (step 624).

Figure 42:
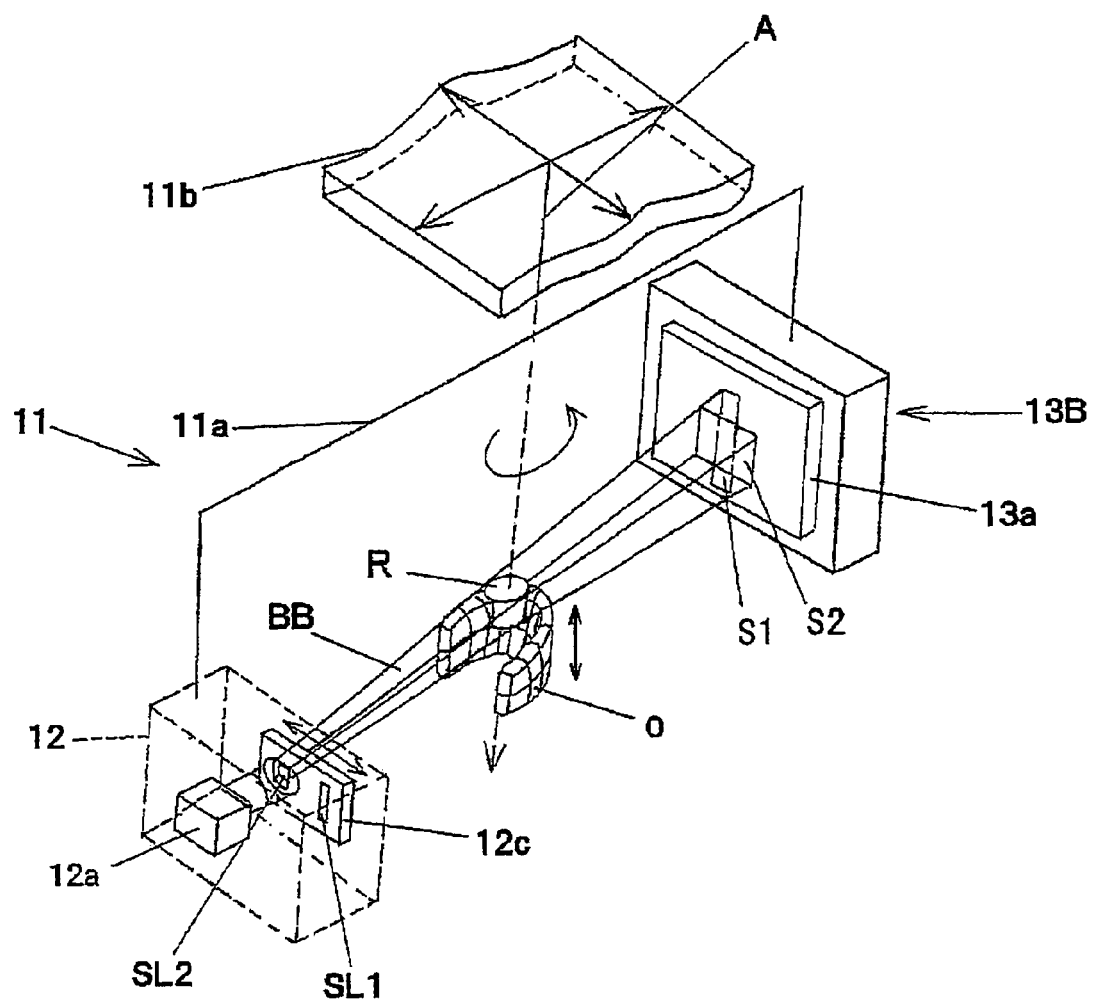
FIG. 42 is yet another schematic diagram to explain a state in transmission image capturing.

FIG. 42 is a schematic diagram to explain a state in capturing a transmission image of the interested area R. FIG. 42 shows a state in normal computed tomography, where an extension line of the rotary shaft A passes through the center of a cylindrical body of the interested area R. X-ray cone beams are also controlled by the rectangular slit SL2 of the primary slit plate 12c, and a transmission image including the entire cylindrical body of the interested area R made by the X-ray broad beam BB is projected to the positioned second imaging means S2. Orbits of the X-ray generating section 12 and the X-ray detecting section 13B are similar to those of the first embodiment.

Fifth Embodiment

Next, a further example of the radiography apparatus M will be explained in detail. In the radiography apparatus of this example, particularly the moving means 11 has a different configuration with respect to the first to fourth embodiments, but a common basic operation and the like is commonly maintained, where the X-ray generating section 12 and the X-ray detecting sections 13, 13A and 13B similar to those of the respective embodiments can be appropriately employed.

Figure 44:
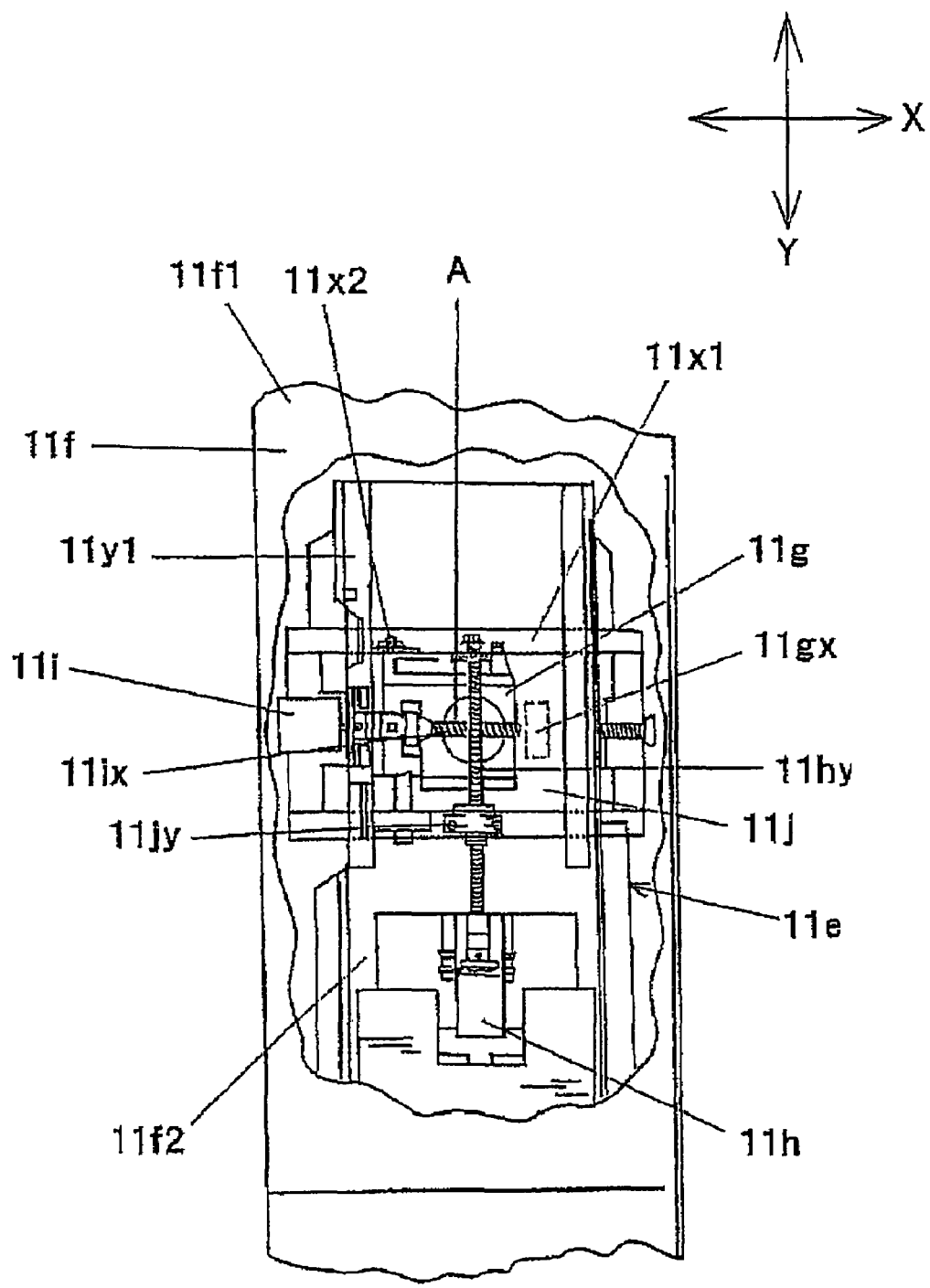
FIG. 44 is a horizontal sectional view to be seen from upward in order to explain an internal configuration of a housing frame.

FIG. 44 is a perspective view to explain an appearance of the radiography apparatus M of this example.

The moving means 11 is composed of the supporting means 11a to which the X-ray generating section 12 and the X-ray detecting section 13 are fixed, the housing frame 11f for rotatably suspending and holding the supporting means 11a by the rotary shaft A, and a main body frame being a fixed section 11b for the housing frame 11f. A hollow shaft is used in the rotary shaft A, where cables connected to the X-ray generation section 12 and the X-ray detecting section 13 are internally arranged and protected, improving the apparatus in appearance. The housing frame 11f is allowed not only to turn the supporting means 11a in radiography but also to move the supporting means up and down in a direction parallel to the rotary shaft A in order to determine a position.

Therefore, the X-Y table 11e for positioning control of a shaft table 11g fixed to the rotary shaft A by two-dimensional control on a plane intersecting the rotary shaft A is incorporated in an upper portion of the housing frame 11f, where the operation panel 16h composed of a display light and a operation switch is provided on a side surface, and the control means 16 as explained in, for example, FIG. 16 is further stored, as will be described later. The object holding means 11c for positioning the object o is also attached to the main body frame.

A chin rest for a patient to put the chin is provided in the center of the object holding means 11c, and this chin rest can be moved up and down or tilted and positioned in accordance with a physique of a patient. The chin rest is thus movably configured to allow adjustments of inclination of an irradiation line with respect to a horizontal plane in each radiography part such as the upper jaw and lower jaw for example, and adjustments so that vertically separated parts, such as the temporomandibular in an upper position and a top end of the lower jaw in a lower position, are positioned to be well in the center of an irradiation field.

Configurations of the moving means 11 and the housing frame 11f will be further explained here. The supporting means 11a can be moved up and down with the housing frame 11f along the main body frame 11b in accordance with a physique of a patient. Accordingly, the X-ray generating section 12 and the X-ray detecting section 13 which are integrally provided in the supporting means 11a are moved with the housing frame 11f with respect to the object holding means 11c.

However, the housing frame 11f and the supporting means 11a may be separately configured and individually moved with respect to the main body frame. A configuration of moving the X-ray generating section 12 and the X-ray detecting section 13 with respect to the housing frame 11f or the object holding means 11c may also be provided. The aforementioned Patent Document 3 filed by the applicant of the present invention discloses such an example of configuring the housing frame 11f and the supporting means 11a separately, and a configuration example of moving the X-ray generating section 12 with respect to the housing frame 11f or the object holding means 11c.

In the aforementioned Patent Document 3, a portion corresponding to the housing frame 11f is referred to as a "patient frame" while a portion corresponding to the supporting means 11a is referred to as an "elevation main body", and an object thereof is to expand a possible radiography region while, for example, adjusting inclination of an irradiation line with respect to a horizontal plane in each radiography region, and adjusting vertically separated parts, such as the temporomandibular in an upper position and a top end of the lower jaw in a lower position, so as to be well positioned in the center of an irradiation field.

A configuration in which the object holding means 11c can be moved up and down or tilted, a configuration of separating the housing frame 11f from the supporting means 11a, and a configuration of moving the X-ray generating section 12 and the X-ray detecting section 13 with respect to the housing frame 11f or the object holding means 11c, may be combined to allow more precise adjustments.

FIG. 44 is a horizontal cross sectional view to be seen from upward in order to explain an internal structure of the housing frame 11f which suspends and holds the supporting means 11a. FIG. 44 shows a structure of the X-Y table 11e in a configuration that a rotary shaft connected to a Y-axis control motor 11h which is fixed to the housing frame 11f is rotated to move a Y-axis table 11j in parallel to the Y axis, and a rotary shaft connected to an X-axis control motor 11i which is fixed to the Y-axis table 11j is rotated to move an X-axis table 11g in parallel to the X axis.

Figure 45:
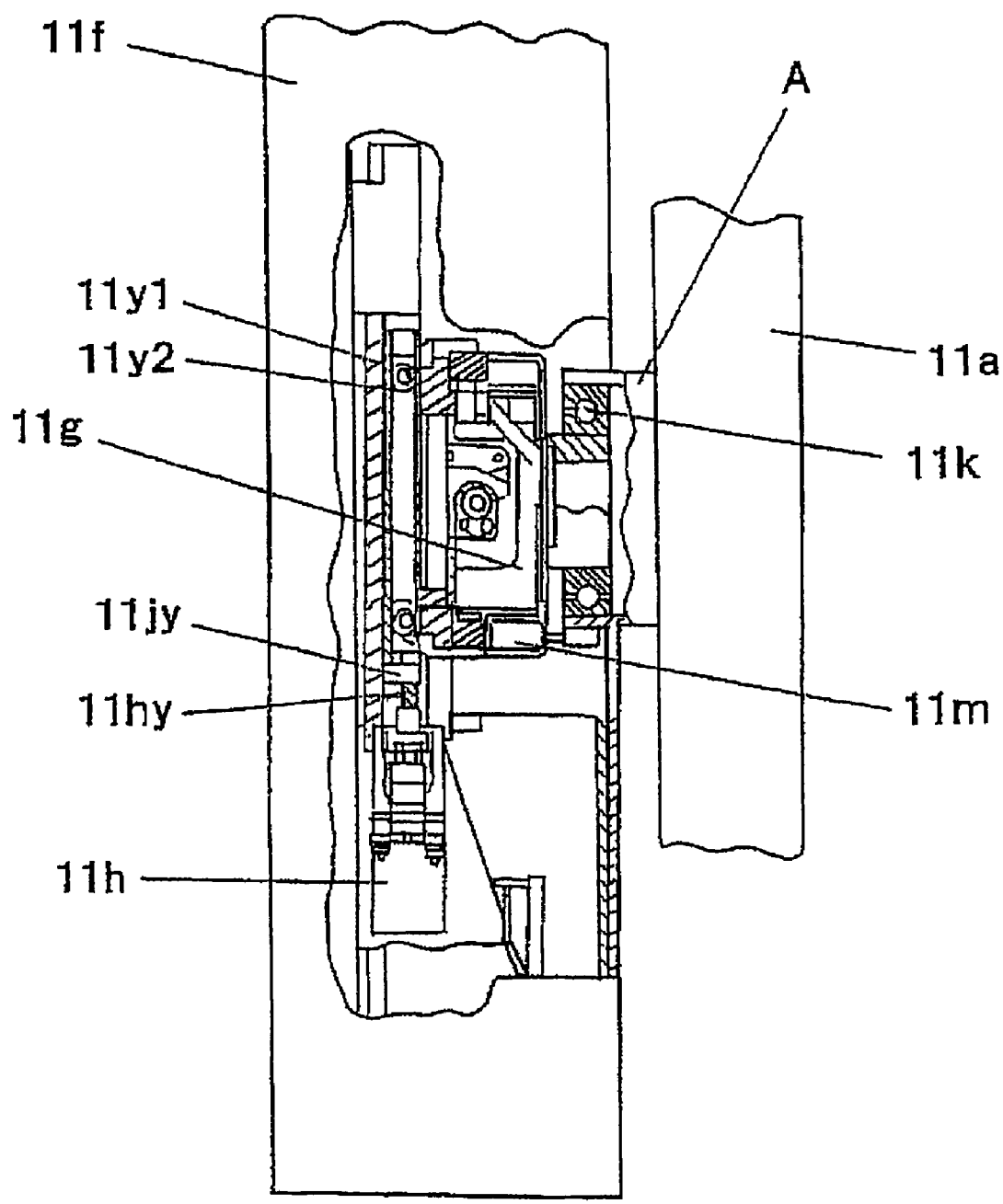
FIG. 45 is a longitudinal sectional view to be seen from a side of a connection portion between the housing frame and a supporting means.

FIG. 45 is a longitudinal sectional view, where a connection portion between the housing frame 11f and the supporting means 11a is seen from sideward. Provided is a configuration that the supporting means 11a is rotatably connected to the rotary shaft A by a ball bearing 11*k*, and the supporting means 11*a* is rotated with respect to the rotary shaft A by driving a rotation control motor 11*m* fixed to the X-axis table 11*g*.

If the configuration is explained more specifically, the housing frame 11*f* is composed of a housing 11*f* and a beam 11*f*2 to which the housing is fixed, where the Y-axis control motor 11*h* is fixed to the beam 11*f*2, and a Y driving axis 11*hy* being a screw shaft is provided in the Y-axis control motor 11*h*, so that a driven member 11*jy* which is fixed to the Y-axis table 11*j* and internally threaded is displaced in the y direction shown in FIG. 44 if the Y-driving axis 11*hy* is rotated. Then, a wheel 11*y*2 is provided in the Y-axis table 11*j*, and a rail 11*y* for guiding the wheel 11*y*2 is provided in the beam 11*f*2, so that the Y-axis table 11*j* is smoothly moved along the rail 11*yl* if the Y-axis control motor 11*h* is driven to rotate.

Meanwhile, the X-axis control motor 11*i* is fixed to the Y-axis table 11*j*, and an X driving shaft 11*ix* being a screw shaft is provided in the X-axis control motor 11*i*, so that a driven member 11*gx* which is fixed to the X-axis table 11*g* and internally threaded is displaced in an x direction shown in FIG. 44 if the X driving shaft 11*ix* is rotated. Then, a wheel 11*x*2 is provided in the X-axis table 11*g*, and a rail 11*x*1 for guiding the wheel 11*x*2 is provided in the Y-axis table 11*j*, so that the X-axis table 11*g* is smoothly moved along the rail 11*x*1 if the X-axis control motor 11*i* is driven to rotate.

The rotation control motor 11*m* being a rotary means is fixed to the X-axis table 11*g* in order to transmit a rotation power to the rotary shaft A by a roller. A ball bearing 11*k* is interposed here between the X table and the rotary shaft A, so that a rotation power of the rotation control motor 11*m* is transmitted to the rotary shaft A with extremely small frictional resistance.

Figure 46:
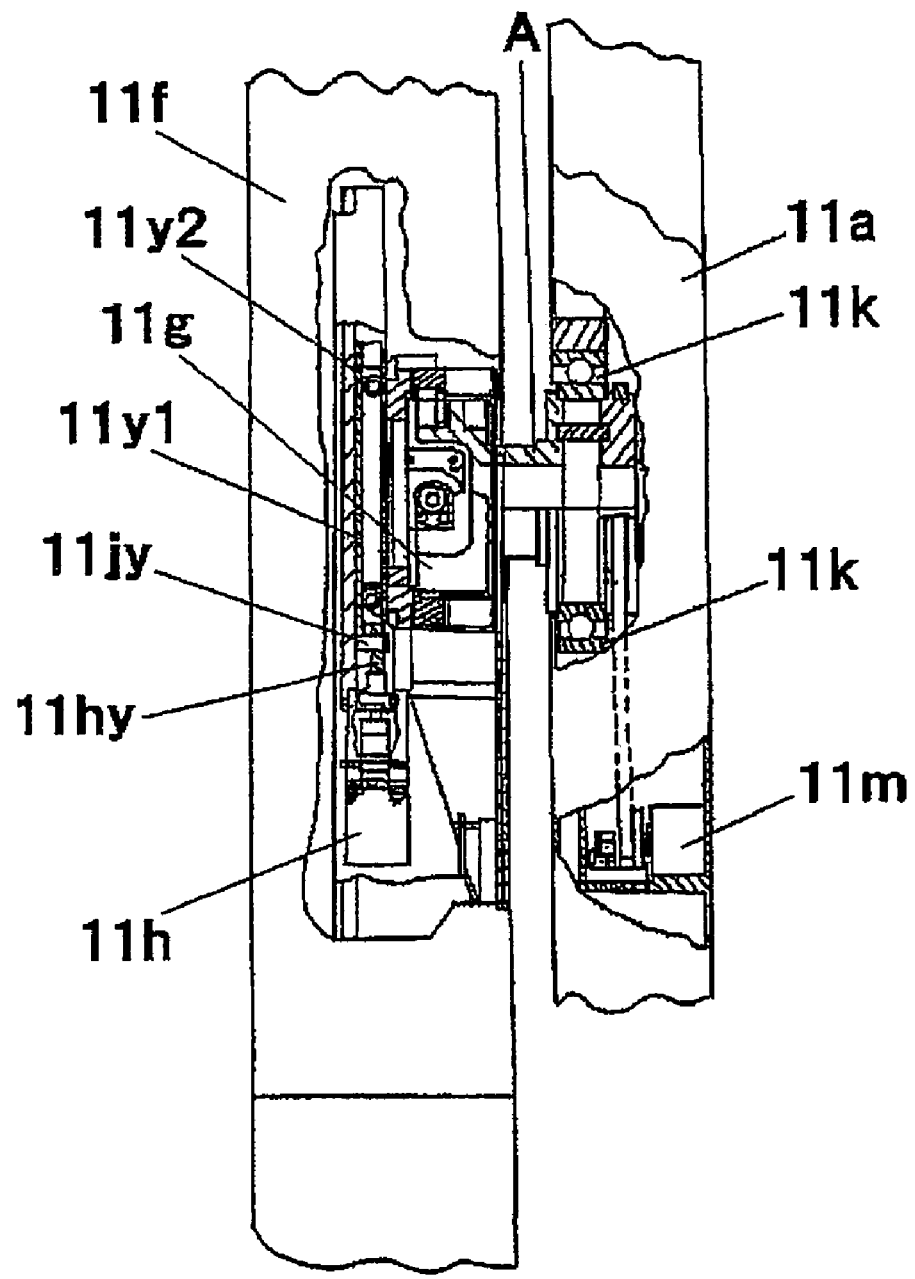
FIG. 46 is a longitudinal sectional view to be seen from a side of the connection portion between the housing frame and the supporting means in another configuration.

FIG. 46 is a modified example of FIG. 45 and the difference is that the rotation control motor 11*m* is internally provided in the supporting means 11*a* so as to transmit a rotation power to the rotary shaft A by a pulley and belt, but the other configuration is common to FIG. 45.

As for the aforementioned X-Y table 11*e*, the techniques described in JP-A-H11-104123, H11-104124, and H11-104125 filed by the applicant of the present invention can be appropriately applied.

The radiography apparatus M of this example can be modified by further attaching a cephalometric radiography means.

Figure 47A:
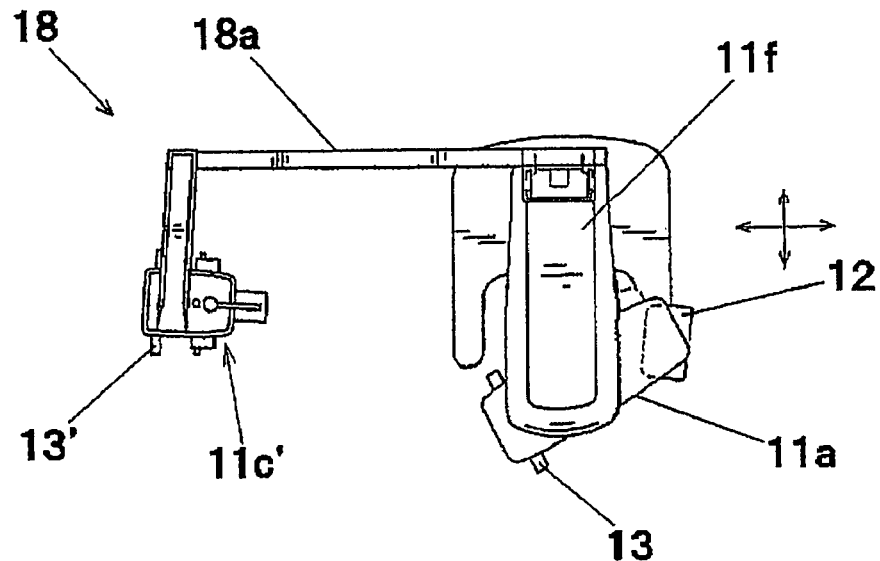
FIGS. 47a and 47b are a plane view and a front view to be seen from upward of a modified example attached with a cephalometric radiography means respectively.
Figure 47B:
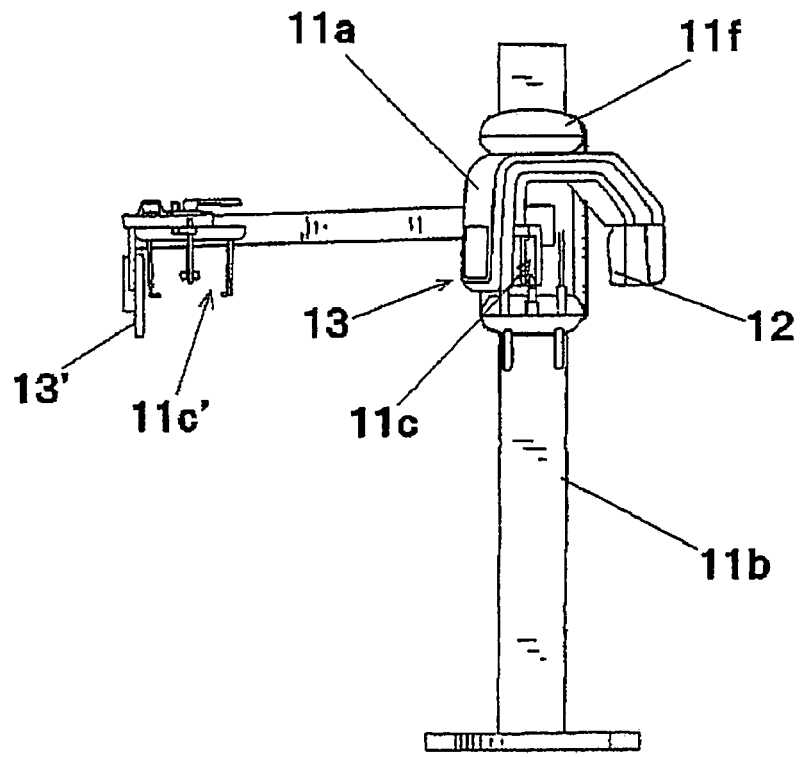

FIGS. 47*a* and 47*b* are a plane view to be seen from upward and a front view of a modified example provided with a cephalometric radiography means 18.

The cephalometric radiography means 18 is composed of an attached arm section 18*a* connected to a rear portion of the housing frame 11*f*, an object holding means 11*c'* for determining a position of the object o in cephalometric radiography, and an X-ray detecting section 13' in a configuration similar to the X-ray detecting section 13.

Figure 48:
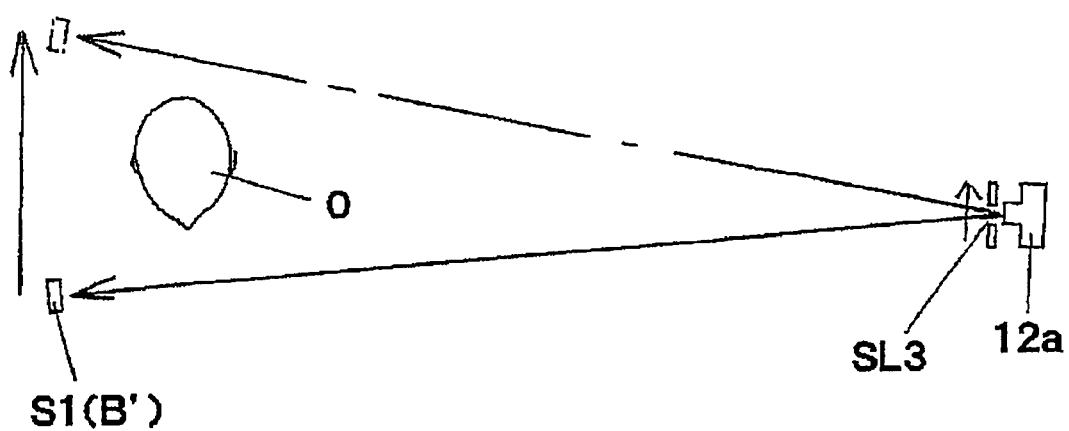
FIG. 48 is a conceptual diagram to explain a state in cephalometric radiography.

Then, the X-ray generating section 12 and the X-ray detecting section 13' are brought into a facing state as shown in FIG. 48 in cephalometric radiography, so that radiography of cephalometric images using the X-ray generating section 12 is made possible.

That is, if the narrow grooved slit SL3 and the first imaging means S1 of the X-ray detecting section 13 are moved synchronously while the X-ray generating section 12*a* is fixed and X-ray cone beams generated therein are controlled by the narrow grooved slit SL3 for cephalometric radiography, a cephalometric image scanned by the X-ray slit beam B can be obtained. Cephalometric images thus captured can also be used as scout view images of this invention.

Moreover, the scout view image of this invention has been achieved for a purpose of setting the interested area R being a target to capture a sectional image in the object o, where a specific part may be selected from an entire image and a high resolution image is not necessarily required in order to achieve the purpose. Accordingly, a configuration to allow selection of an appropriate resolution level as needed is desirable in capturing a scout view image. Such a configuration is valuable from a viewpoint of reducing an exposure amount.

In order to allow selection of a resolution level of a scout view image, binning techniques known as conventional techniques can be introduced. This binning techniques can be easily realized as long as a CCD sensor is basically used as the first imaging means S1, where a CCD to constitute a charge transport section of the sensor uses different control signals for radiography in a normal resolution level and radiography in the other selectable low resolution level. To be more specific, in a process of performing radiography in a normal resolution level followed by transferring charges by the charge transfer section in a bucket brigade manner, radiography charges of four pixels arranged in a lattice pattern may be periodically superimposed so that the four pixels are turned into, for example, vertically or laterally arranged two pixels or one pixel.

It is not necessary to restrict the use of binning techniques exclusively to a scout view, and the techniques may be appropriately used in radiography of an interested area using a scout view image.

Figure 49:
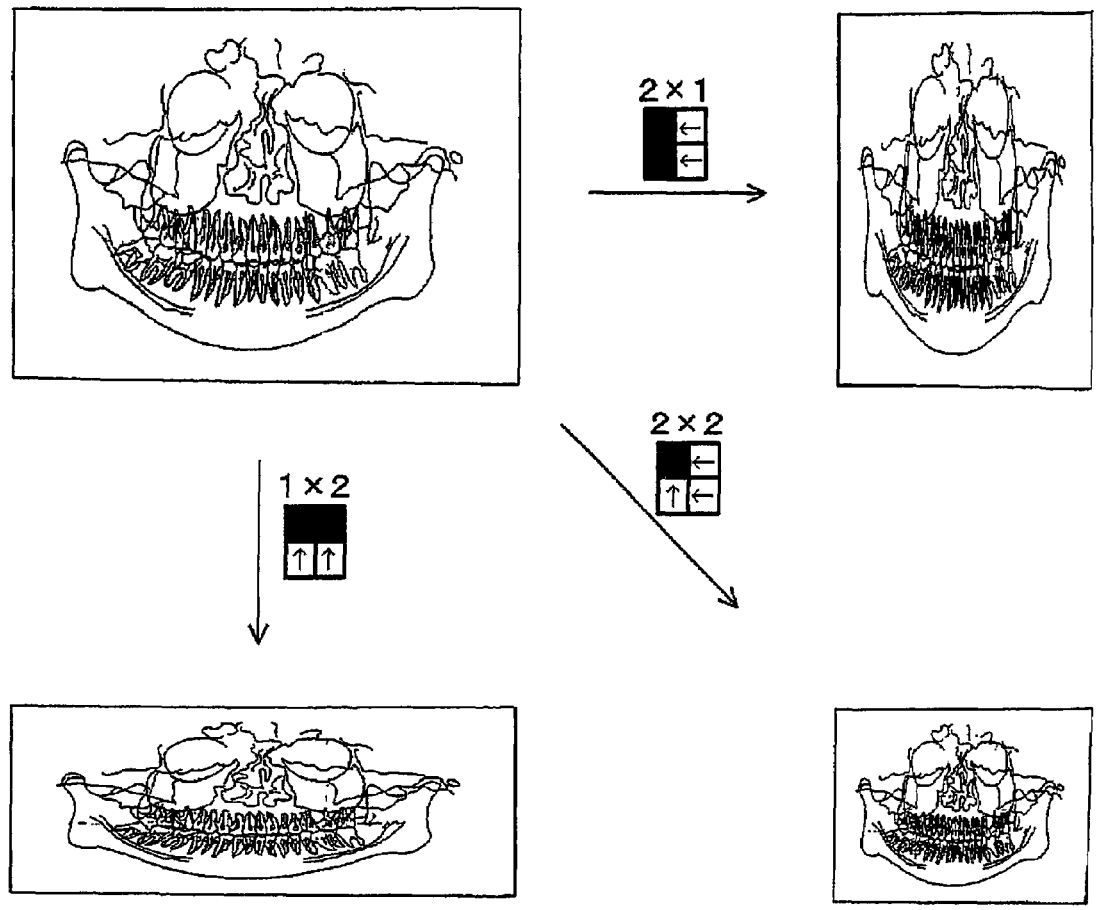
FIG. 49 is a diagram to explain principles of a binning process.

FIG. 49 is a diagram showing an example of such a binning process, describing an original image captured as a scout view image (upper left panoramic image), an image subjected to a 2×1 binning process with respect to radiography charges of the same resolution level (upper right), an image subjected to a 1×2 binning process (lower left), and an image subjected to a 2×2 binning process (lower right). A vertically expanded image obtained by the 2×1 binning process and a laterally expanded image obtained by the 1×2 binning process can be displayed in the display section 14 in a correct aspect ratio by simple image processing such as a thinning process. Such image processing is normally carried out due to originally different resolution levels between radiography images and images displayed in the display section 14, and not newly required for binning.

Reduction of an exposure amount as an effect here is achieved by an effect of reducing an X-ray amount irradiated by the X-ray generating section 12 or accelerating a rotation speed of the moving means 11 by taking account of an increased amount of radiography charges because radiography charges after a binning process are increased due to superimposing under the same radiography condition. Reduction of a similar X-ray exposure amount can be expected in either case, but a testee who is the object o has less stress under short radiography time with an accelerated rotation speed.

A similar binning process can be introduced to the case where a CMOS sensor is employed as an imaging element. This case will be briefly explained below in accordance with a circuit diagram to explain a basic configuration of a CMOS sensor.

Figure 50:
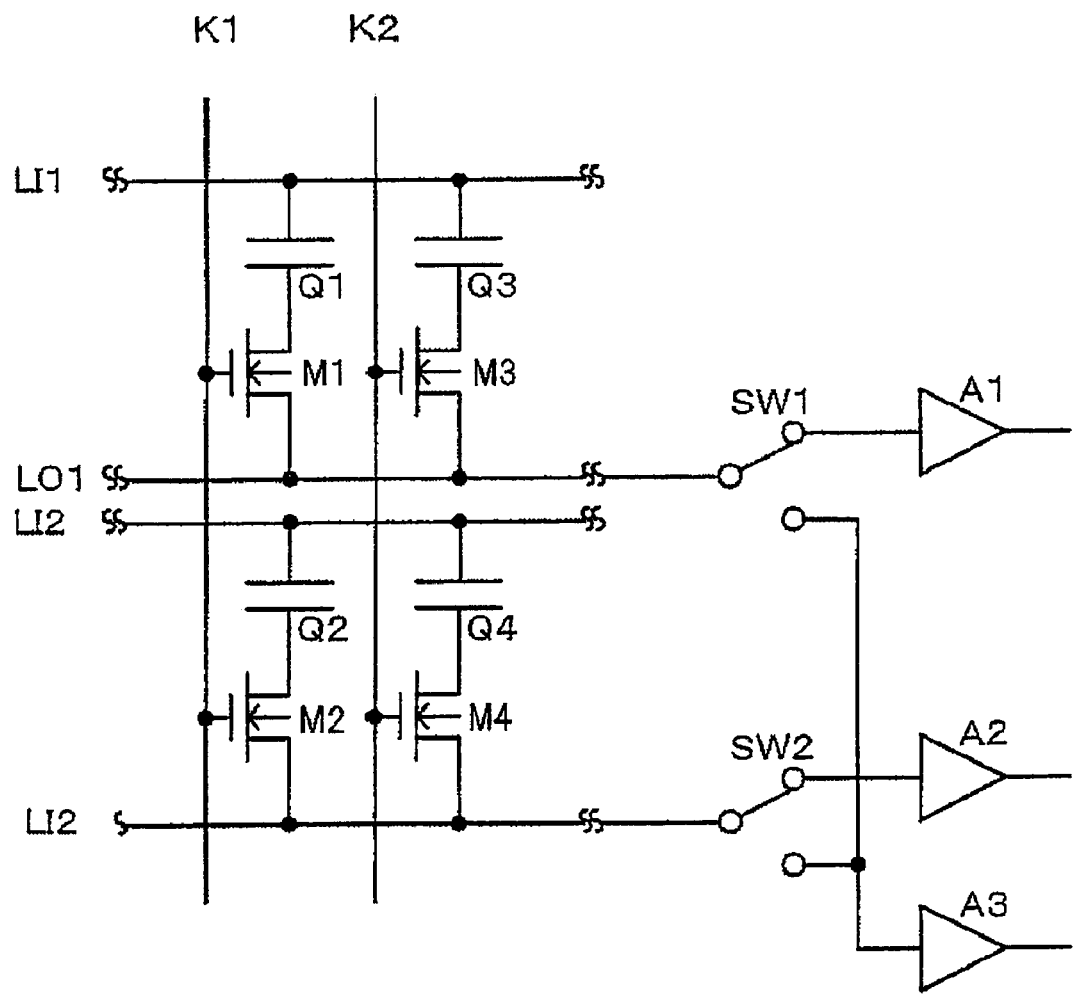
FIG. 50 is a simplified circuit diagram of a CMOS sensor.

FIG. 50 is a diagram describing a simplified circuit of four pixels of the CMOS sensor. This circuit is provided with capacitors corresponding to respective four pixels which are adjacent in a lattice pattern between lines L1 and LO1 or lines LI2 and LO2, MOS transistors M1 to M4 to constitute switches for reading out radiography charges stored by the respective capacitors, sense amplifiers A1 to A3 for generating voltage signals corresponding to read radiography charges, and switches SW1 and SW2 composed of the MOS transistors for selectively connecting the lines LO1 and LO2 to the sense amplifiers A1 to A3.

When normal radiography is carried out according to this circuit, the switches SW1 and SW2 are initially controlled to provide a state that the lines LO1 and LO2 are connected to the sense amplifiers A1 and A2 respectively. Then, after capturing images, a line K1 is initially activated to read out charges Q1 and Q2 to the lines LO1 and LO2 respectively, where voltage signals generated by the sense amplifiers A1 and A2 are converted into digital signals by sampling in an A/D converter and the like not shown, followed by discharging the lines LO1 and LO2 for once to activate a line K2. As a result, voltage signals corresponding to charges Q3 and Q4 are generated in the sense amplifiers A1 and A2 at this time and theses signals are converted into digital signals by sampling. Due to such operation, the radiography charges Q1 to Q4 of the entire pixels of the CMOS sensor are converted into respective digital signals.

In case of performing the 2×1 binning process, the switches SW1 and SW2 are controlled to provide a state that the lines LO1 and LO2 are connected to the sense amplifiers A1 and A2 respectively. Then, after capturing images, the lines K1 and K2 are simultaneously activated to read out and superimpose the both radiography charges Q1 and Q3 to the line LO1 and simultaneously read out and superimpose the both radiography charges Q2 and Q4 to the line LO2. As a result, the sense amplifier A1 generates voltage signals corresponding to the superimposed charges Q1+Q3, and the sense amplifier A2 generates voltage signals corresponding to the superimposed charges Q2+Q4, so that these voltage signals are subjected to sampling and A/D conversion.

In case of performing the 1×2 binning process, the switches SW1 and SW2 are controlled to provide a state that the lines LO1 and L02 are both connected to the sense amplifier A3. Then, after capturing images, the line K1 is initially activated to read out and superimpose the radiography charges Q1 and Q2 to the lines LO1 and LO2 which are short-circuited to each other at this time. Therefore, the sense amplifier A3 generates voltage signals corresponding to the superimposed charges Q1+Q2, and these voltage signals are subjected to sampling and A/D conversion. Thereafter, the lines LO1 and LO2 are discharged for once to activate the line K2, and the radiography charges Q3 and Q4 are read out and superimposed to the lines LO1 and LO2. As a result, the sense amplifier A3 generates voltage signals corresponding to the superimposed charges Q3+Q4, and these voltage signals are subjected to sampling and A/D conversion.

In case of performing the 2×2 binning process, the switches SW1 and SW2 are controlled to provide a state that the lines LO1 and LO2 are both connected to the sense amplifier A3. Then, after capturing images, the lines K1 and K2 are simultaneously activated to read out and entirely superimpose the radiography charges Q1, Q2, Q3 and Q4 to the lines LO1 and LO2 which are short-circuited to each other at this time. Therefore, the sense amplifier A3 generates voltage signals corresponding to the superimposed charges Q1+Q2+Q3+Q4, and these voltage signals are subjected to sampling and A/D conversion.

Such binning processes in capturing a scout view image can be introduced to the radiography apparatus M of the aforementioned respective embodiments.

Ideas of this invention can also be applied to radiography apparatuses used for purposes other than medical treatments. That is, the case of conducting nondestructive inspection radiography after scouting and other cases are considered for industrial purposes, and it is desirable that ideas of this invention is applied to radiography apparatuses having such purposes.

The invention claimed is:

1. A medical radiography apparatus comprising a supporting means to support an X-ray generating section and an X-ray detecting section, both of the sections facing each other, and a moving means to move the supporting means relative to an object to be examined held by an object holding means, whereby an X-ray image of the object is obtained by operating said moving means while irradiating an X-ray beam from said X-ray generating section, wherein
said supporting means is turnable by said moving means, wherein
said X-ray generating section selectively generates an X-ray slit beam and an X-ray broad beam by switching control, wherein
said X-ray detecting section comprises a first imaging means to generate an X-ray image in response to the X-ray slit beam and a second imaging means to generate an X-ray image in response to the X-ray broad beam, and wherein
said medical radiography apparatus comprises;
a display section to display a first X-ray image generated by the X-ray slit beam and said first imaging means;
an operating section to specify a desired interested area on the first X-ray image displayed in said display section; and
a control means to control said moving means in order to generate a predetermined sectional image as a second X-ray image by using the X-ray broad beam and said second imaging means with respect to the interested area specified by said operating section.

2. A medical radiography apparatus comprising a supporting means to support an X-ray generating section and an X-ray detecting section, both of the sections facing each other, and a moving means to move said supporting means relative to an object to be examined held by an object holding means, whereby an X-ray image of the object is obtained by operating said moving means while irradiating an X-ray beam from said X-ray generating section, wherein
said supporting means is turnable by said moving means, wherein said X-ray detecting section has a first imaging means extending in a direction parallel to a rotary shaft of said supporting means to generate an X-ray image in response to an X-ray slit beam and a second imaging means to generate an X-ray image in response to an X-ray broad beam, both of said imaging means being arranged on a single imaging plane, wherein
said X-ray generating section has an irradiation field changing means to selectively generate the X-ray slit beam to be irradiated to said first imaging means and the X-ray broad beam to be irradiated to said second imaging means by switching the shape of the X-ray beams and to change an irradiation field of the X-ray broad beam in a direction parallel to an axial direction of said rotary shaft, and wherein
said medical radiography apparatus comprises:
a display section to display a first X-ray image generated by the X-ray slit beam and said first imaging means;
an operating section to specify a desired interested area on the first X-ray image displayed in said display section; and
a control means to control said irradiation field changing means and said moving means in order to generate a second X-ray image as a CT image by the X-ray broad beam and said second imaging means with respect to the interested area specified by said operating section.

3. The medical radiography apparatus according to claim 1, wherein
said X-ray detecting section comprises said first imaging means extending in a direction parallel to a rotary shaft of said supporting means and said second imaging means, both of said imaging means being arranged individually, and an imaging means moving means to move said second imaging means in a direction parallel to said rotary shaft of said supporting means, wherein
said X-ray generating section comprises an irradiation field changing means to change an irradiation field of the X-ray broad beam in a direction parallel to said rotary shaft, and wherein
said medical radiography apparatus comprises
a control means to control said imaging means moving means, said irradiation field changing means and said moving means in order to generate the second X-ray image as a CT image with respect to the interested area specified by said operating section.

4. The medical radiography apparatus according to claim 1, wherein
said X-ray detecting section has said first imaging means extending in a direction parallel to a rotary shaft of said supporting means and said second imaging means, both imaging means being combined with each other, with common shared portions, and wherein
said X-ray generating section comprises
an irradiation field changing means to selectively generate the X-ray slit beam to be irradiated to said first imaging means and the X-ray broad beam to be irradiated to said second imaging means by switching the shape of the X-ray beams, and wherein
said medical radiography apparatus comprises
a control means to control said irradiation field changing means and said moving means in order to generate said second X-ray image as a CT image by the X-ray broad beam and said second imaging means with respect to the interested area specified by said operating section.

5. The medical radiography apparatus according to any one of claims 1 to 4, wherein
at least one of a panoramic image, a cephalometric image, and a liner scan transmission image is generated as the first X-ray image.

6. The medical radiography apparatus according to any one of claims 1 to 4, wherein
said X-ray generating section and said X-ray detecting section are moved by said moving means along an orbit for panoramic radiography in obtaining a panoramic image.

7. The medical radiography apparatus according to any one of claims 1 to 4, wherein
the specified interested area is entirely projected while constantly projecting a part of the interested area by said second imaging means being offset forward or backward in a rotating direction of said X-ray detecting section, thereby realizing a computed tomography in the interested area.

8. The medical radiography apparatus according to any claim 1, wherein
said moving means is controlled two-dimensionally in two directions defined on a plane intersecting a rotary shaft of said supporting means.

9. The medical radiography apparatus according to claim 1, wherein
said moving means is controlled three-dimensionally in two directions defined on a plane intersecting a rotary shaft of said supporting means and in one direction parallel to said rotary shaft.

10. The medical radiography apparatus according to any one of claims 2 to 4, wherein
said moving means is controlled two-dimensionally in two directions defined on a plane intersecting said rotary shaft.

11. The medical radiography apparatus according to any one of claims 2 to 4, wherein
said moving means is controlled three-dimensionally in two directions defined on a plane intersecting said rotary shaft arid in one direction parallel to said rotary shaft.

* * * * *